United States Patent [19]
Teebor et al.

[11] Patent Number: 5,871,992
[45] Date of Patent: Feb. 16, 1999

[54] MAMMALIAN ENDONUCLEASE III, AND DIAGNOSTIC AND THERAPEUTIC USES THEREOF

[75] Inventors: George W. Teebor; Timothy P. Hilbert, both of New York, N.Y.

[73] Assignee: New York University, New York, N.Y.

[21] Appl. No.: 808,550

[22] Filed: Feb. 27, 1997

Related U.S. Application Data

[60] Provisional application No. 60/012,323, Feb. 27, 1996.

[51] Int. Cl.$^6$ .................................................. C12N 9/22
[52] U.S. Cl. .................................................. 435/199
[58] Field of Search .................................................. 435/199

[56] References Cited

PUBLICATIONS

Tomkinson, A.L., et. al. (1990) Nucl. Acids Res. 18(4), 929–935.
Doetsch, P.W., et. al. (1987) Mol. Cell. Biol. 7(1), 26–32.
Asahara, et al., Biochemistry, 28:4444–4449 (1989).
Aspinwall et al. (1997) Proc. Natl. Acad. Sci. U.S.A. 94:109–14.
Bacchetti, et al., Biochim. Biophys. Acta, 390:285–297 (1975).
Bailly, et al., Nucleic Acids Res., 17:3617–3618 (1989).
Bailly, et al., Biochemical J., 242:565–572 (1987);.
Boorstein, et al., Biochemistry, 28:6164–6170 (1989).
Breimer, et al., J. Biol. Chem., 259:5543–4458 (1984).
Brent, Biophys. J., 13:399–401 (1973).
Burn, et al., Gene (Amst.), 161:183–187 (1995).
Cunningham, et al., Proc. Natl. Acad. Sci. U.S.A., 82:474–478 (1985).
Demple, et al., Nature, 287:203–208 (1980).
Demple(1994), Ann. Rev. Biochem., 63: 915–48.
Dodson(1994), J. Biol. Chem., 269: 32709–12.
Doetsch, et al., Biochemistry, 25:2212–2220 (1986).
Duker, et al., Nature, 255:82–84 (1975).
Higgins, et al., Biochemistry, 26:1683–1688 (1987).
Hilbert, et al., Biochemistry, 35:2505–2511 (1996).
Huq(1992), Eur. J. Biochem.,206:833–9.
Kim(1989), J. Biol. Chem., 264:2739–45.
Mazumder, et al., Biochemistry, 30:1119–1126 (1991).
Ness, et al., Biochim. Biophys Acta, 520:111–121 (1978).
Ouellette, et al., Genome, 36:32–42 (1993).
Radman(1976), J. Biol. Chem., 251: 1438–45.
Strniste, et al., Proc. Natl. Acad. Sci. U.S.A., 72:1997–2001 (1975).
Thayer, et al., EMBOJ, 14:4108–4120 (1995).
Wilson, et al., Nature, 368:32–38 (1994).
Hilbert et al. (1997) J. Biol. Chem. 272:6733–40.
Kim et al. (1995) J. Biol. Chem. 270:13620–9.
Lee et al. (1987) Biochem. Biophys. Res. Commun. 149:93–101.
SwissProt Databank (1996) Accession # P31378.

Primary Examiner—Charles L. Patterson, Jr.
Attorney, Agent, or Firm—Klauber & Jackson

[57] ABSTRACT

The present invention relates to isolated mammalian homologues of the DNA repair enzyme, E. coli endonuclease III. These mammalian enzymes have a glycosylase/AP lyase activity. Included in the present invention are fusion proteins containing the active mammalian endonuclease III. Also included are nucleic acids encoding the mammalian enzymes of the present invention and fusion proteins thereof, along with cloning, and expression vectors which contain these nucleic acids. In addition, associated diagnostic, therapeutic and pharmaceutical materials are included, along with related methods of making and using the same. The present invention also includes methods of expressing the recombinant forms of mammalian endonuclease III enzymes and fusion proteins thereof, and methods for isolating these expressed enzymes and proteins, as well as the methods for isolating the natural forms of mammalian endonuclease III enzymes.

9 Claims, 16 Drawing Sheets

```
A:  1  MNKAKRLEILTRLRENNPHPTTELNFSSPFELLIAVLLSAQATDVSVNKATAKLYPVANTPAAMLELGVE  70
B:  1   MRKDMIAPVDTMGCHKLADPLAAPPVHRFQVLVALMLSSQTRDEVNAAAMKRLKDHGLSIGKILEFKVP  69
C:                                                             LTVDSILQTDDS
                                PVDQLGAEHCFDPSA

A: 71  GVKTYIKTIGLYNSKAENIIKTCRILLEQHNGEVPEDRAALEALPGVGRKTANVVLNTAFGWPT.IAV  137
B: 70  DLETILCPVGFYKRKAVYLQKTAKILKDDFSGDIPDSLDGLCALPGVGPKMANLVMQIAWGECVGIAV  137
C:     TLGALIVPVGF                                            QGTVNGIAV

A:138  DTHIFRVCNRTQFAPGKN.VEQVEEKLLKVVPAEFKVDCHHWLILHGRYTCIARKPRCGSCIIEDLC  203
B:138  DTHVHRIS.NRLGWIKTSTPEKTQKALEILLPKSEWQPINHLLVGFGQMQCQPVRPKCGTCLCRFTC  203
C:     XTHVP                                          *LWSEINGLLVGFGQTCLPIRP
D:                                           WLPR?LWHEINGLLVGFGQQTCLPVHPRCHACLNQALC
E:                                      HRIANRLKWTKKMTKSPEETRRNLE?WLPRVLWSEINGLLVGFGQ?ICLPVHPRCQACL?KALC

A:204  EYKEKVDI  211
B:204  PSSTAKNVKSETEETSTSIEVKQEVEDEFEDEKPAKKIKKTRKTRTKIEVKTESET  259
C:
D:       PAAQGL
E:       PAAQGL
```

FIG.4

Human Endonuclease III cDNA Sequence.
Length: 1046bp

```
CCCACGCGTC CCGCCGCCTT GAGCGCGAGG ATGCTGACCC GGAGCCGGAG
CCTGGGACCC GGGGCTGGGC CGCGGGGGTG TAGGGAGGAG CCCGGGCCTC
TCCGGAGAAG AGAGGCTGCA GCAGAAGCGA GGAAAAGCCA CAGCCCCGTG
AAGCGTCCGC GGAAAGCACA GAGACTGCGT GTGGCCTATG AGGGCTCGGA
CAGTGAGAAA GGTGAGGGGG CTGAGCCCCT CAAGGTGCCA GTCTGGGAGC
CCCAGGACTG GCAGCAACAG CTGGTCAACA TCCGTGCCAT GAGGAACAAA
AAGGATGCAC CTGTGGACCA TCTGGGGACT GAGCACTGCT ATGACTCCAG
TGCCCCCCCA AAGGTACGCA GGTACCAGGT GCTGCTGTCA CTGATGCTCT
CCAGCCAAAC CAAAGACCAG GTGACGGCGG GCGCCATGCA GCGACTGCGG
GCGCGGGGCC TGACGGTGGA CAGCATCCTG CAGACAGATG ATGCCACGCT
GGGCAAGCTC ATCTACCCCG TCGGTTTCTG GAGGAGCAAG GTGAAATACA
TCAAGCAGAC CAGCGCCATC CTGCAGCAGC ACTACGGTGG GGACATCCCA
GCCTCTGTGG CCGAGCTGGT GGCGCTGCCG GGTGTTGGGC CAAGATGGC
ACACCTGGCT ATGGCTGTGG CCTGGGGCAC TGTGTCAGGC ATTGCAGTGG
ACACGCATGT GCACAGAATC GCCAACAGGC TGAGGTGGAC CAAGAAGGCA
ACCAAGTCCC CAGAGGAGAC CCGCGCCGCC CTGGAGGAGT GGCTGCCTAG
GGAGCTGTGG CACGAGATCA ATGGACTCTT GGTGGGCTTC GGCCAGCAGA
CCTGTCTGCC TGTGCACCCT CGCTGCCACG CCTGCCTCAA CCAAGCCCTC
TGCCCGGCCG CCCAGGGTCT CTGATGGCCG CATGGCTCTG GCCGAGGTGC
CGCTGTGGCC ACCGTCTGTG AAGTGGCTTT ACGCTTCAGG AAGCCACGCC
TGTTGAATAA AGCTTTGGTG TGTTTGCAAA AAAAAAAAA AAAAAA
```

FIG.5

Human Endonuclease III Coding Sequence (Open Reading Frame)
Length: 894bp

```
ATGCTGACCC GGAGCCGGAG CCTGGGACCC GGGGCTGGGC CGCGGGGGTG TAGGGAGGAG CCCGGGCCTC
TCCGGAGAAG AGAGGCTGCA GCAGAAGCGA GGAAAAGCCA CAGCCCCGTG AAGCGTCCGC GGAAAGCACA
GAGACTGCGT GTGGCCTATG AGGGCTCGGA CAGTGAGAAA GGTGAGGGGG CTGAGCCCCT CAAGGTGCCA
GTCTGGGAGC CCCAGGACTG GCAGCAACAG CTGGTCAACA TCCGTGCCAT GAGGAACAAA AAGGATGCAC
CTGTGGACCA TCTGGGACT GAGCACTGCT ATGACTCCAG TGCCCCCCCA AAGGTACGCA GGTACCAGGT
GCTGCTGTCA CTGATGCTCT CCAGCCAAAC CAAAGACCAG GTGACGGCGG GCGCCATGCA GCGACTGCGG
GCGCGGGGCC TGACGGTGGA CAGCATCCTG CAGACAGATG ATGCCACGCT GGGCAAGCTC ATCTACCCCG
TCGGTTTCTG GAGGAGCAAG GTGAAATACA TCAAGCAGAC CTGCAGCAGC ACTACGGTGG
GGACATCCCA GCCTCTGTGG CCGAGCTGGT GGCGCTGCCG GGTGTTGGGC CCAAGATGGC ACACCTGGCT
ATGGCTGTGG CCTGGGCAC TGTGTCAGGC ATTGCAGTGG ACACGCATGT GCACAGAATC GCCAACAGGC
TGAGGTGGAC CAAGAAGGCA ACCAAGTCCC CAGAGGAGAC CCGCGCCGCC CTGGAGGAGT GGCTGCCTAG
GGAGCTGTGG CACGAGATCA ATGGACTCTT GGTGGGCTTC GGCCAGCAGA CCTGTCTGCC TGTGCACCCT
CGCTGCCACG CCTGCCTCAA CCAAGCCCTC TGCCCCGGCCG CCCAGGGTCT CTGA
```

FIG.6

Human Endonuclease III Amino Acid Sequence

MLTRS RSLGP GAGPR GCREE PGPLR RREAA AEARK SHSPV KRPRK AQRLR VAYEG SDSEK GEGAE PLKVP
VWEPQ DWQQQ LVNIR AMRNK KDAPV DHLGT EHCYD SSAPP KVRRY QVLLS LMLSS QTKDQ VTAGA MQRLR
ARGLT VDSIL QTDDA TLGKL IYPVG FWRSK VKYIK QTSAI LQQHY GGDIP ASVAE LVALP GVGPK MAHLA
MAVAW GTVSG IAVDT HVHRI ANRLR WTKKA TKSPE ETRAA LEEWL PRELW HEING LLVGF GQQTC LPVHP
RCHAC LNQAL CPAAQ GL

MAMMALIAN ENDONUCLEASE III, AND DIAGNOSTIC AND THERAPEUTIC USES THEREOF

GOVERNMENTAL SUPPORT

The research leading to the present inventions was funded in part by Grant Nos. CA 16669, CA 49869, CA 16087 and GM 07308 from the National Institutes of Health. The government may have certain rights in the invention.

CROSS-REFERENCE TO RELATED APPLICATIONS

The present Application is a non-provisional application claiming the priority of copending provisional U.S. Ser. No. 60/012,323 filed Feb. 27, 1996, the disclosure of which is hereby incorporated by reference in its entirety. Applicants claim the benefits of this Application under 35 U.S.C. §119(e).

TECHNICAL FIELD OF THE INVENTION

The present invention relates generally to the measurement and repair of DNA damage to cells resulting from oxidation or ultraviolet radiation, in mammals including animals and humans, and more particularly to materials identified herein as modulators of DNA damage, and to the diagnostic and therapeutic uses to which such modulators may be put, and the like.

BACKGROUND OF THE INVENTION

When a pyrimidine residue in cellular DNA becomes modified by oxidation, reduction or hydration of its 5,6 double bond, repair is initiated by a DNA-glycosylase activity which cleaves the N-glycosyl bond of the damaged residue releasing the modified base and creating an abasic (AP) site in the DNA backbone. Such DNA glycosylase activities have been identified in bacteria, yeast and mammalian species [Brent, *Biophys. J.*, 13:399–401 (1973); Bacchetti, et al., *Biochim. Biophys. Acta*, 390:285–297 (1975); Duker, et al., *Nature*, 255:82–84 (1975); Ness. et al., *Biochim. BiophysActa*, 520:111–121 (1978); Demple, et al., *Nature*, 287:203–208 (1980): Cunniningham, et al., *Proc. Natl. Acad. Sci. U.S.A.*, 82:474–478 (1985); Doetsch. et al., *Biochemistry*, 25:2212–2220 (1986); Boorstein, et al., *Biochemistry*, 28:6164–6170 (1989)]. The DNA repair enzyme *E. coli* endonuclease III was the first of such enzymes to be described. It was identified not on the basis of its DNA glycosylase activity, but rather by its nicking activity directed against UV-irradiated DNA [Radman, *J. Biol. Chem.*, 251:1438–1445 (1976)]. Subsequently, it was shown that nicking of UV-irradiated DNA resulted from 2 enzymatic activities; a DNA-glycosylase which released pyrimidine (cytosine and/or uracil) hydrates from the DNA backbone, yielding an apyrimidinic (AP) site [Boorstein, et al., 1989, supra], and an activity which effected strand cleavage via β-elimination of the 3' phosphate group of the apyrimidinic sugar residue [Bailly, et al., *Biochemical J.* 242:565–572 (1987); Kim, et al., *J. Biol. Chem.*, 264:2739–2745 (1989); Mazumder, et al., *Biochemistry*, 30:1119–1126 (1991)]. The latter activity has been termed an AP lyase to distinguish it from AP endonucleases, such as exonuclease III or endonuclease IV, which catalyze strand cleavage via hydrolysis of phosphodiester bonds [Bailly, et al., *Nucleic Acids Res.*, 17:3617–3618 (1989)]. Endonuclease III is one of a group of enzymes, including T4 endonuclease V and the *E. coli* Fpg protein (MutM), which demonstrate both DNA-glycosylase and AP lyase activities [Demple, et al., *Ann. Rev. Biochem.*, 63:915–948 (1994); Dodson, et al., *J. Biol. Chem.*, 269:32709–32712 (1994)].

In addition to excising pyrimidine hydrates, the DNA-glycosylase activity of endonuclease III also excises pyrimidine glycols, ring-contracted pyrimidine derivatives, such as 5-hydroxymethylhydantoin, and urea residues composed of the N1-C2-N3 atoms of the pyrimidine skeleton [Strniste, et al., *Proc. Natl. Acad. Sci. U.S. A.*, 72:1997–2001 (1975); Demple, et al., 1980, supra; Breimer, et al., *J. Biol. Chem.*, 259:5543–4458 (1984); Cunningham, et al., 1985, supra]. Enzyme activities functionally analogous to endonuclease III have been identified in bacteria other than *E. coli*, in yeast, and in mammalian cells and tissues through the use of UV-irradiated, chemically oxidized, and γ-irradiated DNA as substrates [Brent, 1973 supra; Bacchetti, et al., 1975, supra; Duker, et al., 1975, supra; Ness, et al., 1978, supra, Doetsch, et al., 1986, supra]. Extracts of Hela cells have been shown to contain a thymine glycol DNA-glycosylase [Higgins, et al., *Biochemistry*, 26:1683–1688 (1987)]. It has also been demonstrated that both endonuclease III and Hela cell extracts released cytosine hydrate (as well as its deamination product, uracil hydrate) from UV-irradiated DNA [Boorstein, et al., 1989, supra]. Kim, et al. [1989, supra] described 2, or possibly 3, UV-endonuclease activities in Hela cells by monitoring the nicking of UV-irradiated circular DNA. Huq et al. [*Eur. J. Biochem*, 206:833–839 (1992)] reported a 25 fold purification of an endonuclease III-like activity from calf thymus and stated that the N-terminal sequence of this protein was not homologous to other known proteins.

In view of the significance and activity of endonuclease III as recited in the literature, it would be desirable, and a need therefore exists, to elucidate the mammalian homologs, and other potentially active fragments, that may be applied to the development of both diagnostic and therapeutic modalities, to treat the adverse effects of exposure to radiation and oxidation. It is therefore toward the fulfillment of this need that the present invention is directed.

SUMMARY OF THE INVENTION

In accordance with the present invention, a DNA damage repair modulator has been purified, the human homolog has been identified, and a fusion protein comprising the human homolog has been made and isolated. In particular, the modulator of DNA damage repair comprises mammalian Endonuclease III, and specifically, the human homolog thereof, including the full length cDNA, and the polypeptide for which it codes, and related fusion proteins.

The present invention also relates to a recombinant DNA molecule or cloned gene, or a degenerate variant thereof, which encodes a DNA repair modulator; preferably a nucleic acid molecule, in particular a recombinant DNA molecule or cloned gene, encoding the DNA repair modulator has a nucleotide sequence or is complementary to a DNA sequence shown in FIG. 8, SEQ ID NO:1.

The human and murine DNA sequences of the DNA repair modulator of the present invention or portions thereof, may be prepared as probes to screen for complementary sequences and genomic clones in the same or alternate species. The present invention extends to probes so prepared that may be provided for screening cDNA and genomic libraries for the DNA repair modulator. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences disclosed herein. Correspondingly, the preparation of antisense RNA and ribozymes are included herein.

The present invention also includes DNA repair modulator proteins having the activities noted herein, and that display the amino acid sequences set forth and described above, as set forth in FIG. 8, SEQ ID NO:2; including that depicted in FIG. 7, SEQ ID NO:42, which comprises amino acids 8–304 of SEQ ID NO:2.

The present invention also includes fusion proteins comprising a mammalian endonuclease III of the present invention; and nucleic acids that encode such fusion proteins. In one embodiment, the fusion protein comprises a human endonuclease III. In a preferred embodiment, the human endonuclease III has the amino acid sequence of SEQ ID NO:42 (amino acids 8–304 of SEQ ID NO:2). In one embodiment the fusion protein is a mammalian endonuclease III fused to glutathione S-transferase.

In a further embodiment of the invention, the full DNA sequence of the recombinant DNA molecule or cloned gene so determined or a corresponding fusion protein may be operatively linked to an expression control sequence which may be introduced into an appropriate host. The invention accordingly extends to unicellular hosts transformed with the cloned gene or recombinant DNA molecule comprising a DNA sequence encoding the present DNA repair modulator(s), and more particularly, the complete DNA sequence determined from the sequences set forth above and in FIG. 8, SEQ ID NO:1 or a fusion protein thereof.

According to other preferred features of certain preferred embodiments of the present invention, a recombinant expression system is provided to produce biologically active animal or human DNA repair modulator(s).

More particularly, the present invention provides a mammalian endonuclease III polypeptide, nucleic acids encoding the same, methods for producing the polypeptide, methods for treating diseases or disorders associated with DNA damage, such as occurs in UV-irradiated tissues, chemically oxidized tissues, and gamma-irradiated tissues, and methods for diagnosing susceptibility to DNA damage by determining the level of activity of the endonuclease III in tissues.

In a further aspect the invention provides a mammalian endonuclease III purified greater than about 5000-fold, which endonuclease III demonstrates pyrimidine hydrate DNA-glycosylase activity, thymine glycol DNA-glycosylase activity, and lyase activity, and reductively cross links with a thymine glycol containing oligodeoxynucleotide. Further, as illustrated in the Examples, infra, the endonuclease in 100 mM NaCl may elute from a 1 ml single stranded-DNA-cellulose chromatography column eluted with a 12.5 ml gradient of 100 to 600 mM NaCl at 0.2 ml/min in about fractions 12–18, and more preferably in about fractions 15–17.

As demonstrated in the Examples, infra, the present endonuclease III can have an apparent molecular weight of 29 kDa as determined by gel filtration, and an apparent molecular weight of 31 kDa as determined by SDS-PAGE analysis.

In a further aspect the present endonuclease III has a partial amino acid sequence selected from the group consisting of SEQ ID NOs: 25, 26, 27, 28 in FIG. 4, line C (bovine), SEQ ID NO:6 in FIG. 4. line D (human), and SEQ ID NO:20 in FIG. 4, line E (rat). In a further embodiment, the endonuclease III has an amino acid sequence selected from the group consisting of bovine endonuclease III, human endonuclease III, and rat endonuclease III. In a particular embodiment, the endonuclease III is a human endonuclease III having an amino acid sequence corresponding to FIG. 8, SEQ ID NO:2.

The present invention extends to a purified nucleic acid encoding a mammalian endonuclease III, which endonuclease III demonstrates pyrimidine hydrate DNA-glycosylase activity, thymine glycol DNA-glycosylase activity, and lyase activity, and reductively cross links with a thymine glycol containing oligodeoxynucleotide. In an illustrative embodiment, the endonuclease III in 100 mM NaCl elutes from a 1 ml single stranded-DNA-cellulose chromatography column eluted with a 12.5 ml gradient of 100 to 600 mM NaCl at 0.2 ml/min in about fractions 12–18, and preferably elutes in about fractions 15–17. In a further illustration, the endonuclease III has a Stokes radius corresponding to a protein having a molecular weight of 29 kDa as determined by gel filtration, and a molecular weight of 31 kDa as determined by SDS-PAGE analysis. As illustrated, the purified nucleic acid of the present invention may encode endonuclease III having a partial amino acid sequence selected from the group consisting of FIG. 4, SEQ ID NOs:25, 26, 27, 28 in line C, SEQ ID NO:6 in line D and SEQ ID NO:20 in line E; particularly, the purified nucleic acid encodes the endonuclease III having an amino acid sequence selected from the group consisting of bovine endonuclease III. human endonuclease III, and rat endonuclease III.

In specific embodiments, illustrated, the purified nucleic acid has a nucleotide sequence corresponding or complementary to the nucleotide sequence selected from the group consisting of SEQ ID NOs:25, 26, 27, 28 in a bovine, SEQ ID NO:6 in a human and SEQ ID NO:20 in a rat. In another embodiment, the nucleic acid is hybridizable under stringent conditions to a nucleic acid having a nucleotide sequence corresponding or complementary to the nucleotide sequence selected from the group consisting of FIG. 4, SEQ ID NOs:25, 26, 27, 28 in line C. SEQ ID NO:6 in line D and SEQ ID NO:20 in line E. In a preferred embodiment, the mammalian endonuclease III is a human endonuclease III. In a more purified embodiment the purified nucleic acid encodes the endonuclease III having an amino acid sequence corresponding to SEQ ID NO:2. In the most preferred embodiment of this type the purified nucleic acid has a nucleotide sequence as depicted in SEQ ID NO:1, from nucleotide 9 to nucleotide 920.

As can be readily appreciated by one of ordinary skill in the art, the mammalian endonuclease III can be an allelic variant, with minor nucleotide or amino acid sequence variations as compared to the specific mammalian endonuclease IIIs exemplified herein. Such allelic variants include, but are not limited to, mutants with decreased or ablated, or increased, enzymatic activity.

In a specific embodiment, the purified nucleic acid is DNA encoding the mammalian endonuclease III. Such a DNA molecule may be a recombinant DNA vector. Preferably, the DNA vector is an expression vector, wherein the DNA encoding the mammalian endonuclease III, preferably a human endonuclease III, is operatively associated with an expression control sequence. The present invention accordingly extends to a recombinant host cell comprising the DNA expression vector capable of expressing the mammalian endonuclease III, preferably human endonuclease III. The invention provides a corresponding method for producing a mammalian endonuclease III comprising expressing the expression vector in a recombinant host cell under conditions that provide for expression of the endonuclease III. Thus, the invention advantageously provides for expression of recombinant mammalian endonuclease III, which is important for direct therapy, identification of agonists and antagonists of endonuclease III, and production of anti-mammalian endonuclease III antibodies.

The recombinant DNA of the invention allows for direct gene therapy of conditions associated with a mutation or decreased expression of mammalian endonuclease III in a mammal, preferably a human. According to the invention, such gene therapy may be effected by transient expression of the endonuclease III in affected, differentiated tissues, or it may involve long term or indefinite expression in by gene transfer into progenitor or undifferentiated cells. Thus, in a further embodiment, the invention provides a recombinant virus comprising the DNA vector. The recombinant virus may be selected from the group consisting of a retrovirus, herpes simplex virus (HSV), papillomavirus, Epstein Barr virus (EBV), adenovirus, and adeno-associated virus (AAV). In another embodiment, the invention provides a naked DNA vector.

The invention provides a method for increasing the level of expression of a mammalian endonuclease III comprising introducing an expression vector into a host in vivo under conditions that provide for expression of the endonuclease III. The expression vector may be a viral expression vector, or it may be a naked DNA expression vector. Various methods are known in the art for transfecting cells with DNA in vivo, including techniques such as lipofection, targeted DNA transfer, and the like.

According to one embodiment of the invention, the expression vector may be introduced into tissue exposed to radiation prior to exposure to the radiation. For example, a human who may be exposed to the sun or to gamma irradiation may undergo prophylactic gene therapy, preferably with a transient expression vector, prior to exposure to the radiation source. In a specific embodiment, the gene therapy vector of the invention may be provided in a gel, cream, or lotion for application to the skin. Preferably, such a gel, cream, or lotion contains a sunscreen.

In another embodiment, the expression vector is introduced into tissue exposed to radiation after exposure to the radiation.

As noted above, in a preferred aspect the foregoing nucleic acids, DNA molecules, and associated methods involve human endonuclease III, and the treatment or administration to a human in vivo.

The invention further provides a method for treating a disease or disorder associated with DNA damage in a mammal, comprising increasing the level of mammalian endonuclease III in cells demonstrating DNA damage, wherein the endonuclease III demonstrates pyrimidine hydrate DNA-glycosylase activity, thymine glycol DNA-glycosylase activity, and lyase activity, and reductively cross links with a thymine glycol containing oligodeoxynucleotide. In one embodiment, the level of mammalian endonuclease III is increased by administration of purified endonuclease III to the cells demonstrating DNA damage. In another embodiment, the level of mammalian endonuclease III is increased by administration of a recombinant expression vector to the cells demonstrating DNA damage, which expression vector provides for expression of the mammalian endonuclease III in vivo. Preferably, the expression vector is a viral expression vector or a naked DNA expression vector. The expression vector may be introduced into tissue exposed to radiation prior to exposure to the radiation, or it may be introduced into tissue exposed to radiation after exposure to the radiation.

The present invention further provides oligonucleotide probes, particularly labeled probes, and PCR primers to isolate nucleic acids, such as mRNA, cDNA, and genomic DNA, encoding a mammalian endonuclease III, preferably a human endonuclease III, with the proviso that such probes do not correspond to the 3' EST (expressed sequence tags) from *H. sapiens* deposited with GenBank and assigned accession number F04657 or Rattus sp. deposited with GenBank and assigned accession number H33255. Such probes can be used to isolate a nucleic acid encoding a mammalian endonuclease III (preferably a human endonuclease III), detect the level of expression of a mammalian endonuclease III in a tissue sample, or detect a mutation in a mammalian endonuclease III, e.g., by hybridization (or lack of hybridization) of a specific probe under highly stringent conditions, or by detection of a mutated sequence in a PCR-amplified DNA by methods such as single stranded molecular weight polymorphisms, or the introduction or elimination of a restriction site. Thus, the invention is directed to an oligonucleotinde of greater than 10 nucleotides which hybridizes under stringent conditions, wherein the $T_m$ is greater than 60° C. Preferably, the oligonucleotide hybridizes at a $T_m$ of greater than 65° C. In a specific embodiment, the oligonucleotide hybridizes at 40% formamide, with 5× or 6× SCC; in another specific embodiment, the oligonucleotide hybridizes at 50% formamide. In a specific embodiment, exemplified infra, the probe is an oligonucleotide having the nucleotide sequence GTGGCACGAGATCAATGGACTCTTG, SEQ ID NO:4. In another specific embodiment, exemplified infra, hybridization is detected using biotinylated sequence-specific oligonucleotides and magnetic streptavidin beads to enrich a library prior to screening.

In addition, the present invention provides an antibody that specifically binds to the mammalian endonuclease III, preferably a human endonuclease III. The antibody of the invention may be polyclonal or monoclonal. An antibody of the invention can be used to detect the presence or level of mammalian endonuclease III, i.e., in situ in a tissue biopsy or a tissue (using in vivo imaging techniques), or in vitro in a tissue homogenate.

The present invention also provides biochemical techniques for detecting mammalian endonuclease III, e.g., by detecting enzymatic activity characteristic of endonuclease III. However, by providing for high purification of endogenous endonuclease III, the invention allows for quantitative evaluation of the level of endonuclease III activity in a tissue. In one embodiment, the enzymatic activity can be evaluated by DNA-glycosylase activity (e.g., pyrimidine hydrate or thymine glycol DNA-glycosylase activity). Alternatively, enzymatic activity can be measured by lyase activity. In another aspect, enzymatic activity can be measured by evaluating the level of reductive cross linking to a thymine glycol-containing DNA oligodeoxynucleotide. In a particular aspect, the amount of cross-linked polypeptide can be compared to uncross linked polypeptide to determine whether a mutation in the expressed polypeptide affects enzymatic activity, and thus the ability to form cross links.

Thus, a particular advantage of the present invention is the ability to detect or measure increased sensitivity to DNA damage comprising detecting a decrease in the level of activity of a mammalian endonuclease III in cells from a mammal, wherein the endonuclease III demonstrates pyrimidine hydrate DNA-glycosylase activity, thymine glycol DNA-glycosylase activity, and lyase activity, and reductively cross links with a thymine glycol containing oligodeoxynucleotide. In other words, the invention provides for identifying individuals, especially human, at risk for radiation-induced DNA damage because of insufficient endonuclease III DNA repair activity. It is a particular advantage that the present invention provides any one of three methods for detecting endonuclease III levels, which can be used independently or in a combination of one or more.

Furthermore, in addition to detecting the level of endonuclease III (whether mRNA expression, protein expression, or enzymatic activity), the invention allows for determination of inactivating mutations. Thus, in one embodiment the decrease in the level of activity of mammalian endonuclease III is detected by detecting a decrease in the level of expression of the mammalian endonuclease III polypeptide. Such a decrease can be evaluated by immunological methods, by biochemical methods (e.g., purification and detection of band intensity by PAGE, or enzymatic activity), or by binding to DNA. In another aspect, the decrease can be evaluated with specific nucleic acid probes, such that a decrease in the level of activity of mammalian endonuclease III is detected by detecting a decrease in the level of expression of the mammalian endonuclease III mRNA, or a mutation in the DNA encoding the endonuclease III. As noted above, such a mutation can be detected by hybridization techniques, by PCR, or biochemically.

Individuals who are found to have decreased levels of DNA repair activity mediated by endonuclease III can be treated by limiting exposure to radiation sources, using greater protection (such as sunscreen or radiation screens), monitored for neoplasms for early intervention, or treated to increase the level of endonuclease III activity as described above.

The present invention naturally contemplates several means for preparation of the DNA repair modulator(s) or endonuclease III, including as illustrated herein known recombinant techniques, and the invention is accordingly intended to cover such synthetic preparations within its scope. The isolation of the cDNA and amino acid sequences disclosed herein facilitates the reproduction of the DNA repair modulator(s) by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate DNA repair modulator or endonuclease III activity of target mammalian cells by interrupting or potentiating the DNA repair modulator or endonuclease III. In one instance, the test drug could be administered to a cellular sample with the ligand that activates the DNA repair modulator or endonuclease III, or an extract containing the activated DNA repair modulator or endonuclease III, to determine its effect upon the binding activity of the DNA repair modulator or endonuclease III to any chemical sample (including DNA), or to the test drug, by comparison with a control.

The assay system could more importantly be adapted to identify drugs or other entities that are capable of binding to the DNA repair modulator or endonuclease III, and/or DNA repair modulator or endonuclease III factors or proteins, either in the cytoplasm or in the nucleus, thereby inhibiting or potentiating DNA repair modulator or endonuclease III activity. Such assay would be useful in the development of drugs that would be specific against particular cellular activity, or that would potentiate such activity, in time or in level of activity.

In yet a further embodiment, the invention contemplates antagonists of the activity of a DNA repair modulator or endonuclease III, and in particular, an agent or molecule that inhibits DNA repair modulator or endonuclease III. In a specific embodiment, the antagonist can be a peptide having the sequence of a portion of an active domain of a DNA repair modulator or endonuclease III.

The present invention likewise extends to the development of antibodies against the DNA repair modulator(s) or endonuclease III, including naturally raised and recombinantly prepared antibodies. For example, the antibodies could be used to screen expression libraries to obtain the gene or genes that encode the DNA repair modulator or endonuclease III. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating DNA repair modulator or endonuclease III activity.

Thus, the DNA repair modulator(s) or endonuclease III, their analogs and/or analogs, and any antagonists or antibodies that may be raised thereto, are capable of use in connection with various diagnostic techniques, including immunoassays, such as a radioimmunoassay, using for example, an antibody to the DNA repair modulator or endonuclease III that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the DNA repair modulator or endonuclease III, or to identify drugs or other agents that may mimic or block their activity.

The system or test kit may comprise a labeled component prepared by one of the radioactive and/or enzymatic techniques discussed herein, coupling a label to the DNA repair modulator or endonuclease III, their agonists and/or antagonists, and one or more additional immunochemical reagents, at least one of which is a free or immobilized ligand, capable either of binding with the labeled component, its binding partner, one of the components to be determined or their binding partner(s).

The present invention represents a significant advance, as the presence and activity of mammalian endonuclease III has, at best, been postulated. By providing mammalian endonuclease III, the present invention opens an avenue for repairing DNA damaged by irradiation or oxidation, thus avoiding transformation of damaged tissues and development of cancers. This advance has important implications for treating or preventing skin cancers, and cancers associated with gamma irradiation, including those resulting from exposure to radiation from high altitude aviation, nuclear medicine, nuclear reactors, or nuclear weapons. It is a particular advantage that the present invention provides a human endonuclease III polypeptide, nucleic acids encoding the polypeptide, and associated therapeutic and diagnostic methods.

Accordingly, it is a principal object of the present invention to provide a DNA repair modulator or mammalian endonuclease III and its subunits in purified form that exhibits certain characteristics and activities associated with the enzyme endonuclease III.

It is a further object of the present invention to provide antibodies to the DNA repair modulator or endonuclease III and its subunits, and methods for their preparation, including recombinant means.

It is a further object of the present invention to provide a method for detecting the presence, amount and activity of the DNA repair modulator or endonuclease III and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the DNA repair modulator or endonuclease III, and/or its subunits in mammals.

It is a still further object of the present invention to provide a method for the treatment of mammals to control the amount or activity of the DNA repair modulator or endonuclease III or subunits thereof, so as to alter the adverse consequences of such presence or activity, or where beneficial, to enhance such activity.

It is a still further object of the present invention to provide a method for the treatment of mammals to control the amount or activity of the DNA repair modulator or endonuclease III or its subunits, so as to treat or avert the adverse consequences of invasive, spontaneous or idiopathic pathological states.

It is a still further object of the present invention to provide pharmaceutical compositions for use in therapeutic methods which comprise or are based upon the DNA repair modulator or endonuclease III, its subunits, their binding partner(s), or upon agents or drugs that control the production, or that mimic or antagonize the activities of the DNA repair modulator or endonuclease III.

Other objects and advantages will become apparent to those skilled in the art from a review of the ensuing description which proceeds with reference to the following illustrative drawings.

BRIEF DESCRIPTION OF THE DRAWINGS

FIG. 4. Amino acid sequence alignment of $E.$ $coli$ endonuclease III (Line A), $C.$ $elegans$ translated protein (Line B), bovine primary amino acid sequences for peptides of 15, 23, 14, and 22 amino acids respectively (Line C), $H.$ $sapiens$ and Rattus sp. sequences obtained by translation of partial cDNA sequence (Line D and E. respectively ). X in sequence C represents an indeterminate amino acid residue.? in sequences D and E represents indeterminate nucleotide sequences. The 6 amino acid region presented in boldface and italic constitutes a portion of the active site of endonuclease III. A 22 amino acid region of near identity between the predicted $C.$ $elegans$ sequence, the primary bovine sequence, and the $H.$ $sapiens$ and Rattus sp. translated partial cDNA sequences is presented in boldface. The 4 cysteine residues presented in double underlined type represent the ligands of the iron-sulfur cluster of $E.$ $coli$ endonuclease III.

FIG. 5 is a cDNA encoding essentially full length human endonuclease III (encoding amino acids 8–304 of SEQ ID NO:2) prepared and identified in accordance with the present invention.

FIG. 6 is the coding sequence (open reading frame) of human endonuclease III (amino acids 8–304 of SEQ ID NO:2) prepared and identified in accordance with the present invention.

FIG. 7 is the amino acid sequence prepared from the translation of the cDNA of FIG. 5.

FIG. 8. Nucleotide and deduced amino acid sequence of the human pyrimidine hydrate-thymine glycol DNA glycosylase/AP lyase. The sequences of peptides obtained by proteolytic digestion of purified bovine pyrimidine hydrate-thymine glycol DNA glycosylase/AP lyase are in italics and are aligned with the homologous human amino acid sequence.

FIG. 13. Spectroscopic analysis.

FIG. 15. Alignment of the amino acid sequence of *E. coli* endonuclease III with those of putatively homologous proteins from 3 evolutionary domains. The amino acid sequence of *E. coli* endonuclease III (Eco) is aligned with homologous sequences from *H. influenza,* (Hin), *B. subtilis* (Bsu), *M. jannaschii* (Mja), *S. pombe* (Spo), *C. elegans* (Cel), *H. sapiens* (Hsa), as well as two unique homologous sequences from *S. cerevisiae* (Sce and Sce non Fe-S). Residues in black boxes indicate identical sequences. Residues in gray boxes indicate conservative substitution. Dashes denote gaps in sequence introduced to maximize alignment. Numbers in the left hand column refer to the first amino acid residue in each line of the respective protein sequences. Numbers in the lower right hand indicate the total number of amino acid residues in each protein sequence. In archeons and eukaryotes the proteins which are homologous to *E. coli* endonuclease III have unique extensions at their N-and/or C-termini. For the sake of clarity these extensions have been omitted from the figure. Alignment of residues 83–304 of the human enzyme with residues 2–209 of the *E. coli* enzyme demonstrates that there is 29.3 % identity and 51.9% similarity between the 2 proteins.

DETAILED DESCRIPTION

Figure 1:
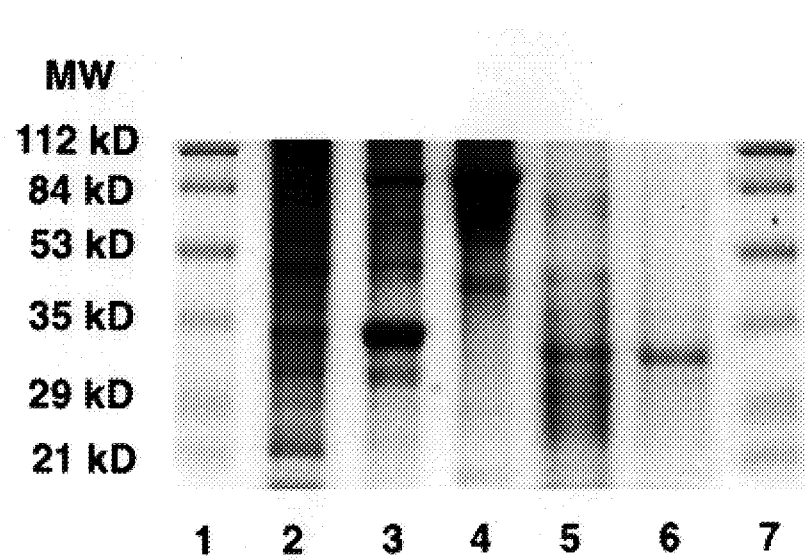
FIG. 1. SDS-PAGE analysis of the purification fractions. Lanes 1 and 7 contain molecular weight markers. Lanes 2–5 contain Fractions I–IV respectively (described in the text and Table 1). Lane 6 contains material from ssDNA cellulose column fraction 17, which was then pooled with fractions 15 and 16 to yield Fraction V.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "DNA repair modulator", "endonuclease III", "DNA glycosylase/AP lyase" and any variants not specifically listed, may be used herein interchangeably, and as used throughout the present application and claims refer to proteinaceous material including single or multiple proteins, and extends to those proteins having the amino acid sequence data described herein and presented in FIG. 7, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "DNA repair modulator", "endonuclease III" and "DNA glycosylase/AP lyase" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.,* 243:3552–59 (1969), abbreviations for amino acid residues are shown in the following Table of Correspondence:

TABLE OF CORRESPONDENCE

SYMBOL

| 1-Letter | 3-Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A nucleic acid molecule is "hybridizable" to another nucleic acid molecule such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides, preferably at least about 15 nucleotides; and more preferably the length is at least about 20 nucleotides; and most preferably 30 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package. Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

GENES ENCODING ENDONUCLEASE III PROTEINS

As illustrated in the Examples herein, the present invention includes the isolation of a gene encoding an endonuclease III of the invention, including a full length, or naturally occurring form of endonuclease III, and any antigenic fragments thereof from any animal, particularly mammalian, and more particularly human. source. As used herein, the term "gene" refers to an assembly of nucleotides that encode a polypeptide, and includes cDNA and genomic DNA nucleic acids.

A gene encoding endonuclease III, whether genomic DNA or cDNA, can be isolated from any source, particularly from a human cDNA or genomic library. Methods for obtaining endonuclease III gene are well known in the art, as described above (see, e.g., Sambrook et al., 1989, supra).

Accordingly, any animal cell potentially can serve as the nucleic acid source for the molecular cloning of an endonuclease III gene. The DNA may be obtained by standard procedures known in the art from cloned DNA (e.g., a DNA "library"), and preferably is obtained from a cDNA library prepared from tissues with high level expression of the protein (e.g., a spleen cDNA library, as described herein), by chemical synthesis, by cDNA cloning, or by the cloning of genomic DNA, or fragments thereof, purified from the desired cell (See, for example Sambrook et al., 1989, supra; Glover, D. M. (ed.), 1985, DNA Cloning: A Practical Approach, MRL Press, Ltd., Oxford, U. K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired endonuclease III gene may be accomplished in a number of ways. For example, if an amount of a portion of an endonuclease III gene or its specific RNA, or a fragment thereof, is available and can be purified and labeled, the generated DNA fragments may be screened by nucleic acid hybridization to a labeled probe [Benton and Davis, Science, 196:180 (1977); Grunstein and Hogness, Proc. Natl. Acad. Sci. U.S.A., 72:3961 (1975)]. For example, a set of oligonucleotides corresponding to the partial amino acid sequence information obtained for the endonuclease III protein can be prepared and used as probes for DNA encoding endonuclease III, or as primers for cDNA or mRNA (e.g., in combination with a poly-T primer for RT-PCR). Preferably, a fragment is selected that is highly unique to endonuclease III of the invention. Those DNA fragments with substantial homology to the probe will hybridize. As noted above, the greater the degree of homology, the more stringent hybridization conditions can be used. In a specific embodiment, stringency hybridization conditions are used to identify a homologous endonuclease III gene.

An endonuclease III gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified endonuclease III DNA, or may be synthetic oligonucleotides designed from the partial amino acid sequence information. Immunoprecipitation analysis or functional assays (thymine glycol-DNA glycosylase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against endonuclease III, such as the rabbit polyclonal anti-murine endonuclease III antibody described herein.

A radiolabeled endonuclease III cDNA can be synthesized using the selected mRNA (from the adsorbed polysomes) as a template. The radiolabeled mRNA or cDNA may then be used as a probe to identify homologous endonuclease III DNA fragments from among other genomic DNA fragments.

The present invention also relates to cloning vectors containing genes encoding analogs and derivatives of endonuclease III of the invention, that have the same or homologous functional activity as endonuclease III, and homologs thereof from other species. The production and use of derivatives and analogs related to endonuclease III are within the scope of the present invention. In a specific embodiment, the derivative or analog is functionally active, i.e., capable of exhibiting one or more functional activities associated with a full-length, wild-type endonuclease III of the invention.

Endonuclease III derivatives can be made by altering encoding nucleic acid sequences by substitutions, additions or deletions that provide for functionally equivalent molecules. Preferably, derivatives are made that have enhanced or increased functional activity relative to native endonuclease III. Alternatively, such derivatives may encode soluble fragments of endonuclease III extracellular domain that have the same or greater affinity for the natural ligand of endonuclease III of the invention. Such soluble derivatives may be potent inhibitors of ligand binding to endonuclease III.

Due to the degeneracy of nucleotide coding sequences, other DNA sequences which encode substantially the same amino acid sequence as an endonuclease III gene may be used in the practice of the present invention. These include but are not limited to allelic genes, homologous genes from other species, and nucleotide sequences comprising all or portions of endonuclease III genes which are altered by the substitution of different codons that encode the same amino acid residue within the sequence, thus producing a silent change. Likewise, the endonuclease III derivatives of the invention include, but are not limited to, those containing, as a primary amino acid sequence, all or part of the amino acid sequence of an endonuclease III protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained: and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding endonuclease III derivatives and analogs of the invention can be produced by various methods known in the art. The manipulations which result in their production can occur at the gene or protein level. For example, the cloned endonuclease III gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of endonuclease III, care should be taken to ensure that the modified gene remains within the same translational reading frame as the endonuclease III gene, uninterrupted by translational stop signals, in the gene region where the desired activity is encoded.

Additionally, the endonuclease III-encoding nucleic acid sequencecan be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated endonuclease III gene product. Any technique for mutagenesis known in the art can be used, including but not limited to, in vitro site-directed mutagenesis [Hutchinson, C., et al., *J. Biol. Chem.*, 253:6551 (1978); Zoller and Smith, DNA, 3:479–488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

EXPRESSION OF ENDONUCLEASE III POLYPEPTIDES

The nucleotide sequence coding for endonuclease III, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding endonuclease III of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding endonuclease III and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant endonuclease III protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell containing the recombinant vector comprising the nucleic acid encoding endonuclease III is cultured in an appropriate cell culture medium under conditions that provide for expression of endonuclease III by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of endonuclease III protein may be controlled by any promoter/enhancer element known in the art, but these regulatory elements must be functional in the host selected for expression. Promoters which may be used to control endonuclease III gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982. Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan. 1985, Nature 315:115–122), iminunoglobulin gene control region which is active in lymphoid cells (Grosschedl et al., 1984, Cell 38:647–658; Adames et al., 1985, Nature 318:533–538: Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding an endonuclease III of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding endonuclease III is inserted within the "selection marker" gene sequence of the vector, recombinants containing the endonuclease III insert can be identified by the absence of the endonuclease III gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, Gene 67:31–40), pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoRI, NotI, XmaIII, BglIII, and PstI cloning site; Invitrogen), pVL1392 (BglII, PstI, NotI, XmaIII, EcoRI, Xbal, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglIII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express the endonuclease III protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gull, or a DNA vector transporter (see, e.g., Wu et al., 1992, J. Biol. Chem. 267:963–967; Wu and Wu, 1988, J. Biol. Chem. 263: 14621–14624; Hartmut et al., Canadian Patent Application No. 2,012,311, filed Mar. 15, 1990).

In a specific embodiment, an endonuclease III fusion protein can be expressed. An endonuclease III fusion protein comprises at least a functionally active portion of a non-endonuclease III protein joined via a peptide bond to at least a functionally active portion of an endonuclease III polypeptide. The non-endonuclease III sequences can be amino- or carboxy-terminal to the endonuclease III sequences. More preferably, for stable expression of a proteolytically inactive endonuclease III fusion protein, the portion of the non-endonuclease III fusion protein is joined via a peptide bond to the amino terminus of the endonuclease III protein. A recombinant DNA molecule encoding such a fusion protein comprises a sequence encoding at least a functionally active portion of a non-endonuclease III protein joined in-frame to the endonuclease III coding sequence, and preferably encodes a cleavage site for a specific protease, e.g., thrombin or Factor Xa, preferably at the endonuclease III-non-endonuclease III juncture. In a specific embodiment, the fusion protein is expressed in *Escherichia coli*. In one preferred embodiment a glutathione S-transferase (GST)-endonuclease III fusion protein is prepared as described in Example 3, herein.

GENERAL PROTEIN PURIFICATION PROCEDURES

Initial steps for purifying the mammalian endonuclease III polypeptides of the present invention include salting in or salting out, such as in ammonium sulfate fractionations; solvent exclusion fractionations, e.g., an ethanol precipitation; detergent extractions to free membrane bound proteins using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) Sephadex or cellulose; or with a cation exchanger such as carboxymethyl (CM) or sulfopropyl (SP) Sephadex or cellulose. Alternative means of solid phase binding includes the exploitation of hydrophobic interactions e.g., the using of a solid support such as phenylSepharose and a high salt buffer; affinity-binding, using, e.g., placing a substrate analog on an activated support; immuno-binding, using e.g., an antibody to the endonuclease III bound to an activated support; as well as other solid phase supports including those that contain specific dyes or lectins etc. A further solid phase support technique that is often used at the end of the purification procedure relies on size exclusion, such as Sephadex and Sepharose gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate. monophosphate and diphosphate. The Good buffers [Good, N. E., et al., (1966) Biochemistry, 5, 467; Good, N. E. and Izawa, S., (1972) Meth. Enzymol., 24, Part B, 53; and Fergunson, W. J. and Good, N. E., (1980) Anal. Biochem. 104, 300.] such as Mes, Hepes, Mops, tricine and Ches. Materials to perform all of these techniques are available from a variety of sources such as Sigma Chemical Company in St. Louis, Mo.

Specific purification procedures for the endonulease III polypeptide is exemplified in Example 1, and for the corresponding fusion protein in Example 3.

ANTIBODIES TO THE ENDONUCLEASE III

According to the invention, endonuclease III produced recombinantly, from natural sources or by chemical synthesis, and fragments or other derivatives or analogs thereof, including fusion proteins, may be used as an immunogen to generate antibodies that recognize the endonuclease III polypeptide. Such antibodies include but are not limited to polyclonal, monoclonal, chimeric, single chain, Fab fragments, and an Fab expression library. The anti-endonuclease III antibodies of the invention may be cross reactive, e.g., they may recognize endonuclease III from different mammalian species. Polyclonal antibodies have greater likelihood of cross reactivity. Alternatively, an antibody of the invention may be specific for a single form of endonuclease III, such as rat endonuclease III. Preferably, such an antibody is specific for human endonuclease III.

Various procedures known in the art may be used for the production of polyclonal antibodies to endonuclease III or derivative or analog thereof. For the production of antibody, various host animals can be immunized by injection with the endonuclease III, or a derivative (e.g., fragment or fusion protein) thereof, including but not limited to rabbits, mice, rats, sheep, goats, etc. In one embodiment, the endonuclease III polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the endonuclease III, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy,* Alan R. Liss, Inc., pp.77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an endonuclease III together with genes from a human antibody molecule of appropriate biological activity can be used; such antibodies are within the scope of this invention. Such human or humanized chimeric antibodies are preferred for use in therapy of human diseases or disorders, since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce mammalian endonuclease III polypeptide-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an endonuclease III polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an endonuclease III polypeptide, one may assay generated hybridomas for a product which binds to an endonuclease III polypeptide fragment containing such epitope. For selection of an antibody specific to an endonuclease III polypeptide from a particular mammalian species of animal, one can select on the basis of positive binding with endonuclease III polypeptide expressed by or isolated from cells of that species of mammal.

The foregoing antibodies can be used in methods known in the art relating to the localization and activity of the endonuclease III polypeptide, e.g., for Western blotting, imaging endonuclease III polypeptide in situ, measuring levels thereof in appropriate physiological samples, etc. using any of the detection techniques mentioned above or known in the art. In a specific embodiment antibodies that agonize or antagonize the activity of mammalian endonuclease III polypeptide can be generated.

ANTISENSE AND RIBOZYMES AGAINST ENDONUCLEASE III

The present invention extends to the preparation of antisense nucleotides and ribozymes that may be used to interfere with the expression of mammalian endonuclease III at the translational level. This approach utilizes antisense nucleic acid and ribozymes to block translation of a specific mRNA, either by masking that mRNA with an antisense nucleic acid or cleaving it with a ribozyme. Such methods can be used in preparing cells and/or organisms that lack functional endonuclease III.

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., *J. Exp. Med.* 168:1237 (1988)]. Preferably synthetic antisense nucleotides contain phosphoester ananalogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding the endonuclease III described and enabled herein may thus be used to prepare antisense molecules (which block transcription of mRNA encoding endonuclease III) and ribozymes (that cleave mRNAs for the endonuclease III) thus inhibiting expression of the gene encoding the endonuclease III which thereby reduces the level endonuclease III in a target mammalian cell.

LABELS

An endonuclease III of the present invention, including a full length, or naturally occurring form of endonuclease III, and any antigenic fragments thereof from any animal, particularly mammalian and more particularly a human source can be labeled. In addition, antibodies to the endonuclease III of the present invention, and nucleic acids that encode mammalian endonuclease III or fragments thereof, and probes that hybridize to such nucleic acids can also be labeled.

Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (Application No. 89311108.8) to Pestka, or U.S. Pat. No. 5,459,240, issued Oct. 17, 1995 to Foxwell et al.

As exemplified herein, proteins, including an endonuclease III of the present invention and antibodies thereto, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthphosphate. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions).

ADMINISTRATION

According to the invention, the component or components of a therapeutic composition of the invention may be introduced parenterally, transmucosally, e.g., orally, nasally, or rectally, or transdernally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of endonuclease III is indicated to act to repair DNA damage and/or as a tumor suppressor of a tumor, it may be introduced by injection into the tumor or into tissues surrounding the tumor.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.). Liss: New York, pp. 353–365 (1989); Lopez-Berestein, ibid., pp. 317–327; see generally ibid.]. To reduce its systemic side effects, this may be a preferred method for introducing endonuclease III.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. facromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, supra, vol. 2, pp. 115–138 (1984)]. Preferably, a controlled release device is introduced into a subject in proximity of the site of inappropriate immune activation or a tumor.

Other controlled release systems are discussed in the review by Langer [*Science* 249:1527–1533 (1990)].

In a further aspect, recombinant cells that have been transformed with the endonuclease III gene and that express high levels of the polypeptide can be transplanted in a subject in need of endonuclease III polypeptide. Preferably autologous cells transformed with endonuclease III are transplanted to avoid rejection; alternatively, technology is available to shield non-autologous cells that produce soluble factors within a polymer matrix that prevents immune recognition and rejection.

Thus, the endonuclease III polypeptide can be delivered by intravenous, intraarterial, intraperitoneal, intramuscular, or subcutaneous routes of administration. Alternatively, the endonuclease III polypeptide, properly formulated, can be administered by nasal or oral administration. A constant supply of endonuclease III can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of endonuclease III is an effective therapeutic regimen for an dysproliferative disease is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Turning now to the specific aspects of the experiments that resulted in the discovery of the present invention, the purification of a mammalian endonuclease III-like enzyme from calf thymus was undertaken by monitoring its DNA glycosylase activity against UV induced pyrimidine hydrates. The assay measures release of [$^3$H]-labeled pyrimidine hydrates and is reproducible and linear with respect to time and protein concentration. The substrate is easily prepared and, most importantly, the chemical identity of the enzymatically released photoproducts can be corroborated by HPLC analysis. Calf thymus was chosen as the source of enzyme because it contains endonuclease III-like activity and because large amounts of very fresh tissue are available.

A novel approach to the definitive identification of the mammalian enzyme was the application of a chemical reaction which results in the irreversible cross linking of the enzyme to its DNA substrate. N-acylimine (Schiff's base) enzyme substrate (ES) intermediates are characteristic of the prokaryotic DNA glycosylase/AP lyases described to date. Such intermediates can be irreversibly stabilized through chemical reduction to secondary amines. In such a way T4 endonuclease V (Dodson et al., 1993), and the *E. coli* Fpg protein (Tchou and Grollman, 1995) were irreversibly cross-linked to substrate oligodeoxynucleotides containing a cyclobutane dimer, and an 8-oxoguanine residue, respectively. The reductive cross linking of enzyme to an oligodeoxynucleotide permits identification of the mammalian protein by two experimental parameters. The first is an increase in the apparent molecular mass of the enzyme as determined by SDS-PAGE. Second, if the oligodeoxynucleotide is 5'-end labeled with $^{32}$P, the irreversibly cross linked protein-DNA complex can be detected by autoradiography or phosphorimaging after SDS-PAGE.

On the basis of the results obtained with endonuclease V and the Fpg protein we anticipated successful irreversible cross linking of *E. coli* endonuclease III to an oligodeoxynucleotide containing one of the enzyme's known substrates, thymine glycol. Assuming that the mammalian enzyme also functions through a N-acylimine ES intermediate, we could then apply the reductive cross linking reaction to the purified mammalian enzyme fractions using the same oligodeoxynucleotide. This would permit isolation of the correct protein species from a SDS-polyacrylamide gel in sufficient amount for primary amino acid sequencing.

EXAMPLE 1

Experimental Procedures

Buffers. Homogenization Buffer: 25 mM HEPES, pH 7.5, 15 mM NaCl, 1 mM DTT, 2 mM EDTA, 0.5 mg/mL Leupeptin, 0.7 mg/mL Pepstatin, 0.2 mM phenylmethylsulfonyl flouride. HDE: 25 mM HEPES, pH 7.5, 1 mM DTT, 2 mM EDTA.

Enzyme. *E. coli* endonuclease III was purified from *E. coli* strain UC6444 carrying the plasmid pHIT1 as previously described [Asahara, et al., *Biochemistry*, 28:4444–4449 (1989)].

Radionucleotides. [5,5'-$^3$H] deoxycytidine-5'-triphosphate (15–30 Ci/mmol) and [methyl-$^3$H]-thymidine-5'-triphosphate (70–90 Ci/mmol) were purchased from Du Pont/NEN).

Oligodeoxynucleotides. Alternating poly(dG-dC) and poly(dA-dT) were purchased from Pharmacia.

Purification of a Pyrimidine Hydrate DNA-glycosylase from Calf Thymus. All purification procedures were carried out at 4° C., unless otherwise indicated. 1.2 kg of freshly obtained calf thymus was homogenized in a Waring Blendor in 4.8 L of homogenization buffer and further fragmented by sonication in 300 mL aliqots for 3 min at 70% power using a Heat Systems model W-375 sonicator equipped with a model 305 high gain horn. 4M NaCl was added to a final concentration of 320 mM and the gelatinous precipitate removed manually by spooling using a 10 mL glass pipette as a stirring rod. The remaining solution was cleared by centrifugation at 10,000×g, filtered through cheesecloth and diluted with 1.7 volumes of HDE to produce Fraction I (4000 ml).

Fraction I was batch extracted with 450 ml (packed volume) of cation exchange resin (SP Fast-flow, Pharmacia) pre-equilibrated with HDE containing 150 mM NaCl. After the beads settled the supernatant was discarded and the beads poured into an XK 26/60 column (Pharmacia). They were washed with 500 ml of HDE containing 150 mM NaCl, followed by a 2 L gradient from 150–700 mM NaCl at 4 ml/min. Twenty ml column fractions were collected and assayed. Fractions 45–75 were pooled to yield Fraction II (620 ml).

Solid ammonium sulfate was added to Fraction II, which contained approximately 350 mM NaCl, to a final saturation of 21% (120 g/l solution). The sample was centrifuged at 12,000×g for 20 min to remove precipitate and the supernatant applied to a C 26/40 column (Pharmacia). containing 150 mL (bed volume) of Octylsepharose 4 Fast-flow media (Pharmacia) pre-equilibrated with HDE, 21% ammonium sulfate, 300 mM NaCl. The column was washed with 150 ml of HDE, 21% ammonium sulfate, 300 mM NaCl followed by a 1.5 L gradient beginning with HDE, 21% ammonium sulfate, 300 mM NaCl and finishing with HDE containing neither ammonium sulfate nor NaCl at 3 mL/min, collected in 20 mL fractions. One mL aliquots of the column fractions were dialyzed into HDE, 125 mM NaCl, and assayed for enzymatic activity. Active fractions (31–44) were pooled and dialyzed into HDE, 125 mM NaCl (Fraction III, 280 mL).

Fraction III was concentrated by loading onto an HR 10/10 Mono S column (Pharmacia) and eluting via a step increase in NaCl concentration to HDE, 0.5M NaCl. One mL fractions were collected and assayed and 12 active fractions were pooled. The 12 mL sample was divided into 3×4 mL aliquots each of which were fractionated via gel filtration chromatography through a Hiload 26/60, Superdex 75 pg column (Pharmacia), run in HDE, 350 mM NaCl (2.5 mL/min) and collected in 2.5 mL fractions. The gel filtration column was pre-calibrated with the Gel Filtration Low Molecular Weight Calibration Kit from Pharmacia. Active fractions (70–75, Mr=approximately 29 kD) from each of 3 column runs were pooled to 45 mL which was diluted from 350 mM NaCl to 125 mM NaCl with 1.8 volumes of HDE. The sample was then loaded onto a HR 5/5 MonoS column (Pharmacia) and concentrated via step elution with HDE, 0.5M NaCl. Enzymatic activity eluted in six 0.5 mL fractions which were pooled to yield Fraction IV (3 mL).

Fraction IV was diluted to 100 mM NaCl with 4 volumes of HDE, loaded onto a 1 mL single stranded DNA-cellulose (ssDNA-cellulose, Sigma) HR 5/5 column (Pharmacia) and eluted with a 12.5 mL gradient (100–600 mM NaCl) (0.2 mL/min). Fractions 15–17 were pooled to yield Fraction V (1.5 mL).

Preparation of Substrates for DNA-Glycosylase Assays. Poly(dG-[$^3$H]dC) was produced as described previously [Boorstein. et al., 1989, supra], by nick translation of Poly (dG-dC) (Pharmacia) with [5,5'-$^3$H]dCTP (Du Pont/NEN), and purified using Nick-Spin columns (Pharmacia). Poly (dG-[$^3$H]dC) produced in this manner had a specific activity of 1.2×10$^6$ cpm/ug. This DNA was then exposed to 400 kJ/m$^2$ of UV radiation at 254 nm (two 15 Watt germicidal bulbs) to induce the formation of cytosine hydrate. UV flux was quantitated using a UVX 54 radiometer (UVP Inc., San Gabriel, Calif.).

Poly(dA-[$^3$H]dT was produced by the nick-translation of Poly (dA-dT) with [methyl-$^3$H]dTTP, followed by oxidation of the alternating copolymer with osmium tetroxide to form thymine glycol residues [Higgins, et al, 1987, supra]. The radiolabeled, oxidized DNA was purified by passing it twice through Nick-Spin columns (Pharmacia). Thyinine glycol-containing poly(dA-[$^3$H]dT) produced in this manner had a specific activity of approximately 7×10$^6$ cpm/ug.

DNA-Glycosylase Assays. Pyrimidine hydrate and thyinine glycol DNA-glycosylase assays were carried out against UV-irradiated and oxidized DNA substrates respectively, as follows: enzyme aliquots were incubated with 0.1 ug of substrate DNA in a reaction mixture containing 15 mM HEPES, pH 7.5, 75 mM NaCl, 10 mM EDTA, and 1 mM DTT in a volume of 60 uL for specified periods of time up to 3 h at 37° C. Reactions were terminated by the addition of 25 uL of 25 mg/mL BSA and 2 mL acetone, which precipitated both the protein and DNA, leaving in solution only the free modified bases which had been enzymatically cleaved from the DNA backbone. After centrifugation, at 8000×g for 15 min the supernatant was dried, resuspended in water and analyzed by liquid scintillation counting. At each step the chemical identity of the released radioactive product was proven to be cytosine by HPLC. The free cytosine hydrate released by the enzyme is unstable, rapidly eliminating water, and is recovered as free cytosine (Boorstein et al., 1989). One unit of enzyme released 1 pmole of cytosine hydrate from 0.1 ug of UV-irradiated poly(dG-[$^3$H]dC) in 1 min. Enzyme assays lasted from 15 min to 3 h, depending upon the specific activity of the enzyme during the different phases of the purification.

[$^3$H]Thymine glycol released from the oxidized poly(dA-[$^3$H]dT) was identified by HPLC as previously described [Higgins, et al., 1987, supra].

AP nicking assay. AP-site containing DNA was prepared and nicking activity assayed as described previously [Cunningham, et al., 1985, supra]. The assay is done in 10 mM EDTA to preclude any $Mg^{++}$- dependent AP endonuclease from acting on the substrate.

Preparation of Thymine Glycol-containing Oligodeoxynucleotide for Cross Linking Studies. Thymine glycol-containing single stranded oligodeoxynucleotide was prepared as described previously [Kao, et al., J. Biol. Chem., 268:17787–17793 (1993)]. The oxidation was carried out on 50 $OD_{260}$ of d(CGCGATACGCC) (SEQ ID NO:5). The complementary 11 mer was synthesized by conventional means.

Cross linking of Enzyme to Oligodeoxynucleotide. Twenty pmoles of the appropriate oligodeoxynucleotide, either thymine glycol-containing or complementary, was 5'-end labeled using T4 kinase (Gibco BRL) and [$^{32}P$] γ-ATP, according to the manufacturer's recommendations, and purified using a Nuc Trap Push Column (Stratagene) pre-equilibrated in 20 mM HEPES, pH 7.5, 50 mM NaCl, 5 mM EDTA. The radiolabeled oligodeoxynucleotide was then combined with 200 pmoles of non-radioactive oligodeoxynucleotide, and the complementary strand added at a 1:1 ratio and placed on ice for 30 min. Enzyme was reacted with the substrate double-stranded oligodeoxynucleotide in a total volume of 300 uL under the following reaction conditions: 37.3 mM $NaCNBH_3$, 20 mM HEPES, pH 7.5. 46.5 m M KCl, 5 mM EDTA, 1.5 uM oligodeoxynucleotide, 15 ng/uL protein. In the case of E. coli endonuclease III, this represented a 4 fold molar excess of substrate oligodeoxynucleotide to enzyme. After incubation at 37° C. for 2 h, samples were quick frozen on dry ice, lyophilized, resuspended and boiled in 35 uL of 1× SDS-PAGE loading buffer, and separated by electrophoresis on a 15% Tricine-SDS gel. Following electrophoresis, the gel was stained with Coomassie Blue, wrapped in plastic, and analyzed via phosphorimaging.

Gel Electrophoresis. All samples were lyophilized to dryness, and resuspended in standard SDS loading buffer prior to electrophoresis. Fifteen percent Tricine gels were prepared [Shagger, et al., Anal. Biochem., 166:368–379 (1987)] and run using the Mini-Protein II electrophoresis system (Bio-Rad). Gels were run at 90 V for approximately 5 h, completion being determined by the progress of pre-stained low molecular weight electrophoresis standards (Bio-Rad). Gels were then stained with Coomassie Blue.

Amino acid sequence analysis. Fractions from the ssDNA cellulose column (Fraction V) were run on a 15% Tricine-SDS gel and stained with Coomassie Blue. The predominant band, identical to the band which shifted after reductive coupling to the thymine glycol-containing oligodeoxynucleotide, was excised from the gel and sent to the W. M. Keck Foundation microsequencing facility at Yale University, New Haven, Conn.

At Yale, the protein was subjected to proteolytic digestion followed by purification on HPLC using a reverse phase microbore C 18 column. Individual peaks were assayed for purity by laser desorption mass spectroscopy. After a 16 h hydrolysis, amino acid analysis was carried out on a Beckman Model 6300 ion-exchange instrument [Rosenfeld, et al., Anal. Biochem., 203:173–179 (1992). Elliott, et al., Anal. Biochem., 211:94–101 (1993); Williams and Stone, Techniques in Protein Chemistry VI, 143–152 (1995); Williams, et al., Protein Protocol Handbook, (1995)].

The sequence homologies were obtained via the BLAST [Altschul, et al., J. Mol. Biol., 215:403–410 (1990)] Network Service of the National Center for Biotechnology Information which accesses the Brookhaven, Swiss, PIR and GenBank data bases.

RESULTS

Purification of the mammalian enzyme. A mammalian homologue of E. coli endonuclease III was purified from fresh calf thymus on the basis of its pyrimidine hydrate DNA-glycosylase activity. After the final purification step, ssDNA-cellulose chromatography, the enzyme was purified approximately 5,000-fold as estimated by the specific activity of the pyrimidine hydrate DNA-glycosylase and the yield was approximately 1%. This is set forth in Table 1, below, and in FIG. 1.

TABLE 1

Summary of Purification of a Pyrimidine Hydrate DNA-Glycosylase from Calf Thymus*

| fraction | total protein (mg) | volume (mL) | total activity (pmol/min) | specific activity [pmol/ (min-mg)] | purification (fold) | yield (%) |
| --- | --- | --- | --- | --- | --- | --- |
| I | 52000 | 4000 | 2920 | 0.056 | | |
| II | 2420 | 720 | 1020 | 0.421 | 7.5 | 34.9 |
| III | 264 | 350 | 370 | 1.40 | 25 | 12.7 |
| IV | 1.3 | 3.0 | 36 | 27.7 | 495 | 1.2 |
| V | 0.1 | 1.5 | 29 | 290 | 5180 | 1.0 |

*Purification steps and fractions are described in the text.

Figure 2A:
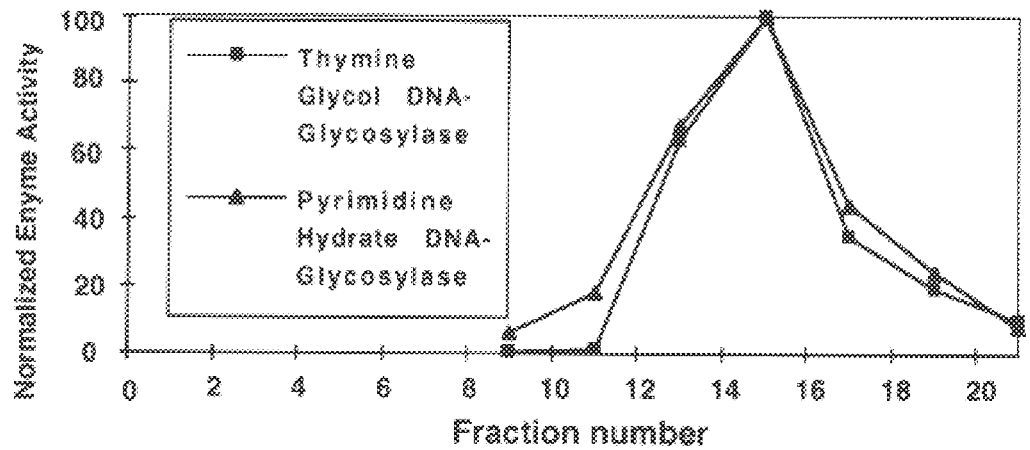
FIG. 2A. Coelution of pyrimidine hydrate and thymine glycol DNA-glycosylase activities from the ssDNA cellulose column. Fractions from the ssDNA cellulose column were assayed simultaneously for both enzyme activities. Activities were normalized by dividing the activity of each fraction by the activity of the fraction with maximum activity.

Co-elution of DNA-glycosylase activities. Successive fractions from the ssDNA-cellulose column were assayed simultaneously for pyrimidine hydrate and thymine glycol DNA-glycosylase activities, both of which have been demonstrated for endonuclease III [Higgins, et al., 1987, supra Boorstein, et al., 1989, supra]. FIG. 2A documents the coelution of the two activities.

Figure 2B:
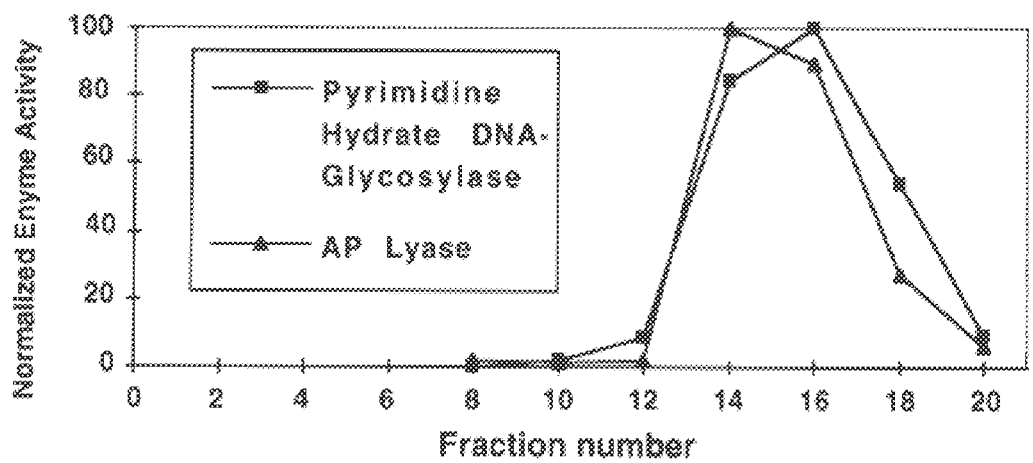
FIG. 2B. Coelution of pyrimidine hydrate DNA glycosylase activity and AP lyase activity from the ssDNA cellulose column. A second calf thymus preparation was purified through ssDNA cellulose, and elution fractions analyzed for both enzyme activities, normalized as in FIG. 2A.

Co-elution of DNA-glycosylase and Mg++-Independent AP Site Nicking Activity. Comparable ssDNA-cellulose purified material from another calf thymus preparation was assayed simultaneously for $Mg^{++}$-independent AP-nicking activity and pyrimidine hydrate DNA-glycosylase activity, both of which are also previously documented activities of E. coli endonuclease III [Cunningham, et al., 1985, supra]. The coelution of these two activities is shown in FIG. 2B.

Figure 2C:
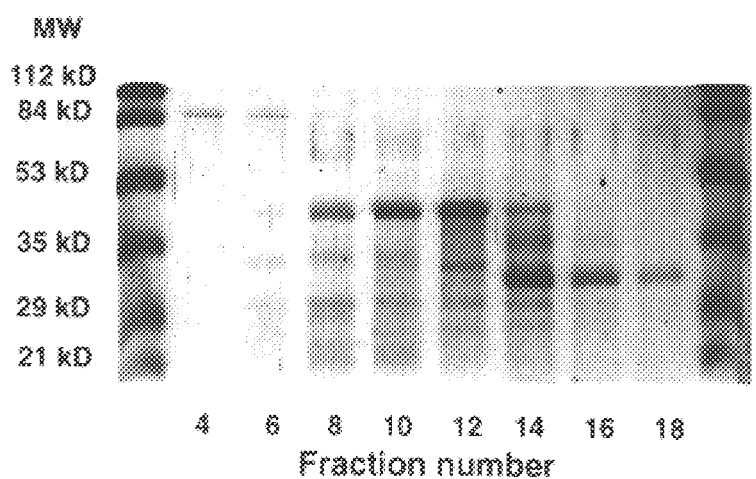
FIG. 2C. SDS-PAGE analysis of ssDNA cellulose elution fractions (Fraction V). A 25 uL aliquot from each of the indicated fractions shown in 2A was analyzed by SDS-PAGE. Fractions 14–18 contain the predominant 31 kD species. The extreme left and right lanes contain molecular weight markers.

Estimation of the Molecular Weight of the Mammalian Enzyme. The molecular radius of the mammalian DNA-glycosylase, as determined by gel filtration, was approximately 29 kD. Although ssDNA-cellulose fractions with peak enzymatic activity contained more than 1 protein species, a predominant band of apparent molecular mass of 31 kD was present on SDS-PAGE analysis. Moreover, when 25 uL aliquots of successive ssDNA-cellulose column fractions, were subjected to electrophoresis and stained with Coomassie Blue, the elution profile of this predominant 31 kD species, as judged by the intensity of staining, corresponded to that of the two DNA-glycosylase activities (FIG. 2C).

Figure 3A:
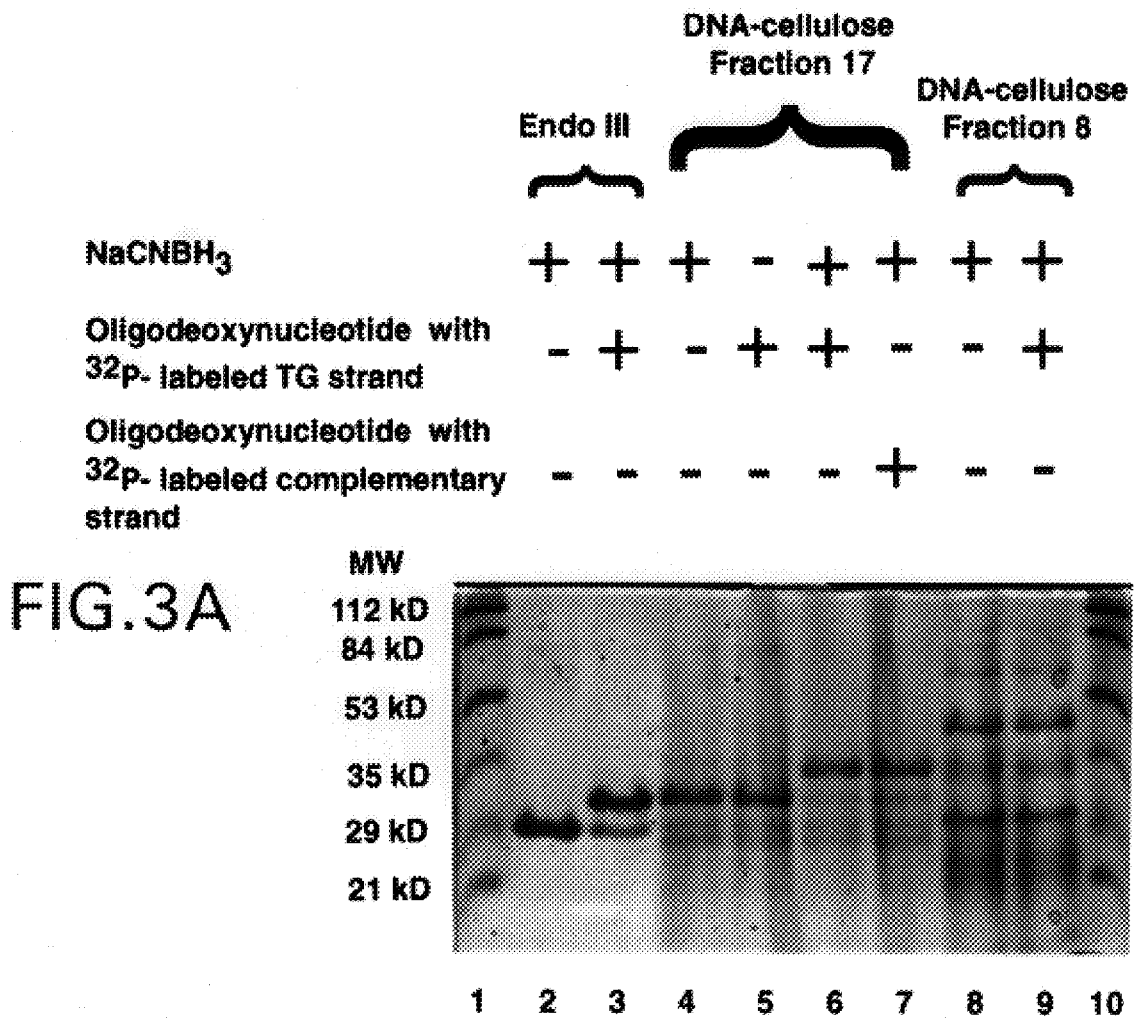
FIG. 3A. SDS-PAGE analysis of $E.$ $coli$ endonuclease III and the bovine enzyme after incubation with the thymine glycol-containing oligodeoxynucleotide and $NaCNBH_3$. Lanes 1 and 10 contain molecular weight markers. Lane 2 contains the product of the reaction of $E.$ $coli$ endonuclease III and $NaCNBH_3$. Lane 3 contains the product of the same reaction mixture as Lane 2 with addition of duplex $5'-^{32}P$ labeled oligodeoxynucleotide containing a single thymine glycol (TG) residue. Lane 4 contains the product of fraction 17 eluted from the ssDNA cellulose column and incubated with $NaCNBH_3$ but no oligodeoxynucleotide. Lane 5 contains the product of elution fraction 17 incubated with the $5'-^{32}P$-oligodeoxynucleotide but no $NaCNBH_3$. Lane 6 contains the product of elution fraction 17 incubated with both the oligodeoxynucleotide and $NaCNBH_3$. Lane 7 is the same mixture as 6 except that the complementary (non-thymine glycol-containing) oligodeoxynucleotide was 5' labeled with $^{32}P$. Lanes 8 and 9 contain the products of the incubation of ssDNA-cellulose fraction 8, which did not exhibit enzymatic activity, alone or with oligodeoxynucleotide and $NaCNBH_3$, respectively.

Reductive Cross Linking of the Enzymes to a Thymine Glycol-Containing DNA Oligodeoxynucleotide. Incubation of purified E. coli endonuclease III with duplex DNA, (the thymine glycol-containing oligodeoxynucleotide annealed to its complementary strand) in the presence of $NaCNBH_3$ resulted in an increase in the apparent molecular mass of the enzyme as determined by SDS-PAGE (FIG. 3A). Lane 2 demonstrates endonuclease III incubated with substrate DNA in the absence of $NaCNBH_3$ and Lane 3 in the presence of NaCNBH$_3$. The increase in the apparent molecular mass of the endonuclease III is the result of irreversible cross linking of the enzyme to the oligodeoxynucleotide.

The reductive cross linking reaction was also performed on the most purified preparation of the calf thymus pyrimidine hydrate DNA-glycosylase. A 75 uL aliquot of fraction 17 eluted from the ssDNA cellulose column (FIG. 2A) containing purified enzyme of maximal specific activity, was incubated with the thymine glycol-containing oligodeoxynucleotide in the presence of NaCNBH$_3$ along with appropriate controls. Lanes 4 and 5 represent ssDNA fraction 17 incubated with NaCNBH$_3$ and no substrate DNA and substrate DNA in the absence of NaCNBH$_3$ respectively. The apparent molecular mass of 31 kD, as first shown in FIG. 2C, did not change under either of these incubations. However, when the reaction mixture contained both substrate DNA and NaCNBH$_3$, the predominant 31 kD Coomassie Blue-stained band shifted to an apparent molecular mass of 35 kD, as shown in lanes 6 and 7. As an additional control, Fraction 8 eluting from the ssDNA cellulose column (FIG. 2A), which contained no enzymatic activity, was also exposed to the conditions of the coupling reaction. Lanes 8 and 9 of FIG. 3A contain protein from this fraction incubated with the oligodeoxynucleotide in the presence or absence of NaCNBH$_3$. As can readily be seen, no shift of the visible protein bands occurred.

Figure 3B:
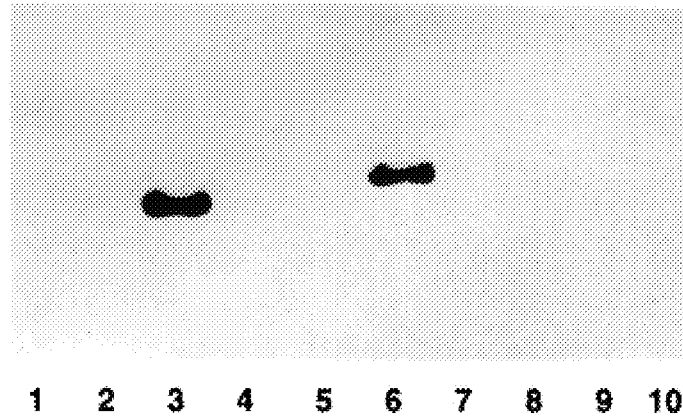
FIG. 3B. Phosphorimage of the SDS-PAGE gel of FIG. 3A. The lanes are identical to those of Panel A.

Additional proof of irreversible cross linking is demonstrated in FIG. 3B. The thymine glycol-containing oligodeoxynucleotide had been 5'-end-labeled with $^{32}$P prior to the coupling reactions. A phosphorimage of the gel in FIG. 3A demonstrated only 2 bands. FIG. 3B shows a single band in lane 3 which corresponds to the position of the shifted cross linked endonuclease III. The single band in lane 6 corresponds to the position of the predominant Coomassie-Blue stained species from calf thymus, which had also shifted after cross linking. Under the denaturing conditions (boiling) used to prepare samples for the SDS gel, the complementary oligodeoxynucleotide strand does not remain associated with the protein. When the complementary, rather then the thymine glycol-containing oligodeoxynucleotide was $^{32}$P-labeled, the protein shifted (FIG. 3A, lane 7), but did not appear on the phosphorimage (FIG. 3B, lane 7). Thus, lanes 6 and 7 of FIG. 3B prove that the bovine enzyme cross linked only to the oligodeoxynucleotide containing the thymine glycol residue, thereby confirming that the irreversible cross linking resulting from chemical reduction is exclusively dependent upon formation of a specific ES intermediate. There was no evidence of any binding of oligodeoxynucleotide to the proteins which did not contain enzyme activity, further corroborating that the reductive cross linking reaction was absolutely specific.

Amino Acid Sequence Data. Four peptides derived from a proteolytic digest of the purified bovine protein were sequenced yielding sequences of 14, 15, 22 and 23 amino acids. None of these sequences demonstrated direct similarity to E. coli endonuclease III by initial BLAST analysis. However, the 22 amino acid peptide sequence demonstrated considerable similarity to a portion of two predicted full length protein sequences from C. elegans (Acc. no. Z05874) [Wilson, et al., Nature, 368:32–38 (1994)] with P(N)= 0.00053 and S. cerevesiae (Acc. no. L05146) with P(N)= 0.0063). Both the C. elegans and S. cerevesiae proteins, in turn, bear similarity to E. coli endonuclease III (Acc. no. J02857). When compared with the sequence of endonuclease III via BLAST the C. elegans and the S. cerevesiae sequence yielded P(N) values of $9.1 \times 10^{-25}$ and $1.9 \times 10^{-7}$, respectively. This same bovine polypeptide demonstrates an even greater degree of similarity to two recently submitted partial 3' cDNA sequences, from H. sapiens (Acc. no. F04657) with P(N)=$6.8 \times 10^{-9}$, and Rattus sp. (Acc. no. H33255) with P(N)=$1.8 \times 10^{-7}$.

FIG. 4 demonstrates the alignment of the E. coli endonuclease III amino acid sequence, with the primary amino acid sequences of the bovine polypeptides, and the predicted amino acid sequences of the C. elegans, H. sapiens, and Rattus sp. proteins derived by translation of their respective nucleotide sequences. The boldface sequence marked with the asterisk represents the 22 amino acid bovine polypeptide found to be most similar to the C. elegans and the H. sapiens and Rattus sp. sequences, as determined by the BLAST program using the default Blosum 62 as the algorithmic matrix and the default expected cutoff value of 10. The other peptides were aligned by the BLAST program after we raised the expected cutoff value from 10 to 100.

DISCUSSION

A mammalian pyrimidine hydrate DNA-glycosylase was purified 5,000 fold from calf thymus (summarized in Table 1). The most purified fractions, after elution from ssDNA cellulose, also demonstrated thymine glycol DNA-glycosylase and AP lyase activities. The AP nicking assay, performed in the presence of 10 mM EDTA, has previously been shown to specifically correspond to β-elimination [Mazumder, et al., 1991, supra]. The elution profiles of the two glycosylase activities and the AP lyase activities were superimposable (FIGS. 2A,2B). The fact that these activities co-eluted in the most purified calf thymus fractions strongly suggests that they are contained within the same protein.

When identical volumes of successive column fractions were analyzed by SDS-PAGE, there was strong correspondence between the intensity of staining of a predominant 31 kD band in the active fractions and the enzyme activities, but several other protein species were also present which could have represented the bovine pyrimidine hydrate-thymine glycol DNA-glycosylase/AP lyase.

Therefore, to definitively identify the bovine enzyme we took advantage of a reductive cross linking reaction which had already been applied to T4 endonuclease V and the E. Coli Fpg protein. It was first demonstrated that, in the presence of NaCNBH$_3$, purified E. coli endonuclease III would form a stable cross link to an oligodeoxynucleotide containing 1 of its substrates, thymine glycol. The apparent increase in molecular weight of the purified enzyme (FIG. 3A, lane 3) together with the phosphorimaging data (FIG. 3B, lane 3) demonstrated unequivocally that the bacterial enzyme was irreversibly cross-linked to the substrate oligodeoxynucleotide. Thus, E. coli endonuclease III, was cross linked to a substrate DNA oligodeoxynucleotide in a manner analogous to T4 endonuclease V and the E. coli Fpg protein, confirming that it also functions via an N-acylimine ES intermediate.

The same reaction was applied to the most purified bovine enzyme fraction and showed that only the predominant 31 kD protein species was irreversibly cross linked to the same thymine glycol-containing oligodeoxynucleotide. The specificity of the reaction was confirmed by separately 5'-end labeling either the thymine glycol-containing or complementary strand of the substrate double-stranded oligodeoxynucleotide. The increase in the apparent molecular mass of the 31 kD protein occurred independently of which DNA strand was labeled; however, only when the thymine glycol-containing oligodeoxynucleotide was labeled did a band corresponding to the shifted protein appear on phosphorimage of the gel (FIG. 3B). That this strategy enabled the successful identification of the bovine analog of E. coli endonuclease III in a relatively complex mixture of mammalian proteins was contingent on the fact, unproven until now, that the mammalian enzyme and the bacterial enzyme both function through a N-acylimine ES intermediate.

The primary amino acid sequence data confirms that the purified 31 kD protein species we identified by reductive cross-linking is a mammalian homologue of endonuclease III. The aligned sequences of FIG. 4 demonstrate the homology between the bovine and C. elegans proteins extending into the region which constitutes the iron-sulfur cluster of E. coli endonuclease III [Thayer, et al., EMBO J, 14:4108–4120 (1995)]. This iron-sulfur cluster motif contains 4 cysteine residues at endonuclease III positions 187, 194, 197, 203 and has been shown to be a DNA binding domain. The H. sapiens and Rattus sp. partial 3' cDNA sequences also contain four cysteine residues which align with those of E. coli endonuclease III and the C. elegans sequence. Thus, it seems probable that the E. coli, C. elegans and mammalian enzymes all share a common mode of DNA binding. A second bovine peptide, and the C. elegans predicted protein, both align with a region containing a known active site amino acid of enamino acid of endonuclease III, aspartic acid 138 (FIG. 4, bold, italics). Another critical active site residue in E. coli endonuclease III is lysine 120 which probably contributes the $\epsilon$-amino group necessary for the formation of the N-acylimine ES intermediate [Thayer, et al., 1995, supra]. Since we have demonstrated such an ES intermediate for the bovine enzyme, it is probable that all mammalian DNA glycosylase/AP lyases will prove to have a lysine residue as part of their active sites. In conclusion, given the similarities in amino acid sequence, including active sites and DNA binding domains among the E. coli endonuclease III, the purified bovine enzyme and the predicted sequences of the C. elegans, H. sapiens and Rattus sp. proteins, there may be a homologous family of endonuclease III-like DNA repair enzymes present throughout phylogeny.

EXAMPLE 2

This example describes the development of the human cDNA corresponding to the bovine EST the purification of which was described above, and is briefly reviewed below.

The DNA repair enzyme was purified 5,000 fold from calf thymus. The enzyme purification was monitored by the assay described above, that measures DNA glycosylase activity against UV irradiated poly(dG-[$^3$H]dC). After the last step of purification, the preparation was analyzed by SDS-PAGE and a predominant 31 kD species appeared in fractions containing enzyme activity. The identity of this species was confirmed via reductive cross-linking of the enzyme protein to its DNA substrate, a reaction resulting from the reduction of the unstable enzyme-substrate intermediate to a stable secondary amine.

The protein band was cut from the gel and subjected to sequencing analysis by standard techniques. The primary amino acid sequence of five polypeptides was determined. One of the peptide sequences (LWSEINGLLVGFGQQTCLPIRP) (SEQ ID NO:28) was found to be homologous to the translated sequences of two 3' EST's submitted to the gene bank in September 1995, a H. sapiens sequence (Accession No. F04657) and a sequence from Rattus sp. (Accession No. H33255).

An oligonucleotide (dGTGGCACGAGATCAATGGACTCTTG) (SEQ ID NO:4) corresponding to a portion of the human EST was used as a probe, to isolate a full length cDNA clone from a Superscript Human spleen cDNA library using the Gene Trapper cDNA positive selection system (GIBCO/Life Technologies). This system facilitates positive selection of clones from a cDNA library. using biotinylated sequence-specific oligonucleotides and magnetic streptavidin beads to enrich the library prior to screening. Nucleotide sequencing yielded the full length cDNA set forth in FIG. 5, and in turn, revealed regions of homology to the primary amino acid sequences of the four other bovine polypeptides. An open reading frame encoding a protein of 292 amino acids was identified. In vitro translation of the full length cDNA sequence has resulted in the synthesis of a protein with an apparent molecular mass of 37 kD on SDS-PAGE which has DNA glycosylase enzyme activity as measured using UV irradiated poly(dG-[$^3$H]dC) as substrate.

DISCUSSION

This enzyme recognizes pyrimidines which have undergone oxidation of the 5,6 double bond (such as thymine glycol) and pyrimidines which have undergone hydration as a result of exposure to UV. Such modified pyrimidines are both toxic and premutagenic and the phenotype of E. coli mutants lacking the homologous enzyme activity is that of a hypermutator.

It is quite likely that the enzyme is an antimutator in mammalian cells and, therefore may be considered to function as a tumor suppressor gene. In heterozygous individuals, loss of the remaining allele would result in the formation of a clone of cells lacking repair capacity. Such cells, exposed to oxidative or UV stress, could not repair the premutagenic modified pyrimidines and, accumulating mutations at an increased rate, could develop into a neoplasm. With appropriate nucleotide primers or probes derived from the sequence of the human gene product this hypothesis can be demonstrated. This could prove useful in prognosis for heterozygous individuals in whom preventive therapy could be instituted.

EXAMPLE 3

Introduction

DNA glycosylase/AP lyases function through N-acylimine (Schiff's base) ES intermediates [Dodson, et al., 1994, supra]. Such ES intermediates can be chemically reduced to stable secondary amines resulting in irreversible cross-linking of the enzymes to their particular substrates [Tchou. et al., J. Biol. Chem., 270:11671–11677 (1995); Dodson, et al., Biochemistry, 32:8284–8290 (1993); Dodson. et al., 1994, supra; Hilbert. et al., Biochemistry, 35:2505–2511 (1996)]. As shown in the previous Examples, this cross-linking reaction was used to definitively identify a pyrimidine hydrate-thymine glycol DNA glycosylase/AP lyase purified from calf thymus. Incubation of a $^{32}$P labeled oligodeoxynucleotide, performed under reducing conditions, containing a single thymine glycol (5,6 dihydroxy-5,6-dihydrothymine) residue with a 5000-fold purified enzyme preparation resulted in cross-linking of a predominant 31 kDa protein to the oligodeoxynucleotide as determined by SDS-PAGE analysis and phosphorimaging. Tryptic digestion of this protein, followed by microsequencing of several of the resulting peptides demonstrated that the bovine enzyme was homologous to theoretical proteins translated from the genomic DNA of S. cerevisiae and C. elegans. Both of these theoretical proteins in turn, were homologues of E. coli endonuclease III. The bovine peptide amino acid sequences were also homologous to the translated sequences of 3'ESTs from *H. sapiens* brain tissue (Acc. no. F04657) and Rattus sp. PC 12 cells (Acc. no. H33255), [Hilbert, et al., 1996, supra].

In the present Example, probes based upon the homologous human 3'EST were used to isolate clones which encode the human homologue of *E. coli* endonuclease III from a splenic cDNA library. Once determined, the cDNA sequence was used to express the enzyme as a functional recombinant protein, and to determine the chromosomal localization of the human gene.

Experimental Procedures

Radionucleotides. [α-$^{32}$P] deoxycytidine-5'-triphosphate (dCTP, 3000 Ci/mmol), [γ-$^{32}$P] adenosine 5'-triphosphate (dATP, 3000 Ci/mmol), [methyl-3H]-thymidine-5'-triphosphate (TTP, 70–90 Ci/mmol) were obtained from Du Pont/NEN.

Cloning of the cDNA. Oligodeoxynucleotides based upon the human 3'EST sequence (Acc. no. F04657) were used to isolate homologous clones from a Superscript human spleen cDNA library in the pCMV-SPORT plasmid vector (GibcoBRL) using the Genetrapper cDNA positive selection system (GibcoBRL), according to the manufacturer's protocol. Briefly, the amplified double stranded cDNA library was made single stranded by treatment with the Gene II product (pliage F1) endonuclease and *E. coli* exonuclease III, and then hybridized to a biotinylated sense strand specific oligodeoxynucleotide P1 (5'-GTGGCACGAGATCAATGGACTCTTG) (SEQ ID NO:4). The cDNA-oligodeoxynucleotide hybrids were captured using streptavidin paramagnetic beads. Non-specifically bound cDNA's were washed away at high stringency and specifically bound cDNA's were eluted from the paramagnetic beads by denaturing the cDNA-oligodeoxynucleotide hybrids. Selected cDNA clones were then made double stranded via repair which was primed by a second sequence specific oligodeoxynucleotide P2 (5'-ATCATTGGACTCTGGGTGGGC) (SEQ ID NO:7). The selected repaired plasmids were electroporated into the *E. coli* strain DH5a and plated onto Lennox L agar plates containing 50 ug/ml ampicillin (LB/amp agar).

After a 20 hour incubation at 37° C. colonies were analyzed for the presence of the desired cDNA insert via colony PCR, according to the manufacturer's protocol, using a second set of 3'EST specific primers (P3, 5'-CAACAGGCGTGGCTTCCTGAAGCG; and P4, 5'-GGTGGGCTTCGGCCAGCAGACCTGT) (SEQ ID NOs:8,9) to maximize specificity of the selection procedure. PCR was conducted as follows: 1 cycle of 95° C. for 2 min; 37 cycles of 94° C. for 1 min, 60° C. for 1 min, 72° C. for 1 min; followed by a final cycle of 10 min at 72° C. PCR products were then analyzed by electrophoresis in a 1.2% agarose gel. Colonies which proved positive through the first PCR, by virtue of the production of a 180 bp product, were subjected to a second round of colony PCR in order to determine the size of the inserts using T7 and SP6 specific primers (5'-TAATACGACTCACTATAGGAGA, and 5'-AGCTATTTAGGTGACACTATAG, respectively) (SEQ ID NOs:10, 11). Of the 23 colonies obtained, 10 proved, through colony PCR and sequencing analysis, to contain the sequence of interest.

Isolation of longer cDNA clones via a second GENETRAPPER selection. In order to isolate additional cDNA clones which contained long inserts and thus had a higher probability of containing the full-length cDNA sequence, the GENETRAPPER cDNA selection system was used a second time, substituting a second set of oligodeoxynucleotides for capture (P5; 5'-ACAGAGACTGCGTGTGGCCTATGAG), and repair (P6; 5'-AAGAGAGCCTGCAGCAGAAGC) (SEQ ID NOs:12, 13) of the selected clones. These primers were not based upon the human 3'EST sequence, but were specific for the 3' portion of previously sequenced cDNA inserts, and therefore were specific for the 5'-portion of the mRNA. Colonies were again screened and insert size determined by PCR as described above. However, rather than using the T7 primer, an additional sequence specific primer P7 (5'-CACCTTGCTCCAGAAACC) (SEQ ID NO:14), was used as a primer in PCR with the SP6 primer to determine the size of the plasmid inserts. PCR-positive colonies which contained the largest inserts were sequenced.

5'RACE analysis. Additionally, to confirm the sequence of the 5' terminus of the mRNA, the 5' RACE System (GibcoBRL, Life Technologies) was used to amplify the 5' terminus of the message for sequencing. The manufacturer's protocol for GC rich cDNA's was followed. Briefly, 2.5 pmoles of a gene specific primer P8 (5'-CATCAGTGACAGCAGCACCT) (SEQ ID NO:15) were hybridized to 100 ng human spleen poly A+RNA (Clontech) and cDNA synthesized using Superscript II Reverse Transcriptase (GibcoBRL, Life Technologies). The RNA was then degraded with RNAse, and the cDNA isolated. A poly dC tail was then added to the 3'-terminus of the purified cDNA using dCTP and TdT, and the cDNA region corresponding to the 5' end of the mRNA was amplified by two successive rounds of PCR using additional gene specific primers P9 (5'-CATAGGCCACACGCAGTCTC, SEQ ID NO:16), and P10 (5'-CTTCTGCTGCAGCCTCTCTTC, SEQ ID NO:17), together with the anchor primers supplied by the manufacturer.

The second round of PCR, yielded a single amplified product which, when analyzed by electrophoresis on a 1.2% agarose gel, corresponded in size to what was expected on the basis of the longest GENETRAPPER-isolated cDNA sequences. The PCR product was gel purified and cloned into the pCR II cloning vector (Invitrogen) using the TA cloning kit (Invitrogen), electroporated into the *E. coli* strain DH5a and plated onto LB/amp agar plates. Colonies were used to inoculate Lennox L broth cultures containing 50 ug/ml ampicillin (LB/amp broth) and the inserts of 10 isolated plasmids sequenced.

DNA Sequencing. Plasmid DNA was purified for sequencing using the QIAprep Spin Plasmid Miniprep Kit (QIAGEN) from 5 ml of LB/amp broth cultures, containing 50 ug/ml ampicillin incubated for 16 hours at 37° C. DNA sequencing was carried out by the NYU Kaplan Cancer Center sequencing facility, using a Model 373 automated DNA sequencer (ABI), and Model 800 Lab Station (ABI).

Construction of a GST-Fusion Protein in pGEX-2T. The DNA sequence encoding amino acids (8–304) of the open reading frame (FIG. 8) were amplified via PCR from 50 ng of the purified cDNA containing plasmid via PCR using the following primers: P11 (5'-CTTGGATCCATGCTGACCCGGAGCCGGAGC) (SEQ ID NO:18), and P12 (5'-CTCGAATTCGAGCCATGCGGCCCTCCGAGA) (SEQ ID NO:19). These primers were designed to incorporate Bam H1 and Eco R1 restriction sites into the 5' and 3' ends of the sense strand, respectively. PCR was conducted as follows: 1 cycle of 95° C. for 2 min; 35 cycles of 94° C. for 1 min, 65° C. for 1 min, and 72° C. for 2 min; followed by a final cycle of 10 min at 72° C. The resulting PCR product was digested with Bam H1, and Eco R1, gel purified and then ligated into gel purified pGEX-2T vector (Pharmacia)

which had previously been digested with Bam H1 and Eco R1, and electroporated into the *E. coli* strain NB42. Colonies were selected via growth on LB agar/amp plates, and the presence of the appropriate insert verified via colony PCR as described above, using primers P3 and P4. Expression of the full length fusion protein was confirmed via the induction of log phase (A590=0.6) 5 ml LB/amp broth cultures with 0.1 mM IPTG for 4 hours at 37° C. To prepare total cell SDS lysates 1 ml aliquots of induced and uninduced cultures were centrifuged at 5000×g for 2 min, the supernatant was discarded, and the pelleted bacteria were resuspended in 100 ul of SDS-PAGE loading buffer and heated at 95° C. for 5 min. Thirty ul of each sample was then analyzed on a 15% Tricine gel. After the gels were stained with Coomassie-blue, induced and uninduced samples were compared to demonstrate the expression of the full length (65 kDa) fusion protein. Bacterial lysates produced in an identical manner were also run on the SDS Page gel in FIG. 10 in order to demonstrate induction of the GST-fusion protein.

Protein Expression and Purification. 600 ml of LB/amp broth were inoculated with 10 ml of overnight cultures. Bacteria were grown at 37° C. until the A590 reached 0.6. Expression of the fusion protein was induced by incubation with 0.1 mM IPTG for 5 hours at 30° C. (the lower temperature was used to increase the solubility of the fusion protein). Bacteria were then placed on ice for 1 hour, and pelleted by centrifugation at 3200×g in 250 ml centrifuge tubes (Corning) for 10 min. The supernatant was discarded, and the pellet resuspended in 20 ml of sonication buffer (50 mM Tris, pH 8.0, 500 mM NaCl, 5 mM EDTA, 0.5% Triton X-100, 0.25 mM PMSF, 0.1 mg/ml Aprotinin). The bacteria were transferred to a 30 ml Corex centrifuge tube, and sonicated for 2 min at 70% power using a Heat Systems model W-375 sonicator equipped with a model 419 standard tapered microtip. The sonicate was then centrifuged for 15 min at 10,000×g, and the supernatant transferred to a 50 ml plastic centrifuge tube containing 1.2 ml glutathione agarose 4B affinity media (volume of media was measured as a slurry in 20% ethanol, as supplied by the manufacturer) prewashed with 2×40 ml of wash buffer (50 mM Tris, pH 8.0, 500 mM NaCl, 5 mM EDTA, 0.5% Triton X-100). The sample was incubated on ice with agitation for 30 min to allow adsorption of the fusion protein. The affinity media was then pelleted by centrifugation for 2 min at 950×g. The supernatant was removed by pipetting, and the affinity media washed once with 20 ml of sonication buffer, and 4 times with 40 ml of wash buffer by thorough resuspension of the beads in the appropriate buffer followed by centrifugation at 950×g for 1 min. After the final wash, the affinity media was resuspended in 1 ml of wash buffer, transferred to a 2 ml plastic tube, and centrifuged again at 950×g for 1 min to pellet the beads. The supernatant was removed, and the beads were resuspended in 1 ml glutathione-agarose elution buffer (100 mM Tris, pH 8.0, 500 mM NaCl, 2.5 mM EDTA, 0.1% Triton X-100, 20 mM glutathione (Sigma)) and incubated for 12 hours on ice with agitation. Beads were then quickly pelleted by centrifugation at 950×g and the supernatant which contained the eluted fusion protein transferred to a fresh tube. All purification procedures from sonication through elution of the fusion protein were carried out at 4° C. The purification yielded 9.9 mg of fusion protein.

As a control the 26 kDa glutathione S-transferase (GST) of *S. japonicum* was expressed from the pGEX-2T vector (without a fusion insert) in the bacterial strain NB42 according to the same procedure described for the fusion protein. Twelve mg of purified GST was purified from 600 ml of induced bacterial culture.

Purification of *E. coli* endonuclease III. Endonuclease III was purified from *E. coli* strain UC6444 carrying the plasmid pHIT1 as previously described [Asahara, et al., 1989, supra].

Spectrophotometry. Spectrophotometric measurements of proteins were made in elution buffer (100 mM Tris, pH 8.0, 500 mM NaCl, 2.5 mM EDTA, 0.1% Triton X-100, 20 mM glutathione) in a quartz cuvette. The optical absorption spectra of the GST-fusion protein and the unfused GST (glutathione s-transferase) protein were recorded between 200 nm-700 nm using a Spectronic Genesystems 5 spectrophotometer (Milton Roy). In order to allow comparison of the absorption spectra of the purified GST-fusion protein, and purified GST (FIG. 13 the purified proteins were diluted prior to analysis with glutathione-agarose elution buffer to the same absolute protein concentration (5.5 mg/ml).

FISH analysis. FISH analysis was performed by SeeDNA Biotech Inc., Dept. of Biology, York University, Ontario, Canada. Lymphocytes isolated from human blood were cultured in a -minimal essential medium (MEM) supplemented with 10% fetal calfserum and phytohemagglutinin (PHA) at 37° C. for 68–72 hours. The lymphocyte cultures were treated with BrdUrd (0.18 mg/ml Sigma) to synchronize the cell population. The synchronized cells were washed 3 times with serum-free medium to release the block and recultured at 37° C. for 6 hours in a minimal essential medium with thymidine (2.5 mg/ml; Sigma). Cells were harvested and slides made by using standard procedures, including hypotonic treatment, fixing, and air-drying.

To produce a probe for FISH analysis, a 1.1 kb fragment containing the entire cDNA sequence was excised from an isolated cDNA clone using Eco R1 and Hind III, purified and labeled with biotin-14-dATP using the BioNick labeling kit (Gibco BRL) [Heng, et al., *Proc. Natl. Acad. Sci. U.S.A.,* 89:9509–9513 (1992)]. The procedure for FISH analysis was performed according to the previously reported procedures of Heng, et al. [*Chromosomes,* 102:325–332 (1993): *Methods in Molecular Biology: In Situ Hybridization Protocols,* pp. 35–49 (1994)]. Briefly, slides were baked at 55° C. for 1 h. After RNAse treatment, the slides were denatured in 70% formamide, 2×SSC for 2 min at 70° C. followed by dehydration with ethanol. Probes were denatured at 75° C. for 5 min in a hybridization solution containing 50% formamide, 10% dextran sulphate and human Cot I-restricted DNA. Probes were loaded on the denatured chromosomal slides. After overnight hybridization, slides were washed and analyzed. FISH signals and the DAPI banding pattern were recorded separately by taking photographs. Chromosomal localization was achieved by superimposing FISH signals with DAPI banded chromosomes [Heng, et al., 1994, supra].

Northern Blot Analysis. Two ug of mRNA, isolated from 293T cells using the FastTrack 2.0 mRNA isolation system (Invitrogen), 1 ug of human spleen Poly A+RNA (Clontech), and 5 ug of 0.24–9.5 Kb RNA Ladder (GibcoBRL) were electrophoresed on a 11×14 cm 1.0% agarose-formaldehyde gel. The gel was rinsed with deionized water and RNA transferred to a Nytran membrane (Schleicher & Schuell) using the Turboblotter rapid downward transfer system (Schleicher & Schuell), according to the manufacturer's specifications. Following transfer the membrane was gently washed in 2×SSC for 5 min, dried on a fresh sheet of filter paper, and baked at 80° C. for 1 hour. The portion of the membrane which contained the molecular weight markers was cut away and stained by treatment with 5% acetic acid for 15 min, 0.5M sodium acetate, pH 5.2 with 0.04% methylene blue 10 min, followed by destaining with water.

Figure 8A:
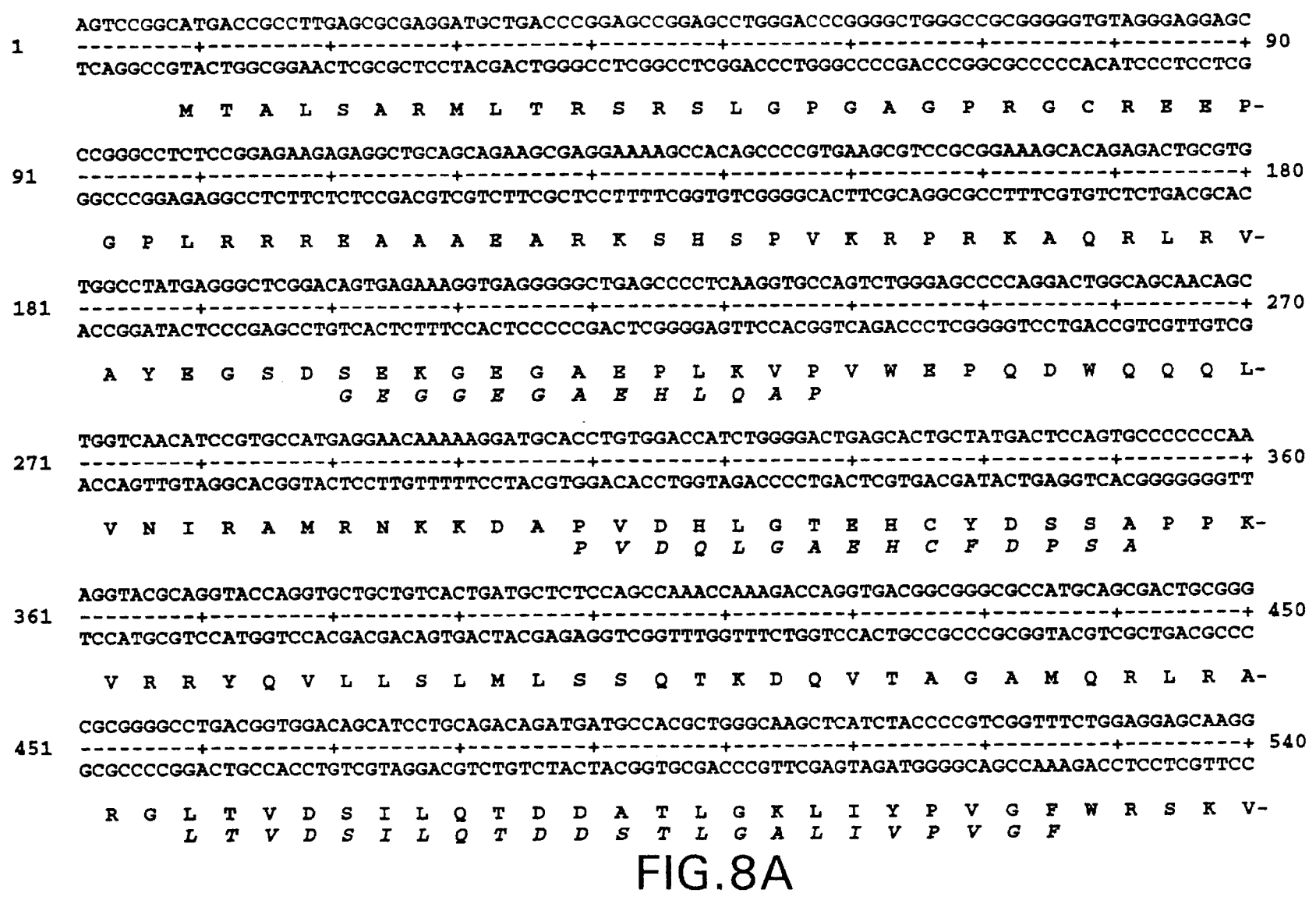
Figure 8B:
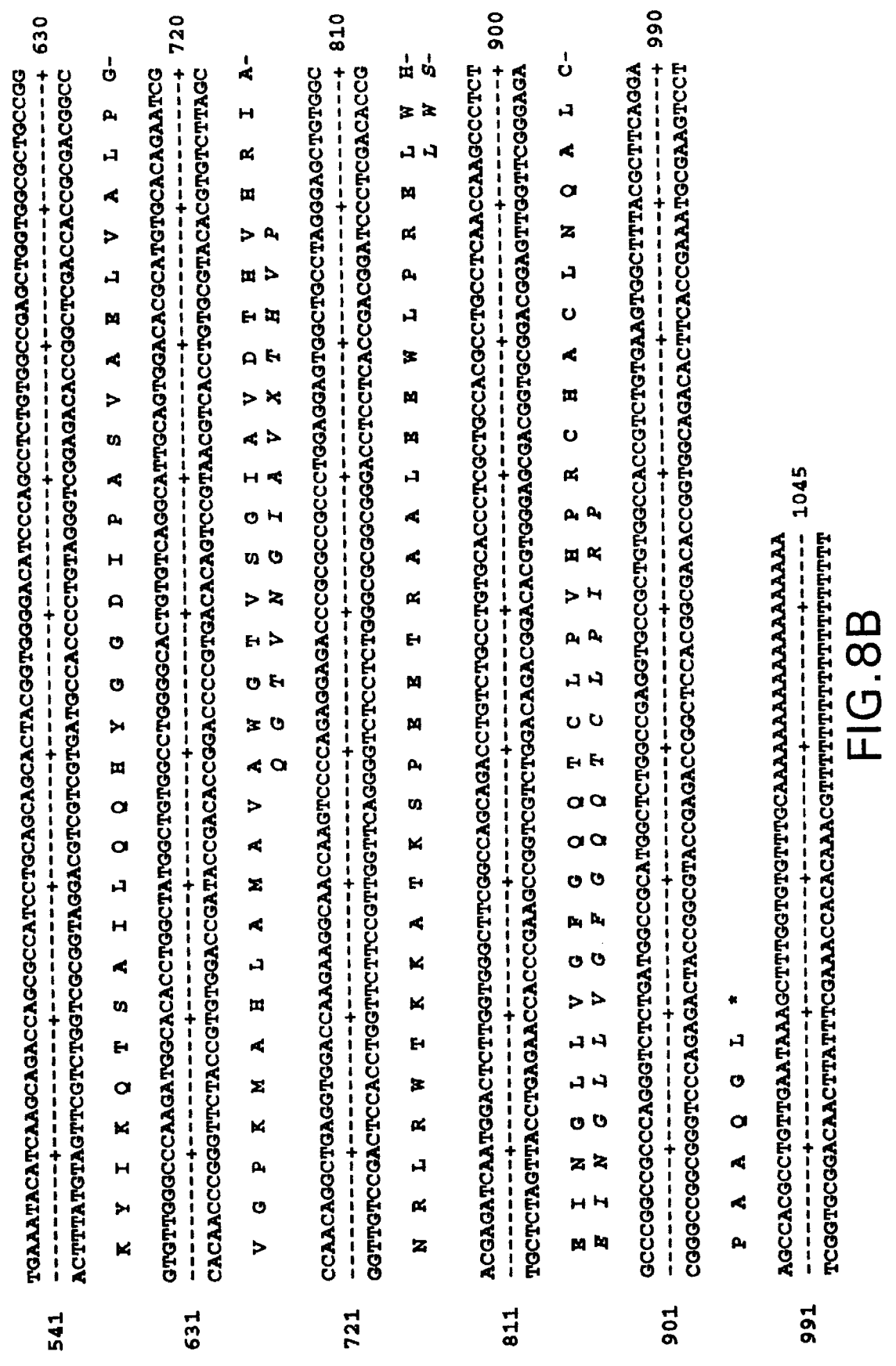

The baked filter was incubated in prehybridization solution (in 50% formamide, 3×SSC, 0.1M Tris, pH 7.4, 5×Denhardt's solution) for 4 hours at 42° C., followed by hybridization overnight at 42° C. with 2×10$^6$ cpm of radio-labeled probe/ml of hybridization solution (50% formamide, 3×SSC, 0.1M Tris pH 7.4, 5×Denihardt's solution, 10% Dextran sulfate). Following hybridization, the membrane was washed 3 times for 30 min at 50° C., successively with 1×SSC, 0.1% SDS; 0.5×SSC, 0.1% SDS; 0.1×SSC, 0.1% SDS. The membrane was exposed to X-ray film for 24 hours at −70° C. The autoradiogram was matched to the prestained markers to determine the size of the native mRNA. Before hybridization with the cDNA-specific probe, the Northern blot membrane was analyzed by hybridization to a β-actin specific probe to confirm the integrity of the mRNA. After hybridization to the β-actin probe detected an mRNA species of the predicted size (approximately 2.1 Kb) the membrane was stripped by boiling for 30 mini in 0.1×SSC, 0.5% SDS and probed according to an identical procedure with the probe specific for the human homologue of endonuclease III (FIG. 8).

Preparation of Probes for Northern Blot Analysis. The β-actin probe was produced by PCR with sequence specific primers (Clontech) against cDNA made from the RNA of cells taken from a sample of a human bone marrow aspirate. PCR was conducted as follows: 1 cycle of 95° C. for 2 min; 35 cycles of 94° C. for 1 min, 60° C. for 1 min, 72° C. for 1 min; followed by a final cycle of 10 min at 72° C. The probe was then radiolabeled using the Random Primed DNA Labeling Kit (Boehringer-Mannheim), and [α-$^{32}$P] dCTP, and purified using Nick-Spin columns (Pharmacia). The specific probe for the human homologue of endonuclease III which was prepared by excising the full length cDNA sequence shown in FIG. 8 from the 2 ug of purified plasmid DNA via restriction with EcoR1 and BamH1 followed by gel purification of the restricted fragment. The probe was radiolabeled and hybridized to the Northern blot membrane, as described.

DNA Glycosylase Assay. Poly(dA-[3H]dT) was produced by nick-translation of the alternating copolymer poly (dA-dT) (Pharinacia) with [5',5-3H] TTP followed by oxidation with osmium tetroxide to form thymine glycol residues [Higgens, et al., 1987, supra]. Thymine glycol-containing poly(dA-[3H]dT) produced in this manner had a specific activity of approximately 1.4×107 dpm/ug. Thymine glycol DNA-glycosylase assays were carried out against oxidized DNA and the released radioactive product proven to be thymine glycol by HPLC analysis as previously described [Higgens, et al., 1987, supra].

Sodium cyanoborohydride mediated cross-linking of fusion protein to a thymine glycol containing oligodeoxy-nucleotide. A double stranded oligodeoxynucleotide containing a single thymine glycol-residue was prepared as described previously [Hilbert, et al., 1996, supra; Kao, et al., 1993, supra]. The thymine glycol containing strand was 5'-end labeled with [γ-$^{32}$P] dATP, using T4 kinase (Gibco BRL) according to the manufacturer's recommendations, and purified using a ChromaSpin-10 column (Clonetech).

The purified GST-fusion protein, the non-fusion GST protein and E. coli endonuclease III were reacted with the substrate double-stranded oligodeoxynucleotide in a total volume of 50 ul under the following reaction conditions: 37.3 mM NaCNBH$_3$, 20 mM HEPES, pH 7.5, 46.5 mM KCl, 5 mM EDTA, 4.0 uM of each oligodeoxynucleotide, 40 ng/ul protein. In the case of E. coli endonuclease III, this represented approximately a 4-fold molar excess of substrate deoxyoligonucleotide to enzyme. After incubation at room temperature for 2 hours. 25 ul volume of 3×SDS PAGE loading buffer was added to each sample. Samples were then heated to 90° C. for 5 min and separated by electrophoresis on a 15% Tricine-SDS gel. Following electrophoresis, the gel was stained with Coomassie Blue, wrapped in plastic, and analyzed via autoradiography.

Gel Electrophoresis. Prior to electrophoresis all samples were incubated at 95° C. for 5 min in standard SDS PAGE loading buffer. Fifteen percent Tricine gels [Shagger. et al., 1987, supra] were prepared and run using the Mini-Protein II electrophoresis system (Bio-Rad). Gels were run at 90 V for approximately 5 hours, completion being determined by the progress of pre-stained low molecular weight electrophoresis standards (Bio-Rad). Gels were then stained with Coomassie Blue.

RESULTS

The nucleotide sequence of a cDNA corresponding to the human homologue of E. coli endonuclease III is shown in FIG. 8. The 1045 bp cDNA contains a putative open reading frame (ORF) of 912 bp, which encodes a protein of 304 amino acids having a calculated molecular mass of 33,569 and pI of 9.85. The nucleotide sequence data was obtained from two sources. The sequence of nucleotides 6 to 1045 was obtained by analysis of clones isolated from a cDNA library using probes based upon the sequence of the previously described human 3' EST. The sequence of nucleotides 1 to 5 was obtained by sequencing the products of 5'RACE using gene specific primers based upon the sequence of the longest cDNA clones.

In the previous Examples, the sequence of four peptides obtained by proteolysis of a purified bovine pyrimidine hydrate-thymine glycol DNA glycosylase/AP lyase was disclosed [Hilbert, et al., 1996. supra]. The sequences of those 4 peptides, as well as that of one additional peptide (GEGGEGAEHLQAP) (SEQ ID NO:24) derived from the same purified protein, also depicted in FIG. 8, are shown aligned with the homologous sequences encoded within the ORF of the human cDNA.

The 1045 bp sequence of FIG. 8 likely represents most, if not all of the entire full length cDNA. The northern blot analysis (FIG. 9) of human splenic and 293T cell (human) mRNA each demonstrate a predominant mRNA species of approximately 1.1–1.2 Kb which hybridized to a $^{32}$P-labeled probe containing the entire sequence of the ORF. A difference of approximately 50 to 150 nucleotides in length between the cDNA sequence presented in FIG. 8 and the native mRNA is explained by the expected presence of a polyA tail approximately the same length on the native species (perhaps a few more nucleotides) 5' to the first AUG codon.

Figure 9:
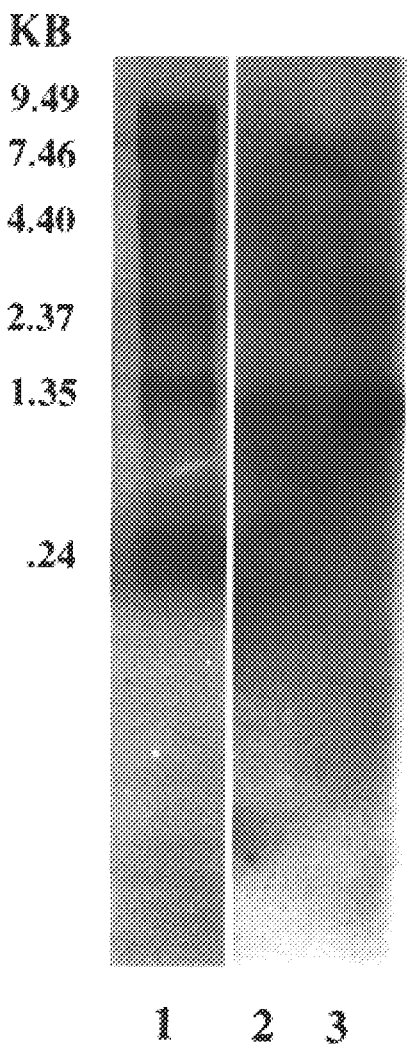
FIG. 9. Northern blot analysis. Northern blot analysis was performed against 1 ug of mRNA from human spleen (Lane 2) and 2 ug of mRNA from human 293T cells (Lane 3), using the full lenght $^{32}$P-labeled cDNA for the human pyrimidine hydrate-thymine glycol DNA glycosylase/AP lyase as a probe. Methylene blue-stained RNA markers are shown in Lane 1.

FIG. 9, lane 3, which contains mRNA extracted from 293T cells, demonstrates a shows faint band of higher MW. Although it is postulated that this band is non-specific, the possibility that it represents mRNA encoding a protein similar to human endonuclease III cannot be excluded. This is the case found in S. cerevesiae, which contains two homologues of E. coli endonuclease III, one believed to be nuclear, the other mitochondrial (see FIG. 15 and Discussion infra.).

To demonstrate that the cDNA sequence of FIG. 8 encodes a functional homolog of endonuclease III, a GST fusion protein was constructed consisting of amino acid residues 8 to 304 of the ORF fused to the C-terminus of the 30 kDa GST protein. SDS-PAGE analysis of the IPTG induced. affinity-purified fusion protein (FIG. 10) revealed a predominant 65 kDa full length protein. Two additional lower molecular weight protein species were present in the purified preparation. It is believed that these proteins are fragments of the 65 kDa protein arising from the abortive synthesis of the full-length protein, or from proteolysis occurring before, during, and after cell lysis and affinity purification due to the action of contaminating cellular proteases.

As described previously, E. coli endonuclease III can be specifically, irreversibly cross-linked to a thymine glycol-containing oligodeoxynucleotide, via the reductive stabilization of its characteristic ES intermediate [Hilbert, et al., 1996, supra]. To further confirm that the ORF presented in FIG. 8 encodes a fully functional homologue of E. coli endonuclease III the cross-linking reaction, as described in the Experimental Procedure section (above), was applied to the purified GST-fusion protein. The results of this reaction are illustrated in FIG. 11. When aliquots of the purified GST-fusion protein incubated with $^{32}$P-labeled thymine glycol-containing oligodeoxynucleotide, in the absence (Lane 6) or presence (Lane 7) of sodium cyanoborohydride (NaCNHB$_3$), were compared by SDS-PAGE analysis it was evident that a portion of the protein had been irreversibly cross-linked to the oligodeoxynucleotide. This is manifest by an increase in the apparent molecular weight of the enzyme resulting in the formation of the doublet shown in Lane 7. The shift is analogous to that observed when endonuclease III was subjected to the same reductive cross-linking reaction (Lane 3), and compared with native endonuclease III (Lane 2). No shift of the major protein species was observed when the non-fusion GST protein (Lane 3) was incubated under reducing conditions with the thymine glycol-containing oligodeoxynucleotide (Lane 4).

Figure 10:
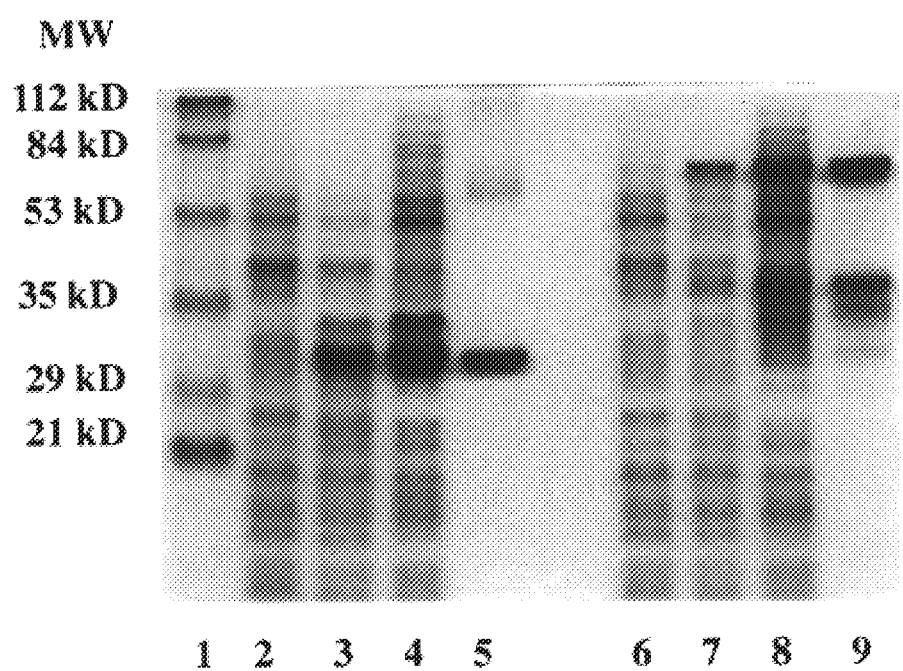
FIG. 10. Expression and purification of the recombinant human pyrimidine hydrate-thymine glycol DNA glycosylase/AP lyase. SDS-PAGE analysis of the GST fusion protein. Lane 2 is total SDS lysate from uninduced *E. coli* containing the pGEX-2T vector. Lane 3 is total SDS lysate of the same *E. coli* after induction by IPTG for 5 h. Lane 4 is the soluble fraction obtained by centrifugation of induced *E. coli* disrupted by sonication. Lane 5 is the purified GST protein after elution from glutathione agarose affinity media. Lane 6 is the total SDS lysate from uninduced *E. coli* containing the pGEX-2T vector into which the sequence encoding the human enzyme had been cloned. Lane 7 is total SDS lysate from induced *E. coli*, containing the recombinant pGEX-2T vector. Lane 8 is the soluble fraction of induced disrupted *E. coli* containing the recombinant pGEX-2T vector. Lane 9 is the purified GST fusion protein after elution from affinity media. Lanes 1 and 10 are MW markers.
Figure 11A:
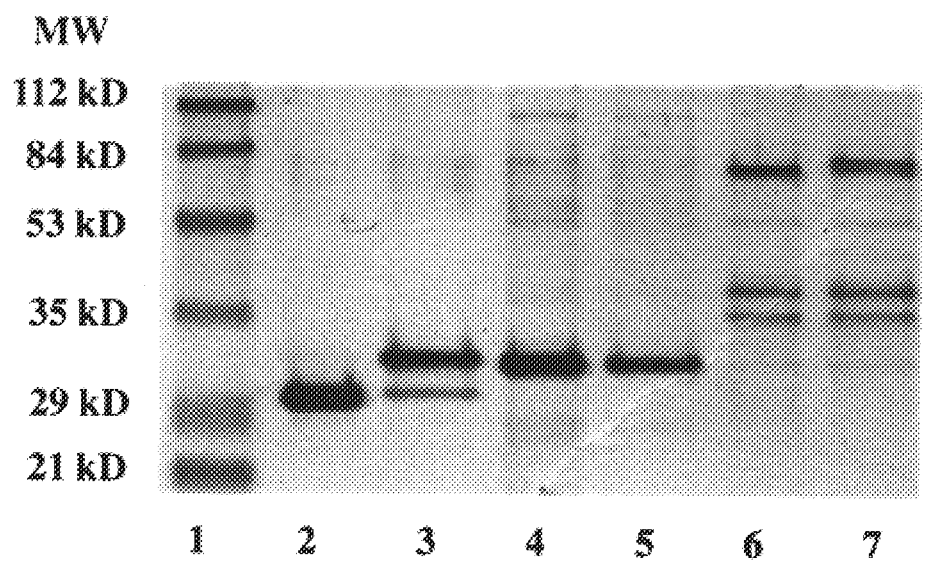
FIG. 11. SDS-PAGE analysis of *E. coli* endonuclease III and the human GST fusion protein after incubation with the thymine glycol-containing oligodeoxynucleotide and NaCNBH$_3$. A, Lane 1 contains MW markers. Lane 2 contains the product of the incubation of *E. coli* endonuclease III with NaCNBH$_3$. Lane 3 contains the product of the same incubation mixture as Lane 2 with addition of duplex 5'-$^{32}$P labeled oligodeoxynucleotide containing a single thymine glycol residue. Lane 4 contains the product of the incubation the purified non-fusion GST protein (FIG. 3, Lane 5) with NaCNBH$_3$ but no oligodeoxynucleotide. Lane 5 contains the product of the incubation of the same purified non-fusion GST protein with NaCNBH$_3$ and the 5'-$^{32}$P-labeled oligodeoxvnucleotide. Lanes 6 and 7 contain the products of the incubation of the purified GST fusion protein (FIG. 3, Lane 9) with NaCNBH$_3$ alone, or NaCNBH$_3$ and oligodeoxynucleotide respectively. B, Phosphorimage of the SDS-PAGE gel of FIG. 4A. The lanes are identical to those described in A. The MW in lane 1 are not radiolabeled, but are the same Coomassie-stained markers shown in FIG. 4A.
Figure 11B:
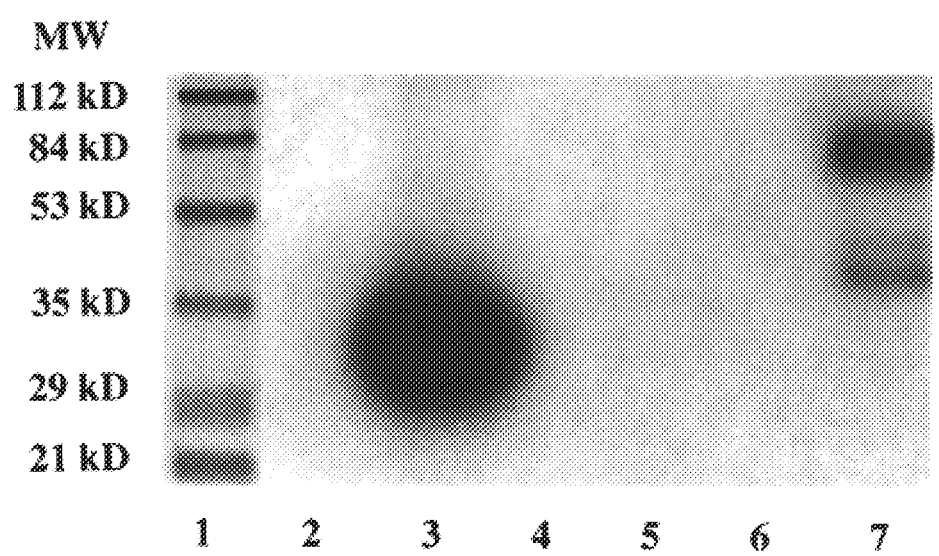

An autoradiogram of the gel in FIG. 11A is presented in FIG. 11B. As previously described, the thymine glycol-containing oligodeoxynucleotide was 5'-end labeled with $^{32}$P prior to incubation with the proteins. Thus, cross-linking was confirmed by this autoradiogram in which predominant radioactive species were present only in Lanes 2 (E. coli endonuclease III plus NaCNHB$_3$) and 7 (GST fusion plus NaCNHB$_3$) which correspond in apparent MW to the shifted species seen on the Coomassie blue stained gel. Also evident on the autoradiogram in Lane 7 are two visible, but less intense lower molecular weight bands which correspond in position to presumed degradation products of the fusion protein present even after affinity purification (FIG. 10). Presumably these represent cross-linked, partially degraded fusion protein.

Figure 12:
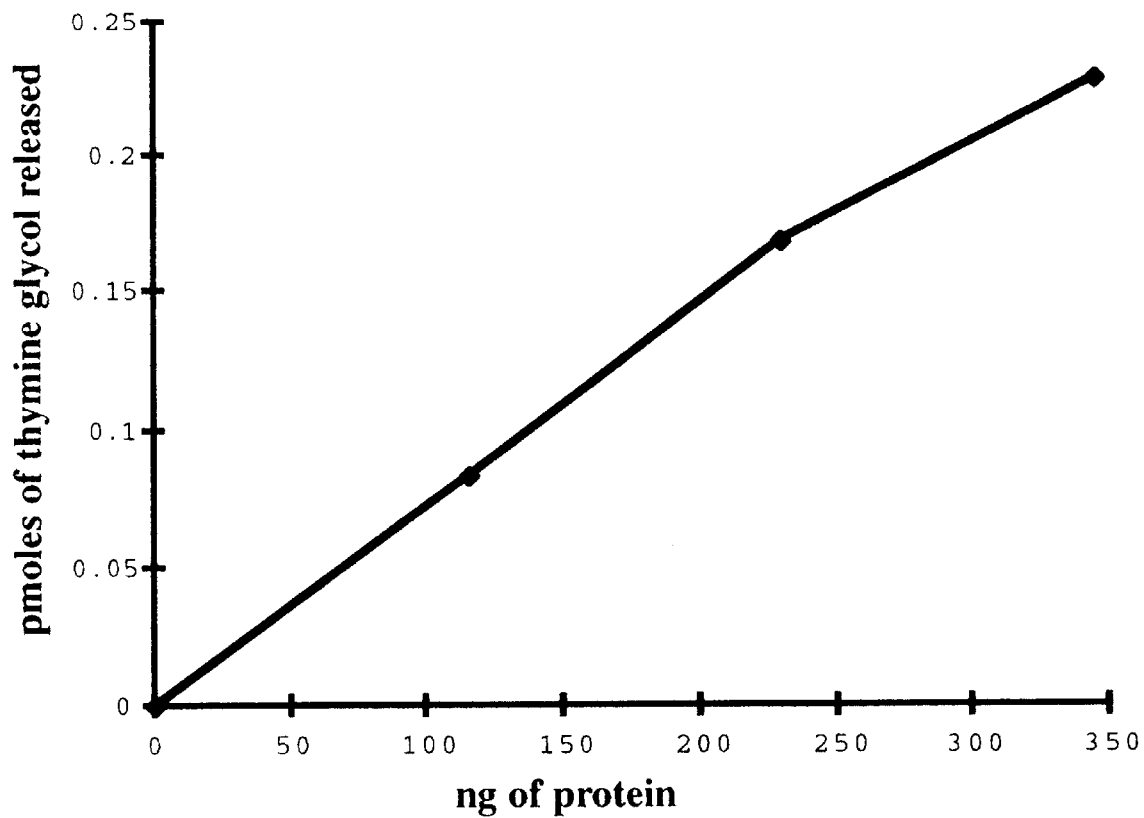
FIG. 12. v vs. [E$_r$] plot. Amount of thymine glycol released after incubation of oxidized alternating poly (dA-dT) for 20 min with recombinant protein. The points represent the average of 2 determinations. There was less than 5% variability among duplicate samples.

After purification, the fusion protein was also analyzed for thymine glycol-DNA glycosylase activity. FIG. 12 presents the V vs. [E$_t$] plot in which thymine glycol release is expressed as a function of increasing content of fusion protein. The release of thymine glycol is linear with respect to fusion protein concentration over the amount of protein used. Based on the results of this plot, the specific enzymatic activity of the fuision protein was calculated to be about 1–2% of genetically engineered E. coli endonuclease III using the same assay. This reduced level of activity is apparently quite common among GST fusion proteins. GST protein, which contained no C-terminal fusion was induced and purified in a manner identical to the fusion protein and assayed for enzymatic activity. This non-fusion GST protein did not demonstrate detectable thymine glycol-DNA glycosylase activity at a protein concentration 3 orders of magnitude higher than that at which the fusion protein was assayed.

Figure 13A:
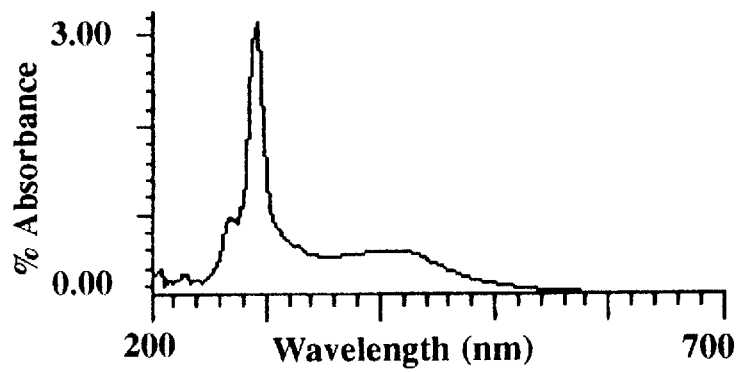
FIG. 13A, Optical absorption spectrum of the purified human pyrimidine hydrate-thymine glycol DNA glycosylase/AP lyase-GST fusion protein.
Figure 13B:
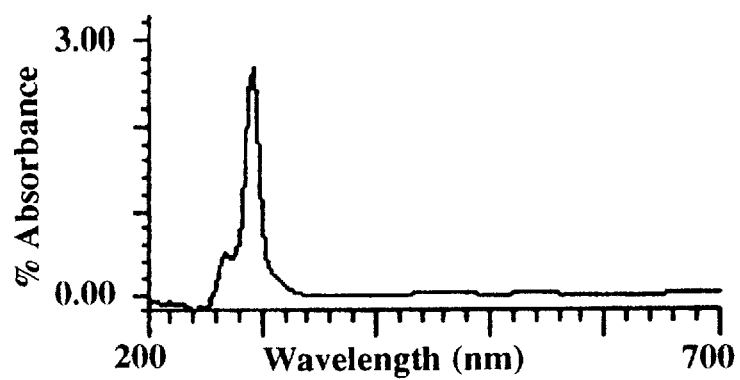
FIG. 13B, Optical absorption spectrum of the purified non-fusion GST protein of *S. japonicum*.

As documented previously, E. coli endonuclease III, contains an iron-sulfur cluster in which a cubane [4Fe-4S] moiety is liganded by four cysteine residues. This domain produces a distinctive absorbency at 410 nm, [Thayer, et al., 1995, supra]. Conservation of this [4Fe-4S] cluster in the human enzyme was inferred on the basis of the cDNA sequence of FIG. 8, since the putative ORF contains the appropriate four cysteine residues at amino acid positions 282, 289, 292 and 300, and confirmed by taking an absorption spectrum of the purified GST-fusion protein which revealed that it too absorbed strongly at 410 nm (FIG. 13).

Purified E. coli endonuclease III has a characteristic absorption peak at 410 nm and as expected solutions containing approximately 0.5 mg/ml or greater of purified endonuclease III are typically yellow-brown [Asahara, et al., 1989, supra]. Similarly, a solution of the purified GST fusion protein at similiar concentrations of protein, was also yellow, while a solution of the simultaneously purified non-fusion GST protein was colorless.

Figure 14:
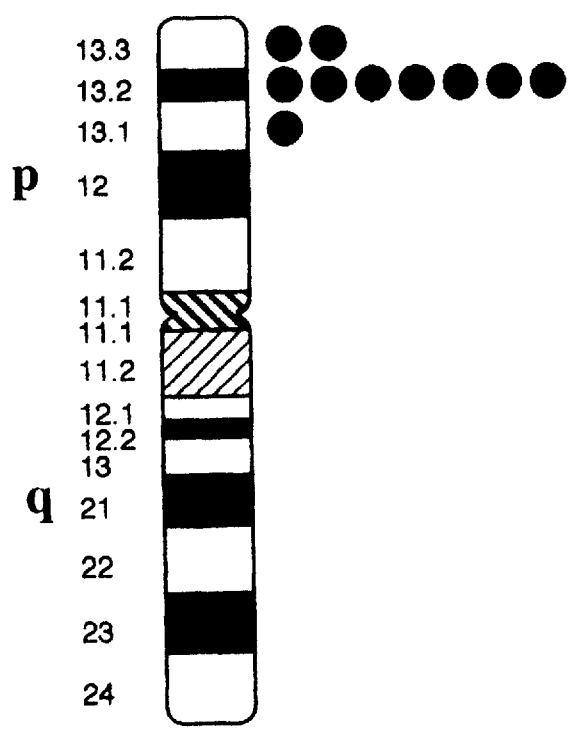
FIG. 14. Histogram of FISH analysis results. Ten mitotic figures to which the FISH probe had bound were analyzed to determine the precise position of the gene on chromosome 16. Each dot represents the position of the human gene as determined through one such analysis.

In order to determine the chromosomal localization of the gene encoding the mammalian enzyme FISH analysis was performed as described in Experimental Procedures (above). Under the conditions used, hybridization efficiency for our probe was approximately 70% (i.e. among 100 mitotic spreads analyzed, 70 demonstrated binding of the probe to one pair of chromosomes). DAP1 banding was used to identify the chromosome pair to which the probe had bound (chromosome 16). The precise localization of the gene (16p13.2) was determined by the summary analysis of 10 pairs of photographs in which the probe signal was matched with the results of DAP1 banding (FIG. 14). There was no additional locus detected by FISH analysis. These results taken together with the presence of a single mRNA species on Northern analysis indicates that the gene for human endonuclease III is a single copy gene.

DISCUSSION

The human sequence of FIG. 8 shows remarkable similarity to that of several other putative homologs of the E. coli endonuclease III (Acc No. J02847) found in representative species of all 3 biologic domains. In bacteria they have been found in both Gram negative (H. influenza, NCBI Seq. ID 1169526) and Gram positive (B. subtilis, NCBI Seq. ID 729418) organisms; among archaea, in M. jannaschii, (NCBI Seq. ID 1510694) and among eukaryotes, in S. pombe (NCBI Seq. ID 1065894), S. cerevisiae (NCBI Seq. ID 1419843, and 401436), C. elegans (NCBI Seq. ID 974795), Rattus sp. (Acc. no. H33255) and H. sapiens (Acc. no. F04657). The S. cerevisiae genome encodes two distinct theoretical homologues of E. coli endonuclease III. The alignment of the 9 putative homologous sequences using the program Clustal W(1.5) (FIG. 15) reveals that a core sequence of amino acids is remarkably well conserved. In bacteria, the core sequence comprises virtually the entire protein. In contrast, the proteins of archeons and eukaryotes have unique extensions at their N-and/or C-termini. For the sake of clarity these extensions have been omitted from FIG. 15.

Based upon similarities among several bacterial DNA glycosylases, site directed mutagenesis studies, and molecular modeling, several regions and residues within the core sequence of amino acids of E. coli endonuclease III could be involved in DNA binding and catalysis [Thayer, et al., 1995, supra]. The region surrounding glutamine 41 (residue numbers refer to the E. coli endonuclease III amino acid sequence, unless otherwise indicated), may form a portion of the substrate binding pocket, in which the damaged pyrimidine fits when in the "flipped out" conformation which the enzyme recognizes. The Helix-hairpin-Helix (HhH) motif encoded by the residues surrounding the central LPGVG sequence (residues 114–118) (SEQ ID NO:3) is thought to function in non-specific DNA recognition. This analysis has been extended to show that similiar HhH motifs occur in 14 homologous families of DNA proteins binding, including DNA glycosylases, DNA polymerases, and "flap" endonucleases [Doherty, et al., *Nucleic Acids Res.*, 24:2488–2498 (1996)]. Lysine 120 appears to be the nucleophile in the active site of endonuclease III which contributes the e-amino group necessary for the formation of the N-acylimine ES intermediate, characteristic of DNA glycosylase/AP lyases. Aspartic acid 138 has also been implicated as a functional active site residue. All of these residues appear to be well conserved in all of the 9 sequences shown. The structure of the *E. coli* endonuclease III was recently solved [Thayer, et al., 1995, supra] and, in light of the high degree of conservation of critical residues, it is likely that the common core sequence of all members of the endonuclease III family will have a similar three-dimensional structure.

In addition to the previously mentioned residues, 4 highly conserved cysteine residues (187, 194, 197, 203) have been identified within this common core sequence which contribute to the [4Fe-4S] cluster of *E. coli* endonuclease III. Examination of the aligned sequences in FIG. 15, reveals that in *E. coli* endonuclease III and 5 of its 8 putative homologues, including the human enzyme, these 4 cysteines are arranged according to the consensus sequence Cys-X6-Cys-X2-Cys-X5-Cys (SEQ ID NO:21). A similar but slightly modified sequence appears in *S. pombe* (Cys-X6-Cys-X2-Cys-X7-Cys) (SEQ ID NO:22) and *M. jannaschii* (Cys-X5-Cys-X2-Cys-X7-Cys) (SEQ ID NO:23). The basic amino acid residues between the first two cysteines of the [4Fe-4S] cluster may form a loop which functions in the nonspecific binding of DNA [Thayer. et al., 1995, supra]. While FIG. 15 does not indicate absolute conservation of these residues, some conservation is apparent, especially with respect to arginine 193.

Figure 15:
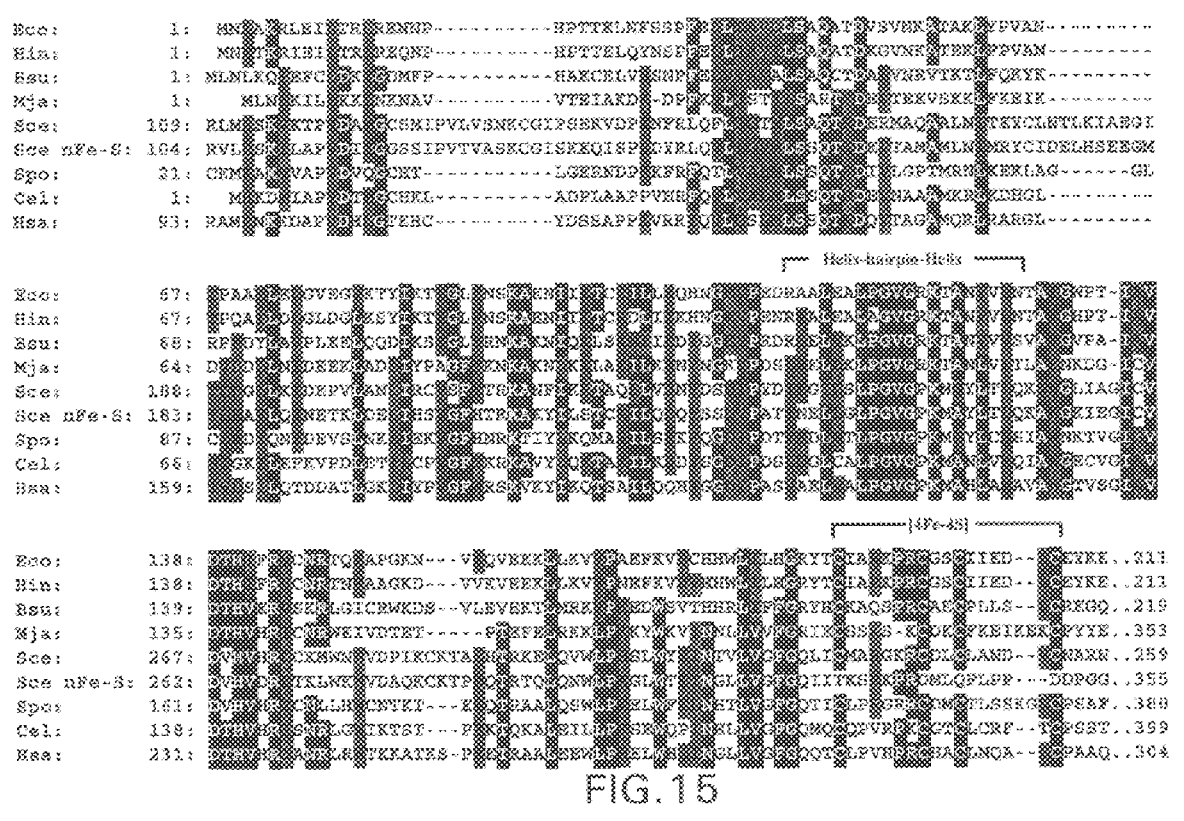

As mentioned previously, the genome of *S. cerevisiae* encodes two putative homologues of *E. coli* endonuclease III, one of which designated Sce non Fe-S in FIG. 15 (NCBI Seq. ID 1419843) lacks the four cysteine [4Fe-4S] motif completely and presents an obvious exception to this consensus sequence. However, this sequence also encodes a putative mitochondrial leader sequence [Ouellette, et al., *Genome*, 36:32–42 (1993)]. Whether pairs of endonuclease III-like proteins, with and without [4Fe-4S] clusters, are present in other eukaryotic organisms and whether the non Fe-S proteins are mitochondrial remains to be determined.

This interesting question notwithstanding, the presence of endonuclease III-like enzymes in representative species of all three evolutionary domains, suggests that the genomic DNA of organisms throughout phylogeny is subject to endogenous stresses which attack the 5,6 double bonds of pyrimidine residues. Previously well characterized substrates of endonuclease III include oxidized pyrimidines such as thymine glycol and 5-hydroxycytosine and hydrates of cytosine and uracil. The oxidation of DNA bases has been primarily attributed to reactive oxygen species formed as byproducts of oxidative metabolism and inflammation. The formation of pyrimidine hydrates has been primarily attributed to the action of UV radiation [reviewed in Teebor, *DNA Repair Mechanisms and Cancer*, pp. 99–123 (1995)]. The archeon *M. jannaschii* lives beneath the sea and therefore is not exposed to direct sunlight. Furthermore, it is characterized by a reducing rather than an oxidizing metabolism [Bult, et al., *Science*, 273:1058–1073 (1996)]. The identification of a homologue of endonuclease III in the genome of this organism suggests that pyrimidines with reduced 5,6 double bonds such as 5,6-dihydrothymine may be formed spontaneously in archeon genomic DNA. Perhaps within this evolutionary domain, it is primarily the formation of such reduced rather than oxidized or photohydrated pyrimidine residues which has promoted the conservation of an endonuclease III-like enzyme.

At this time, the specific contribution which the human pyrimidine hydrate-thymine glycol DNA glycosylase/AP lyase activity makes to the maintenance of the genome is uncertain. The human gene encoding this enzyme was localized to the locus 16p13.2–3 by FISH analysis (FIG. 14). The accuracy of this localization was corroborated through the identification of genomic database nucleotide sequence (Acc. no. L48777) obtained by exon trapping from this same region of chromosome 16 [Burn, et al., *Gene* (Amst.), 161:183–187 (1995)]), which is 94.1% identical to nucleotides 699–799 of the sequence of FIG. 8. The chromosomal locus of human endonuclease III homologue is in very close proximity to that of another DNA base excision repair enzyme, 3-methylpurine DNA glycosylase, as well as the DNA nucleotide excision gene, ERCC-4. There is no apparent homology among these 3 proteins so it seems unlikely that their localization to the same chromosomal region is the result of gene duplication and divergence. Loss of heterozygosity in this region has been reported to occur in 22% of human hepatocellular carcinomas [Sakai, et al., *J. Gastroenterol. Hepatol.*, 7:288–292 (1992)]. Whether any or all of these DNA repair proteins act as tumor suppressors for human hepatocarcinogenesis remains to be determined.

Various references are cited throughout this specification, each of which is incorporated herein by reference in its entirety.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A mammalian endonuclease III purified greater than about 500-fold, which endonuclease III demonstrates pyrimidine hydrate DNA-glycosylase activity, thymine glycol DNA-glycosylase activity, and AP lyase activity, and reductively cross links with a thymine glycol containing oligodeoxynucleotide.

2. The endonuclease III of claim 1, wherein the endonuclease is purified greater than about 5000-fold.

3. The endonuclease III of claim 1, wherein the endonuclease in 100 mM NaCl elutes from a 1 ml single stranded-DNA-cellulose chromatography column eluted with a 12.5 ml gradient of 100 to 600 mM NaCl at 0.2 ml/min in about fractions 12–18.

4. The endonuclease III of claim 2 which elutes in about fractions 15–17.

5. The endonuclease III of claim 1 which has an apparent molecular weight of 29 kDa as determined by gel filtration.

6. The endonuclease III of claim 1 which has a predominant molecular weight of 31 kDa as determined by SDS-PAGE analysis.

7. The endonuclease III of claim 1 which has a partial amino acid sequence selected from the group consisting of SEQ ID NO:25, SEQ ID NO:26, SEQ ID NO:27, SEQ ID NO:28, SEQ ID NO:6, and SEQ ID NO:20.

8. The endonuclease III of claim 1 which has an amino acid sequence selected from the group consisting of bovine endonuclease III, human endonuclease III, and rat endonuclease III.

9. An endonuclease III having an amino acid sequence corresponding to SEQ ID NO:2.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
  ( A ) LENGTH: 1045 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:1:

```
AGTCCGGCAT GACCGCCTTG AGCGCGAGGA TGCTGACCCG GAGCCGGAGC CTGGGACCCG      60
GGGCTGGGCC GCGGGGGTGT AGGGAGGAGC CCGGGCCTCT CCGGAGAAGA GAGGCTGCAG     120
CAGAAGCGAG GAAAAGCCAC AGCCCCGTGA AGCGTCCGCG GAAAGCACAG AGACTGCGTG     180
TGGCCTATGA GGGCTCGGAC AGTGAGAAAG GTGAGGGGC  TGAGCCCCTC AAGGTGCCAG     240
TCTGGGAGCC CCAGGACTGG CAGCAACAGC TGGTCAACAT CCGTGCCATG AGGAACAAAA     300
AGGATGCACC TGTGGACCAT CTGGGGACTG AGCACTGCTA TGACTCCAGT GCCCCCCCAA     360
AGGTACGCAG GTACCAGGTG CTGCTGTCAC TGATGCTCTC CAGCCAAACC AAAGACCAGG     420
TGACGGCGGG CGCCATGCAG CGACTGCGGG CGCGGGGCCT GACGGTGGAC AGCATCCTGC     480
AGACAGATGA TGCCACGCTG GGCAAGCTCA TCTACCCCGT CGGTTTCTGG AGGAGCAAGG     540
TGAAATACAT CAAGCAGACC AGCGCCATCC TGCAGCAGCA CTACGGTGGG GACATCCCAG     600
CCTCTGTGGC CGAGCTGGTG GCGCTGCCGG GTGTTGGGCC AAGATGGCA  CACCTGGCTA     660
TGGCTGTGGC CTGGGGCACT GTGTCAGGCA TTGCAGTGGA CACGCATGTG CACAGAATCG     720
CCAACAGGCT GAGGTGGACC AAGAAGGCAA CCAAGTCCCC AGAGGAGACC CGCGCCGCCC     780
TGGAGGAGTG GCTGCCTAGG GAGCTGTGGC ACGAGATCAA TGGACTCTTG GTGGGCTTCG     840
GCCAGCAGAC CTGTCTGCCT GTGCACCCTC GCTGCCACGC CTGCCTCAAC CAAGCCCTCT     900
GCCCGGCCGC CCAGGGTCTC TGATGGCCGC ATGGCTCTGG CCGAGGTGCC GCTGTGGCCA     960
CCGTCTGTGA AGTGGCTTTA CGCTTCAGGA AGCCACGCCT GTTGAATAAA GCTTTGGTGT    1020
GTTTGCAAAA AAAAAAAAA  AAAAA                                          1045
```

( 2 ) INFORMATION FOR SEQ ID NO:2:

( i ) SEQUENCE CHARACTERISTICS:
    ( A ) LENGTH: 304 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:2:

```
Met Thr Ala Leu Ser Ala Arg Met Leu Thr Arg Ser Arg Ser Leu Gly
 1               5                  10                  15

Pro Gly Ala Gly Pro Arg Gly Cys Arg Glu Glu Pro Gly Pro Leu Arg
                20                  25                  30

Arg Arg Glu Ala Ala Ala Glu Ala Arg Lys Ser His Ser Pro Val Lys
```

|  |  |  | 35 |  |  |  | 40 |  |  |  | 45 |  |  |
|---|---|---|---|---|---|---|---|---|---|---|---|---|---|
| Arg | Pro 50 | Arg | Lys | Ala | Gln | Arg 55 | Leu | Arg | Val | Ala | Tyr 60 | Glu | Gly | Ser | Asp |
| Ser 65 | Glu | Lys | Gly | Glu | Gly 70 | Ala | Glu | Pro | Leu | Lys 75 | Val | Pro | Val | Trp | Glu 80 |
| Pro | Gln | Asp | Trp | Gln 85 | Gln | Gln | Leu | Val | Asn 90 | Ile | Arg | Ala | Met | Arg 95 | Asn |
| Lys | Lys | Asp | Ala 100 | Pro | Val | Asp | His | Leu 105 | Gly | Thr | Glu | His | Cys 110 | Tyr | Asp |
| Ser | Ser | Ala 115 | Pro | Pro | Lys | Val | Arg 120 | Arg | Tyr | Gln | Val | Leu 125 | Leu | Ser | Leu |
| Met | Leu 130 | Ser | Ser | Gln | Thr | Lys 135 | Asp | Gln | Val | Thr | Ala 140 | Gly | Ala | Met | Gln |
| Arg 145 | Leu | Arg | Ala | Arg | Gly 150 | Leu | Thr | Val | Asp | Ser 155 | Ile | Leu | Gln | Thr | Asp 160 |
| Asp | Ala | Thr | Leu | Gly 165 | Lys | Leu | Ile | Tyr | Pro 170 | Val | Gly | Phe | Trp | Arg 175 | Ser |
| Lys | Val | Lys | Tyr 180 | Ile | Lys | Gln | Thr | Ser 185 | Ala | Ile | Leu | Gln | Gln 190 | His | Tyr |
| Gly | Gly | Asp 195 | Ile | Pro | Ala | Ser | Val 200 | Ala | Glu | Leu | Val | Ala 205 | Leu | Pro | Gly |
| Val | Gly 210 | Pro | Lys | Met | Ala | His 215 | Leu | Ala | Met | Ala | Val 220 | Ala | Trp | Gly | Thr |
| Val 225 | Ser | Gly | Ile | Ala | Val 230 | Asp | Thr | His | Val | His 235 | Arg | Ile | Ala | Asn | Arg 240 |
| Leu | Arg | Trp | Thr | Lys 245 | Lys | Ala | Thr | Lys | Ser 250 | Pro | Glu | Glu | Thr | Arg 255 | Ala |
| Ala | Leu | Glu | Glu 260 | Trp | Leu | Pro | Arg | Glu 265 | Leu | Trp | His | Glu | Ile 270 | Asn | Gly |
| Leu | Leu | Val 275 | Gly | Phe | Gly | Gln | Gln 280 | Thr | Cys | Leu | Pro | Val 285 | His | Pro | Arg |
| Cys | His 290 | Ala | Cys | Leu | Asn | Gln 295 | Ala | Leu | Cys | Pro | Ala 300 | Ala | Gln | Gly | Leu |

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( v ) FRAGMENT TYPE:

( x i ) SEQUENCE DESCRIPTION: SEQ ID NO:3:

| Leu | Pro | Gly | Val | Gly |
|---|---|---|---|---|
| 1 |  |  |  | 5 |

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "Primer P1"

( i i i ) HYPOTHETICAL: NO ( x i ) SEQUENCE DESCRIPTION: SEQ ID NO:4:

GTGGCACGAG ATCAATGGAC TCTTG 25

( 2 ) INFORMATION FOR SEQ ID NO:5:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthesized oligo"

( i i i ) HYPOTHETICAL: NO ( x i ) SEQUENCE DESCRIPTION: SEQ ID NO:5:

CGCGATACGC C 11

( 2 ) INFORMATION FOR SEQ ID NO:6:

( i ) SEQUENCE CHARACTERISTICS:
    ( A ) LENGTH: 44 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Homo sapiens ( x i ) SEQUENCE DESCRIPTION: SEQ ID NO:6:

Trp Leu Pro Arg Xaa Leu Trp His Glu Ile Asn Gly Leu Leu Val Gly
1               5                   10                  15

Phe Gly Gln Gln Thr Cys Leu Pro Val His Pro Arg Cys His Ala Cys
                20                  25                  30

Leu Asn Gln Ala Leu Cys Pro Ala Ala Gln Gly Leu
            35                  40

( 2 ) INFORMATION FOR SEQ ID NO:7:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer P2"

( i i i ) HYPOTHETICAL: NO ( x i ) SEQUENCE DESCRIPTION: SEQ ID NO:7:

ATCATTGGAC TCTGGGTGGG C 21

( 2 ) INFORMATION FOR SEQ ID NO:8:

( i ) SEQUENCE CHARACTERISTICS:
    ( A ) LENGTH: 24 base pairs
    ( B ) TYPE: nucleic acid
    ( C ) STRANDEDNESS: single ( D ) TOPOLOGY: linear ( i i ) MOLECULE TYPE: other nucleic acid
( A ) DESCRIPTION: /desc = "Primer P3"

( i i i ) HYPOTHETICAL: NO ( x i ) SEQUENCE DESCRIPTION: SEQ ID NO:8:

CAACAGGCGT GGCTTCCTGA AGCG 24

( 2 ) INFORMATION FOR SEQ ID NO:9:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer P4"

( i i i ) HYPOTHETICAL: NO ( x i ) SEQUENCE DESCRIPTION: SEQ ID NO:9:

GGTGGGCTTC GGCCAGCAGA CCTGT 25

( 2 ) INFORMATION FOR SEQ ID NO:10:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer T7"

( i i i ) HYPOTHETICAL: NO ( x i ) SEQUENCE DESCRIPTION: SEQ ID NO:10:

TAATACGACT CACTACTATA GGAGA 25

( 2 ) INFORMATION FOR SEQ ID NO:11:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer SP6"

( i i i ) HYPOTHETICAL: NO ( x i ) SEQUENCE DESCRIPTION: SEQ ID NO:11:

AGCTATTTAG GTGACACTAT AG 22

( 2 ) INFORMATION FOR SEQ ID NO:12:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer P5"

( i i i ) HYPOTHETICAL: NO ( x i ) SEQUENCE DESCRIPTION: SEQ ID NO:12:

ACAGAGACTG CGTGTGGCCT ATGAG 25

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer P6"

(iii) HYPOTHETICAL: NO (xi) SEQUENCE DESCRIPTION: SEQ ID NO:13:

AAGAGAGCCT GCAGCAGAAG C 21

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer P7"

(iii) HYPOTHETICAL: NO (xi) SEQUENCE DESCRIPTION: SEQ ID NO:14:

CACCTTGCTC CAGAAACC 18

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer P8"

(iii) HYPOTHETICAL: NO (xi) SEQUENCE DESCRIPTION: SEQ ID NO:15:

CATCAGTGAC AGCAGCACCT 20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer P9"

(iii) HYPOTHETICAL: NO (xi) SEQUENCE DESCRIPTION: SEQ ID NO:16:

CATAGGCCAC ACGCAGTCTC 20

(2) INFORMATION FOR SEQ ID NO:17:

(i) SEQUENCE CHARACTERISTICS:
        (A) LENGTH: 21 base pairs (B) TYPE: nucleic acid
(C) STRANDEDNESS: single
(D) TOPOLOGY: linear (ii) MOLECULE TYPE: other nucleic acid
(A) DESCRIPTION: /desc = "Primer P10"

(iii) HYPOTHETICAL: NO (xi) SEQUENCE DESCRIPTION: SEQ ID NO:17:

CTTCTGCTGC AGCCTCTCTT C 21

(2) INFORMATION FOR SEQ ID NO:18:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Primer P11"

(iii) HYPOTHETICAL: NO (xi) SEQUENCE DESCRIPTION: SEQ ID NO:18:

CTTGGATCCA TGCTGACCCG GAGCCGGAGC 30

(2) INFORMATION FOR SEQ ID NO:19:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Primer P12"

(iii) HYPOTHETICAL: NO (xi) SEQUENCE DESCRIPTION: SEQ ID NO:19:

CTCGAATTCG AGCCATGCGG CCCTCCGAGA 30

(2) INFORMATION FOR SEQ ID NO:20:

(i) SEQUENCE CHARACTERISTICS:
(A) LENGTH: 70 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Rattus rattus (xi) SEQUENCE DESCRIPTION: SEQ ID NO:20:

| His | Arg | Ile | Ala | Asn | Arg | Leu | Lys | Trp | Thr | Lys | Lys | Met | Thr | Lys | Ser |
|---|---|---|---|---|---|---|---|---|---|---|---|---|---|---|---|
| 1 | | | | 5 | | | | | 10 | | | | | 15 | |

| Pro | Glu | Glu | Thr | Arg | Arg | Asn | Leu | Glu | Xaa | Trp | Leu | Pro | Arg | Val | Leu |
|---|---|---|---|---|---|---|---|---|---|---|---|---|---|---|---|
| | | | 20 | | | | | 25 | | | | | 30 | | |

| Trp | Ser | Glu | Ile | Asn | Gly | Leu | Leu | Val | Gly | Phe | Gly | Gln | Xaa | Ile | Cys |
|---|---|---|---|---|---|---|---|---|---|---|---|---|---|---|---|
| | | 35 | | | | | 40 | | | | | 45 | | | |

| Leu | Pro | Val | His | Pro | Arg | Cys | Gln | Ala | Cys | Leu | Xaa | Lys | Ala | Leu | Cys |
|---|---|---|---|---|---|---|---|---|---|---|---|---|---|---|---|
| | 50 | | | | | 55 | | | | | 60 | | | | |

```
     Pro Ala Ala Gln Gly Leu
     65                   70
```

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( v ) FRAGMENT TYPE:

( x i ) SEQUENCE DESCRIPTION: SEQ ID NO:21:

```
Cys Xaa Xaa Xaa Xaa Xaa Xaa Cys Xaa Xaa Cys Xaa Xaa Xaa Xaa Xaa
1                   5                   10                  15
Cys
```

( 2 ) INFORMATION FOR SEQ ID NO:22:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( v ) FRAGMENT TYPE:

( x i ) SEQUENCE DESCRIPTION: SEQ ID NO:22:

```
Cys Xaa Xaa Xaa Xaa Xaa Xaa Cys Xaa Xaa Cys Xaa Xaa Xaa Xaa Xaa
1                   5                   10                  15
Xaa Xaa Cys
```

( 2 ) INFORMATION FOR SEQ ID NO:23:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:23:

```
Cys Xaa Xaa Xaa Xaa Xaa Cys Xaa Xaa Cys Xaa Xaa Xaa Xaa Xaa Xaa
1                   5                   10                  15
Xaa Cys
```

( 2 ) INFORMATION FOR SEQ ID NO:24:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
      ( A ) ORGANISM: bovine ( x i ) SEQUENCE DESCRIPTION: SEQ ID NO:24:

Gly Glu Gly Gly Glu Gly Ala Glu His Leu Gln Ala Pro
   1               5                   10

( 2 ) INFORMATION FOR SEQ ID NO:25:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
      ( A ) ORGANISM: bovine ( x i ) SEQUENCE DESCRIPTION: SEQ ID NO:25:

Pro Val Asp Gln Leu Gly Ala Glu His Cys Phe Asp Pro Ser Ala
   1               5                   10                  15

( 2 ) INFORMATION FOR SEQ ID NO:26:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
      ( A ) ORGANISM: bovine ( x i ) SEQUENCE DESCRIPTION: SEQ ID NO:26:

Leu Thr Val Asp Ser Ile Leu Gln Thr Asp Asp Ser Thr Leu Gly Ala
   1               5                   10                  15

Leu Ile Val Pro Val Gly Phe
                   20

( 2 ) INFORMATION FOR SEQ ID NO:27:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
      ( A ) ORGANISM: bovine (x i) SEQUENCE DESCRIPTION: SEQ ID NO:27:

```
Gln Gly Thr Val Asn Gly Ile Ala Val Xaa Thr His Val Pro
1               5                   10
```

(2) INFORMATION FOR SEQ ID NO:28:

(i) SEQUENCE CHARACTERISTICS:
        (A) LENGTH: 22 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (v i) ORIGINAL SOURCE:
        (A) ORGANISM: bovine (x i) SEQUENCE DESCRIPTION: SEQ ID NO:28:

```
Leu Trp Ser Glu Ile Asn Gly Leu Leu Val Gly Phe Gly Gln Gln Thr
1               5                   10                  15

Cys Leu Pro Ile Arg Pro
                20
```

(2) INFORMATION FOR SEQ ID NO:29:

(i) SEQUENCE CHARACTERISTICS:
        (A) LENGTH: 207 amino acids
        (B) TYPE: amino acid
        (C) STRANDEDNESS: single
        (D) TOPOLOGY: linear (i i) MOLECULE TYPE: protein (i i i) HYPOTHETICAL: NO (v) FRAGMENT TYPE:

(v i) ORIGINAL SOURCE:
        (A) ORGANISM: Escherichia coli (x i) SEQUENCE DESCRIPTION: SEQ ID NO:29:

```
Met Asn Lys Ala Lys Arg Leu Glu Ile Leu Thr Arg Leu Arg Glu Asn
1               5                   10                  15

Asn Pro His Pro Thr Thr Glu Leu Asn Phe Ser Ser Pro Phe Glu Leu
                20                  25                  30

Leu Ile Ala Val Leu Leu Ser Ala Gln Ala Thr Asp Val Ser Val Asn
                35                  40                  45

Lys Ala Thr Ala Lys Leu Tyr Pro Val Ala Asn Thr Pro Ala Ala Met
        50                  55                  60

Leu Glu Leu Gly Val Glu Gly Val Lys Thr Tyr Ile Lys Thr Ile Gly
65                      70                  75                  80

Leu Tyr Asn Ser Lys Ala Glu Asn Ile Ile Lys Thr Cys Arg Ile Leu
                85                  90                  95

Leu Glu Gln His Asn Gly Glu Val Pro Glu Asp Arg Ala Ala Leu Glu
                100                 105                 110

Ala Leu Pro Gly Val Gly Arg Lys Thr Ala Asn Val Val Leu Asn Thr
            115                 120                 125

Ala Phe Gly Trp Pro Thr Ile Ala Val Asp Thr His Ile Phe Arg Val
            130                 135                 140

Cys Asn Arg Thr Gln Phe Ala Pro Gly Lys Asn Val Glu Gln Val Glu
145                 150                 155                 160
```

Glu    Lys    Leu    Leu    Lys    Val    Val    Pro    Ala    Glu    Phe    Lys    Val    Asp    Cys    His
                                            165                         170                                       175

His    Trp    Leu    Ile    Leu    His    Gly    Arg    Tyr    Thr    Cys    Ile    Ala    Arg    Lys    Pro
                                     180                         185                                       190

Arg    Cys    Gly    Ser    Cys    Ile    Ile    Glu    Asp    Leu    Cys    Glu    Tyr    Lys    Glu
                                     195                         200                         205

( 2 ) INFORMATION FOR SEQ ID NO:30:

( i ) SEQUENCE CHARACTERISTICS:
            ( A ) LENGTH: 207 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
            ( A ) ORGANISM: Haemophilus influenzae ( x i ) SEQUENCE DESCRIPTION: SEQ ID NO:30:

Met    Asn    Lys    Thr    Lys    Arg    Ile    Glu    Ile    Leu    Thr    Arg    Leu    Arg    Glu    Gln
                1                           5                           10                                       15

Asn    Pro    His    Pro    Thr    Thr    Glu    Leu    Gln    Tyr    Asn    Ser    Pro    Phe    Glu    Leu
                                     20                          25                                 30

Leu    Ile    Ala    Val    Ile    Leu    Ser    Ala    Gln    Ala    Thr    Asp    Lys    Gly    Val    Asn
                                     35                          40                          45

Lys    Ala    Thr    Glu    Lys    Leu    Phe    Pro    Val    Ala    Asn    Thr    Pro    Gln    Ala    Ile
                       50                          55                                 60

Leu    Asp    Leu    Gly    Leu    Asp    Gly    Leu    Lys    Ser    Tyr    Ile    Lys    Thr    Ile    Gly
                65                                 70                          75                                       80

Leu    Phe    Asn    Ser    Lys    Ala    Glu    Asn    Ile    Ile    Lys    Thr    Cys    Arg    Asp    Leu
                                            85                          90                                       95

Ile    Glu    Lys    His    Asn    Gly    Glu    Val    Pro    Glu    Asn    Arg    Glu    Ala    Leu    Glu
                                     100                         105                                110

Ala    Leu    Ala    Gly    Val    Gly    Arg    Lys    Thr    Ala    Asn    Val    Val    Leu    Asn    Thr
                                     115                         120                                125

Ala    Phe    Gly    His    Pro    Thr    Ile    Ala    Val    Asp    Thr    His    Ile    Phe    Arg    Val
                              130                                135                         140

Cys    Asn    Arg    Thr    Asn    Phe    Ala    Ala    Gly    Lys    Asp    Val    Val    Lys    Val    Glu
                145                                 150                         155                                       160

Glu    Lys    Leu    Leu    Lys    Val    Val    Pro    Asn    Glu    Phe    Lys    Val    Asp    Val    His
                                            165                         170                                       175

His    Trp    Leu    Ile    Leu    His    Gly    Arg    Tyr    Thr    Cys    Ile    Ala    Arg    Lys    Pro
                                     180                         185                                       190

Arg    Cys    Gly    Ser    Cys    Ile    Ile    Glu    Asp    Leu    Cys    Glu    Tyr    Lys    Glu
                                     195                         200                         205

( 2 ) INFORMATION FOR SEQ ID NO:31:

( i ) SEQUENCE CHARACTERISTICS:
            ( A ) LENGTH: 209 amino acids
            ( B ) TYPE: amino acid
            ( C ) STRANDEDNESS: single
            ( D ) TOPOLOGY: linear ( i i ) MOLECULE TYPE: protein (iii) HYPOTHETICAL: NO (v) FRAGMENT TYPE: N-terminal (vi) ORIGINAL SOURCE:
(A) ORGANISM: Bacillus subtilis (xi) SEQUENCE DESCRIPTION: SEQ ID NO:31:

| Met | Leu | Asn | Leu | Lys | Gln | Ile | Glu | Phe | Cys | Leu | Asp | Lys | Ile | Gly | Asp |
|---|---|---|---|---|---|---|---|---|---|---|---|---|---|---|---|
| 1 | | | | 5 | | | | | 10 | | | | | 15 | |
| Met | Phe | Pro | His | Ala | Glu | Cys | Glu | Leu | Val | His | Ser | Asn | Pro | Phe | Glu |
| | | | 20 | | | | | 25 | | | | | 30 | | |
| Leu | Val | Val | Ala | Val | Ala | Leu | Ser | Ala | Gln | Cys | Thr | Asp | Ala | Leu | Val |
| | | | 35 | | | | 40 | | | | | 45 | | | |
| Asn | Arg | Val | Thr | Lys | Thr | Leu | Phe | Gln | Lys | Tyr | Lys | Arg | Pro | Glu | Asp |
| | | | 50 | | | | 55 | | | | | 60 | | | |
| Tyr | Leu | Ala | Val | Pro | Leu | Glu | Glu | Leu | Gln | Gln | Asp | Ile | Lys | Ser | Ile |
| 65 | | | | | 70 | | | | | 75 | | | | | 80 |
| Gly | Leu | Tyr | Arg | Asn | Lys | Ala | Lys | Asn | Ile | Gln | Lys | Leu | Ser | Lys | Met |
| | | | | 85 | | | | | 90 | | | | | 95 | |
| Ile | Ile | Glu | Asp | Tyr | Gly | Gly | Glu | Val | Pro | Arg | Asp | Arg | Asp | Glu | Leu |
| | | | 100 | | | | | 105 | | | | | 110 | | |
| Val | Lys | Leu | Pro | Gly | Val | Gly | Arg | Lys | Thr | Ala | Asn | Val | Val | Val | Ser |
| | | | 115 | | | | | 120 | | | | | 125 | | |
| Val | Ala | Phe | Gly | Val | Pro | Ala | Ile | Ala | Val | Asp | Thr | His | Val | Glu | Arg |
| | | | 130 | | | | | 135 | | | | | 140 | | |
| Val | Ser | Lys | Arg | Leu | Gly | Ile | Cys | Arg | Trp | Lys | Asp | Ser | Val | Leu | Glu |
| 145 | | | | | 150 | | | | | 155 | | | | | 160 |
| Val | Glu | Lys | Thr | Leu | Met | Arg | Lys | Val | Pro | Lys | Glu | Asp | Trp | Ser | Val |
| | | | | 165 | | | | | 170 | | | | | 175 | |
| Thr | His | His | Arg | Leu | Ile | Phe | Phe | Gly | Arg | Tyr | His | Cys | Lys | Ala | Gln |
| | | | 180 | | | | | 185 | | | | | 190 | | |
| Ser | Pro | Arg | Cys | Ala | Glu | Cys | Pro | Leu | Leu | Ser | Leu | Cys | Arg | Glu | Gly |
| | | | 195 | | | | | 200 | | | | | 205 | | |
| Gln | | | | | | | | | | | | | | | |

(2) INFORMATION FOR SEQ ID NO:32:

(i) SEQUENCE CHARACTERISTICS:
(A) LENGTH: 204 amino acids
(B) TYPE: amino acid
(C) STRANDEDNESS: single
(D) TOPOLOGY: linear (ii) MOLECULE TYPE: protein (iii) HYPOTHETICAL: NO (v) FRAGMENT TYPE: N-terminal (vi) ORIGINAL SOURCE:
(A) ORGANISM: M. jannaschii (xi) SEQUENCE DESCRIPTION: SEQ ID NO:32:

| Met | Leu | Asn | Val | Ile | Leu | Leu | Lys | Lys | Leu | Asn | Lys | Asn | Ala | Val | Val |
|---|---|---|---|---|---|---|---|---|---|---|---|---|---|---|---|
| 1 | | | | 5 | | | | | 10 | | | | | 15 | |
| Thr | Glu | Ile | Ala | Lys | Asp | Lys | Asp | Pro | Phe | Lys | Val | Leu | Ile | Ser | Thr |
| | | | 20 | | | | | 25 | | | | | 30 | | |
| Ile | Ile | Ser | Ala | Arg | Thr | Lys | Asp | Glu | Val | Thr | Glu | Glu | Val | Ser | Lys |
| | | | 35 | | | | | 40 | | | | | 45 | | |
| Lys | Leu | Phe | Lys | Glu | Ile | Lys | Asp | Val | Asp | Asp | Leu | Leu | Asn | Ile | Asp |

|  |  |  |  |  | 50 |  |  |  |  | 55 |  |  |  |  | 60 |  |  |
|---|---|---|---|---|---|---|---|---|---|---|---|---|---|---|---|---|---|
| Glu 65 | Glu | Lys | Leu | Ala | Asp 70 | Leu | Ile | Tyr | Pro | Ala 75 | Gly | Phe | Tyr | Lys | Asn 80 | | |
| Lys | Ala | Lys | Asn | Leu 85 | Lys | Lys | Leu | Ala | Lys 90 | Ile | Leu | Lys | Glu | Asn 95 | Tyr | | |
| Asn | Gly | Lys | Val | Pro 100 | Asp | Ser | Leu | Glu | Glu 105 | Leu | Leu | Lys | Leu | Pro 110 | Gly | | |
| Val | Gly | Arg 115 | Lys | Thr | Ala | Asn | Leu 120 | Val | Ile | Thr | Leu | Ala 125 | Phe | Asn | Lys | | |
| Asp | Gly 130 | Ile | Cys | Val | Asp | Thr 135 | His | Val | His | Arg | Ile 140 | Cys | Asn | Arg | Trp | | |
| Glu 145 | Ile | Val | Asp | Thr | Glu 150 | Thr | Pro | Glu | Glu | Thr 155 | Glu | Phe | Glu | Leu | Arg 160 | | |
| Lys | Lys | Leu | Pro | Lys 165 | Lys | Tyr | Trp | Lys | Val 170 | Ile | Asn | Asn | Leu | Leu 175 | Val | | |
| Val | Phe | Gly | Arg 180 | Glu | Ile | Cys | Ser | Ser 185 | Lys | Ser | Lys | Cys | Asp 190 | Lys | Cys | | |
| Phe | Lys | Glu 195 | Ile | Lys | Glu | Lys | Cys 200 | Pro | Tyr | Tyr | Glu | | | | | | |

( 2 ) INFORMATION FOR SEQ ID NO:33:

( i ) SEQUENCE CHARACTERISTICS:
    ( A ) LENGTH: 231 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
    ( A ) ORGANISM: S. cerevisiae ( x i ) SEQUENCE DESCRIPTION: SEQ ID NO:33:

| Arg 1 | Leu | Met | Arg | Ser 5 | Lys | Val | Lys | Thr | Pro 10 | Val | Asp | Ala | Met | Gly 15 | Cys |
|---|---|---|---|---|---|---|---|---|---|---|---|---|---|---|---|
| Ser | Met | Ile | Pro 20 | Val | Leu | Val | Ser | Asn 25 | Lys | Cys | Gly | Ile | Pro 30 | Ser | Glu |
| Lys | Val | Asp 35 | Pro | Lys | Asn | Phe | Arg 40 | Leu | Gln | Phe | Leu | Ile 45 | Gly | Thr | Met |
| Leu | Ser 50 | Ala | Gln | Thr | Arg | Asp 55 | Glu | Arg | Met | Ala | Gln 60 | Ala | Ala | Leu | Asn |
| Ile 65 | Thr | Glu | Tyr | Cys | Leu 70 | Asn | Thr | Leu | Lys | Ile 75 | Ala | Glu | Gly | Ile | Thr 80 |
| Leu | Asp | Gly | Leu | Leu 85 | Lys | Ile | Asp | Glu | Pro 90 | Val | Leu | Ala | Asn | Leu 95 | Ile |
| Arg | Cys | Val | Ser | Phe 100 | Tyr | Thr | Arg | Lys | Ala 105 | Asn | Phe | Ile | Lys | Arg 110 | Thr |
| Ala | Gln | Leu | Leu 115 | Val | Asp | Asn | Phe | Asp 120 | Ser | Asp | Ile | Pro | Tyr 125 | Asp | Ile |
| Glu | Gly 130 | Ile | Leu | Ser | Leu | Pro 135 | Gly | Val | Gly | Pro | Lys 140 | Met | Gly | Tyr | Leu |
| Thr 145 | Leu | Gln | Lys | Gly | Trp 150 | Gly | Leu | Ile | Ala | Gly 155 | Ile | Cys | Val | Asp | Val 160 |
| His | Val | His | Arg | Leu | Cys | Lys | Met | Trp | Asn | Trp | Val | Asp | Pro | Ile | Lys |

|     | 165 |     |     |     |     | 170 |     |     |     |     | 175 |     |     |
| --- | --- | --- | --- | --- | --- | --- | --- | --- | --- | --- | --- | --- | --- |
| Cys | Lys | Thr | Ala<br>180 | Glu | His | Thr | Arg | Lys<br>185 | Glu | Leu | Gln | Val | Trp<br>190 | Leu | Pro |

Cys Lys Thr Ala Glu His Thr Arg Lys Glu Leu Gln Val Trp Leu Pro
                180                   185                   190

His Ser Leu Trp Tyr Glu Ile Asn Thr Val Leu Val Gly Phe Gly Gln
        195                 200                 205

Leu Ile Cys Met Ala Arg Gly Lys Arg Cys Asp Leu Cys Leu Ala Asn
        210                 215                 220

Asp Val Cys Asn Ala Arg Asn
225                 230

( 2 ) INFORMATION FOR SEQ ID NO:34:

( i ) SEQUENCE CHARACTERISTICS:
        ( A ) LENGTH: 230 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: S. cerevisiae
        ( B ) STRAIN: Sce nFe-S ( x i ) SEQUENCE DESCRIPTION: SEQ ID NO:34:

Arg Val Leu Arg Ser Lys Ile Leu Ala Pro Val Asp Ile Ile Gly Gly
1                   5                   10                  15

Ser Ser Ile Pro Val Thr Val Ala Ser Lys Cys Gly Ile Ser Lys Glu
            20                  25                  30

Gln Ile Ser Pro Arg Asp Tyr Arg Leu Gln Val Leu Leu Gly Val Met
        35                  40                  45

Leu Ser Ser Gln Thr Lys Asp Glu Val Thr Ala Met Ala Met Leu Asn
    50                  55                  60

Ile Met Arg Tyr Cys Ile Asp Glu Leu His Ser Glu Glu Gly Met Thr
65                  70                  75                  80

Leu Glu Ala Val Leu Gln Ile Asn Glu Thr Lys Leu Asp Glu Leu Ile
                85                  90                  95

His Ser Val Gly Phe His Thr Arg Lys Ala Lys Tyr Ile Leu Ser Thr
            100                 105                 110

Cys Lys Ile Leu Gln Asp Gln Phe Ser Ser Asp Val Pro Ala Thr Ile
        115                 120                 125

Asn Glu Leu Leu Gly Leu Pro Gly Val Gly Pro Lys Met Ala Tyr Leu
    130                 135                 140

Thr Leu Gln Lys Ala Trp Gly Lys Ile Glu Gly Ile Cys Val Asp Val
145                 150                 155                 160

His Val Asp Arg Leu Thr Lys Leu Trp Lys Trp Val Asp Ala Gln Lys
                165                 170                 175

Cys Lys Thr Pro Asp Gln Thr Arg Thr Gln Leu Gln Asn Trp Leu Pro
            180                 185                 190

Lys Gly Leu Trp Thr Glu Ile Asn Gly Leu Leu Val Gly Phe Gly Gln
        195                 200                 205

Ile Ile Thr Lys Ser Arg Asn Leu Gly Asp Met Leu Gln Phe Leu Pro
    210                 215                 220

Pro Asp Asp Pro Gly Gly
225                 230

(2) INFORMATION FOR SEQ ID NO:35:

(i) SEQUENCE CHARACTERISTICS:
        (A) LENGTH: 213 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (vi) ORIGINAL SOURCE:
        (A) ORGANISM: S. pombe (xi) SEQUENCE DESCRIPTION: SEQ ID NO:35:

```
Cys Lys Met Lys Ala Lys Val Val Ala Pro Val Asp Val Gln Gly Cys
 1               5                  10                  15
His Thr Leu Gly Glu Arg Asn Asp Pro Lys Lys Phe Arg Phe Gln Thr
            20                  25                  30
Leu Val Ala Leu Met Leu Ser Ser Gln Thr Lys Asp Ile Val Leu Gly
        35                  40                  45
Pro Thr Met Arg Asn Leu Lys Glu Lys Leu Ala Gly Gly Leu Cys Leu
    50                  55                  60
Glu Asp Ile Gln Asn Ile Asp Glu Val Ser Leu Asn Lys Leu Ile Glu
65                  70                  75                  80
Lys Val Gly Phe His Asn Arg Lys Thr Ile Tyr Leu Lys Gln Met Ala
                85                  90                  95
Arg Ile Leu Ser Glu Lys Phe Gln Gly Asp Ile Pro Asp Thr Val Glu
            100                 105                 110
Asp Leu Met Thr Leu Pro Gly Val Gly Pro Lys Met Gly Tyr Leu Cys
            115                 120                 125
Met Ser Ile Ala Trp Asn Lys Thr Val Gly Ile Gly Val Asp Val His
    130                 135                 140
Val His Arg Ile Cys Asn Leu Leu His Trp Cys Asn Thr Lys Thr Glu
145                 150                 155                 160
Glu Gln Thr Arg Ala Ala Leu Gln Ser Trp Leu Pro Lys Glu Leu Trp
                165                 170                 175
Phe Glu Leu Asn His Thr Leu Val Gly Phe Gly Gln Thr Ile Cys Leu
            180                 185                 190
Pro Arg Gly Arg Arg Cys Asp Met Cys Thr Leu Ser Ser Lys Gly Leu
            195                 200                 205
Cys Pro Ser Ala Phe
    210
```

(2) INFORMATION FOR SEQ ID NO:36:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (vi) ORIGINAL SOURCE:
        (A) ORGANISM: Escherichia coli ( x i ) SEQUENCE DESCRIPTION: SEQ ID NO:36:

| Met | Arg | Lys | Asp | Met | Ile | Ala | Pro | Val | Asp | Thr | Met | Gly | Cys | His | Lys |
|---|---|---|---|---|---|---|---|---|---|---|---|---|---|---|---|
| 1 | | | | 5 | | | | | 10 | | | | | | 15 |

| Leu | Ala | Asp | Pro | Leu | Ala | Ala | Pro | Pro | Val | His | Arg | Phe | Gln | Val | Leu |
| | | | 20 | | | | | 25 | | | | | 30 | | |

| Val | Ala | Leu | Met | Leu | Ser | Ser | Gln | Thr | Arg | Asp | Glu | Val | Asn | Ala | Ala |
| | | 35 | | | | | 40 | | | | | 45 | | | |

| Ala | Met | Lys | Arg | Leu | Lys | Asp | His | Gly | Leu | Ser | Ile | Gly | Lys | Ile | Leu |
| | 50 | | | | | 55 | | | | | 60 | | | | |

| Glu | Phe | Lys | Val | Pro | Asp | Leu | Glu | Thr | Ile | Leu | Cys | Pro | Val | Gly | Phe |
| 65 | | | | | 70 | | | | | 75 | | | | | 80 |

| Tyr | Lys | Arg | Lys | Ala | Val | Tyr | Leu | Gln | Lys | Thr | Ala | Lys | Ile | Leu | Lys |
| | | | | 85 | | | | | 90 | | | | | | 95 |

| Asp | Asp | Phe | Ser | Gly | Asp | Ile | Pro | Asp | Ser | Leu | Asp | Gly | Leu | Cys | Ala |
| | | | | 100 | | | | | 105 | | | | | 110 | |

| Leu | Pro | Gly | Val | Gly | Pro | Lys | Met | Ala | Asn | Leu | Val | Met | Gln | Ile | Ala |
| | | | 115 | | | | | 120 | | | | | 125 | | |

| Trp | Gly | Glu | Cys | Val | Gly | Ile | Ala | Val | Asp | Thr | His | Val | His | Arg | Ile |
| | | 130 | | | | | 135 | | | | | 140 | | | |

| Ser | Asn | Arg | Leu | Gly | Trp | Ile | Lys | Thr | Ser | Thr | Pro | Glu | Lys | Thr | Gln |
| 145 | | | | | 150 | | | | | 155 | | | | | 160 |

| Lys | Ala | Leu | Glu | Ile | Leu | Leu | Pro | Lys | Ser | Glu | Trp | Gln | Pro | Ile | Asn |
| | | | | 165 | | | | | 170 | | | | | 175 | |

| His | Leu | Leu | Val | Gly | Phe | Gly | Gln | Met | Gln | Cys | Gln | Pro | Val | Arg | Pro |
| | | | 180 | | | | | 185 | | | | | 190 | | |

| Lys | Cys | Gly | Thr | Cys | Leu | Cys | Arg | Phe | Thr | Cys | Pro | Ser | Ser | Thr | |
| | | 195 | | | | | 200 | | | | | 205 | | | |

( 2 ) INFORMATION FOR SEQ ID NO:37:

( i ) SEQUENCE CHARACTERISTICS:
        ( A ) LENGTH: 211 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:37:

| Arg | Ala | Met | Arg | Asn | Lys | Lys | Asp | Ala | Pro | Val | Asp | His | Leu | Gly | Thr |
|---|---|---|---|---|---|---|---|---|---|---|---|---|---|---|---|
| 1 | | | | 5 | | | | | 10 | | | | | | 15 |

| Glu | His | Cys | Tyr | Asp | Ser | Ser | Ala | Pro | Pro | Lys | Val | Arg | Arg | Tyr | Gln |
| | | | 20 | | | | | 25 | | | | | 30 | | |

| Val | Leu | Leu | Ser | Leu | Met | Leu | Ser | Ser | Gln | Thr | Lys | Asp | Gln | Val | Thr |
| | | | 35 | | | | | 40 | | | | | 45 | | |

| Ala | Gly | Ala | Met | Gln | Arg | Leu | Arg | Ala | Arg | Gly | Leu | Thr | Val | Asp | Ser |
| | | 50 | | | | | 55 | | | | | 60 | | | |

| Ile | Leu | Gln | Thr | Asp | Asp | Ala | Thr | Leu | Gly | Lys | Leu | Ile | Tyr | Pro | Val |
| 65 | | | | | 70 | | | | | 75 | | | | | 80 |

| Gly | Phe | Trp | Arg | Ser | Lys | Val | Lys | Tyr | Ile | Lys | Gln | Thr | Ser | Ala | Ile |
| | | | | 85 | | | | | 90 | | | | | 95 | |

| Leu | Gln | Gln | His | Tyr | Gly | Gly | Asp | Ile | Pro | Ala | Ser | Val | Ala | Glu | Leu |

|     |     |     |     | 100 |     |     |     | 105 |     |     |     | 110 |     |     |
|-----|-----|-----|-----|-----|-----|-----|-----|-----|-----|-----|-----|-----|-----|-----|
| Val | Ala | Leu | Pro | Gly | Val | Gly | Pro | Lys | Met | Ala | His | Leu | Ala | Met | Ala |
|     |     | 115 |     |     |     |     | 120 |     |     |     |     | 125 |     |     |     |
| Val | Ala | Trp | Gly | Thr | Val | Ser | Gly | Ile | Ala | Val | Asp | Thr | His | Val | His |
|     |     | 130 |     |     |     | 135 |     |     |     |     | 140 |     |     |     |     |
| Arg | Ile | Ala | Asn | Arg | Leu | Arg | Trp | Thr | Lys | Lys | Ala | Thr | Lys | Ser | Pro |
| 145 |     |     |     |     | 150 |     |     |     |     | 155 |     |     |     |     | 160 |
| Glu | Glu | Thr | Arg | Ala | Ala | Leu | Glu | Glu | Trp | Leu | Pro | Arg | Glu | Leu | Trp |
|     |     |     |     | 165 |     |     |     |     | 170 |     |     |     |     | 175 |     |
| His | Glu | Ile | Asn | Gly | Leu | Leu | Val | Gly | Phe | Gly | Gln | Gln | Thr | Cys | Leu |
|     |     |     | 180 |     |     |     |     | 185 |     |     |     |     | 190 |     |     |
| Pro | Val | His | Pro | Arg | Cys | His | Ala | Cys | Leu | Asn | Gln | Ala | Leu | Cys | Pro |
|     |     | 195 |     |     |     |     | 200 |     |     |     |     | 205 |     |     |     |
| Ala | Ala | Gln |
|     |     | 210 |

(2) INFORMATION FOR SEQ ID NO:38:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (vi) ORIGINAL SOURCE:
        (A) ORGANISM: Escherichia coli (xi) SEQUENCE DESCRIPTION: SEQ ID NO:38:

| Met | Asn | Lys | Ala | Lys | Arg | Leu | Glu | Ile | Leu | Thr | Arg | Leu | Arg | Glu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Pro | His | Pro | Thr | Thr | Glu | Leu | Asn | Phe | Ser | Ser | Pro | Phe | Glu | Leu |
|     |     |     | 20  |     |     |     |     | 25  |     |     |     |     | 30  |     |     |
| Leu | Ile | Ala | Val | Leu | Leu | Ser | Ala | Gln | Ala | Thr | Asp | Val | Ser | Val | Asn |
|     |     |     | 35  |     |     |     |     | 40  |     |     |     |     | 45  |     |     |
| Lys | Ala | Thr | Ala | Lys | Leu | Tyr | Pro | Val | Ala | Asn | Thr | Pro | Ala | Ala | Met |
|     |     | 50  |     |     |     |     | 55  |     |     |     |     | 60  |     |     |     |
| Leu | Glu | Leu | Gly | Val | Glu | Gly | Val | Lys | Thr | Tyr | Ile | Lys | Thr | Ile | Gly |
| 65  |     |     |     |     | 70  |     |     |     |     | 75  |     |     |     |     | 80  |
| Leu | Tyr | Asn | Ser | Lys | Ala | Glu | Asn | Ile | Ile | Lys | Thr | Cys | Arg | Ile | Leu |
|     |     |     |     | 85  |     |     |     |     | 90  |     |     |     |     | 95  |     |
| Leu | Glu | Gln | His | Asn | Gly | Glu | Val | Pro | Glu | Asp | Arg | Ala | Ala | Leu | Glu |
|     |     |     |     | 100 |     |     |     |     | 105 |     |     |     |     | 110 |     |
| Ala | Leu | Pro | Gly | Val | Gly | Arg | Lys | Thr | Ala | Asn | Val | Val | Leu | Asn | Thr |
|     |     |     |     | 115 |     |     |     |     | 120 |     |     |     |     | 125 |     |
| Ala | Phe | Gly | Trp | Pro | Thr | Ile | Ala | Val | Asp | Thr | His | Ile | Phe | Arg | Val |
|     |     | 130 |     |     |     |     | 135 |     |     |     |     | 140 |     |     |     |
| Cys | Asn | Arg | Thr | Gln | Phe | Ala | Pro | Gly | Lys | Asn | Val | Glu | Gln | Val | Glu |
| 145 |     |     |     |     | 150 |     |     |     |     | 155 |     |     |     |     | 160 |
| Glu | Lys | Leu | Leu | Lys | Val | Val | Pro | Ala | Glu | Phe | Lys | Val | Asp | Cys | His |
|     |     |     |     | 165 |     |     |     |     | 170 |     |     |     |     | 175 |     |
| His | Trp | Leu | Ile | Leu | His | Gly | Arg | Tyr | Thr | Cys | Ile | Ala | Arg | Lys | Pro |
|     |     |     | 180 |     |     |     |     | 185 |     |     |     |     | 190 |     |     |
| Arg | Cys | Gly | Ser | Cys | Ile | Ile | Glu | Asp | Leu | Cys | Glu | Tyr | Lys | Glu | Lys |

195 200 205

Val Asp Ile
210

( 2 ) INFORMATION FOR SEQ ID NO:39:

( i ) SEQUENCE CHARACTERISTICS:
( A ) LENGTH: 259 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: C. elegans ( x i ) SEQUENCE DESCRIPTION: SEQ ID NO:39:

```
Met Arg Lys Asp Met Ile Ala Pro Val Asp Thr Met Gly Cys His Lys
1               5                   10                  15

Leu Ala Asp Pro Leu Ala Ala Pro Pro Val His Arg Phe Gln Val Leu
            20              25                  30

Val Ala Leu Met Leu Ser Ser Gln Thr Arg Asp Glu Val Asn Ala Ala
        35                  40                  45

Ala Met Lys Arg Leu Lys Asp His Gly Leu Ser Ile Gly Lys Ile Leu
    50                  55                  60

Glu Phe Lys Val Pro Asp Leu Glu Thr Ile Leu Cys Pro Val Gly Phe
65                  70                  75                  80

Tyr Lys Arg Lys Ala Val Tyr Leu Gln Lys Thr Ala Lys Ile Leu Lys
                85                  90                  95

Asp Asp Phe Ser Gly Asp Ile Pro Asp Ser Leu Asp Gly Leu Cys Ala
            100                 105                 110

Leu Pro Gly Val Gly Pro Lys Met Ala Asn Leu Val Met Gln Ile Ala
        115                 120                 125

Trp Gly Glu Cys Val Gly Ile Ala Val Asp Thr His Val His Arg Ile
    130                 135                 140

Ser Asn Arg Leu Gly Trp Ile Lys Thr Ser Thr Pro Glu Lys Thr Gln
145                 150                 155                 160

Lys Ala Leu Glu Ile Leu Leu Pro Lys Ser Glu Trp Gln Pro Ile Asn
                165                 170                 175

His Leu Leu Val Gly Phe Gly Gln Met Gln Cys Gln Pro Val Arg Pro
            180                 185                 190

Lys Cys Gly Thr Cys Leu Cys Arg Phe Thr Cys Pro Ser Ser Thr Ala
        195                 200                 205

Lys Asn Val Lys Ser Glu Thr Glu Glu Thr Ser Thr Ser Ile Glu Val
    210                 215                 220

Lys Gln Glu Val Glu Asp Glu Phe Glu Asp Glu Lys Pro Ala Lys Lys
225                 230                 235                 240

Ile Lys Lys Thr Arg Lys Thr Arg Thr Lys Ile Glu Val Lys Thr Glu
                245                 250                 255

Ser Glu Thr
```

( 2 ) INFORMATION FOR SEQ ID NO:40:

( i ) SEQUENCE CHARACTERISTICS:
( A ) LENGTH: 1046 base pairs (B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:40:

| | | | | | | |
|---|---|---|---|---|---|---|
| CCCACGCGTC | CCGCCGCCTT | GAGCGCGAGG | ATGCTGACCC | GGAGCCGGAG | CCTGGGACCC | 60 |
| GGGGCTGGGC | CGCGGGGGTG | TAGGGAGGAG | CCCGGGCCTC | TCCGGAGAAG | AGAGGCTGCA | 120 |
| GCAGAAGCGA | GGAAAAGCCA | CAGCCCCGTG | AAGCGTCCGC | GGAAAGCACA | GAGACTGCGT | 180 |
| GTGGCCTATG | AGGGCTCGGA | CAGTGAGAAA | GGTGAGGGGG | CTGAGCCCCT | CAAGGTGCCA | 240 |
| GTCTGGGAGC | CCCAGGACTG | GCAGCAACAG | CTGGTCAACA | TCCGTGCCAT | GAGGAACAAA | 300 |
| AAGGATGCAC | CTGTGGACCA | TCTGGGGACT | GAGCACTGCT | ATGACTCCAG | TGCCCCCCA | 360 |
| AAGGTACGCA | GGTACCAGGT | GCTGCTGTCA | CTGATGCTCT | CCAGCCAAAC | CAAAGACCAG | 420 |
| GTGACGGCGG | GCGCCATGCA | GCGACTGCGG | GCGCGGGGCC | TGACGGTGGA | CAGCATCCTG | 480 |
| CAGACAGATG | ATGCCACGCT | GGGCAAGCTC | ATCTACCCCG | TCGGTTTCTG | GAGGAGCAAG | 540 |
| GTGAAATACA | TCAAGCAGAC | CAGCGCCATC | CTGCAGCAGC | ACTACGGTGG | GGACATCCCA | 600 |
| GCCTCTGTGG | CCGAGCTGGT | GGCGCTGCCG | GGTGTTGGGC | CCAAGATGGC | ACACCTGGCT | 660 |
| ATGGCTGTGG | CCTGGGGCAC | TGTGTCAGGC | ATTGCAGTGG | ACACGCATGT | GCACAGAATC | 720 |
| GCCAACAGGC | TGAGGTGGAC | CAAGAAGGCA | ACCAAGTCCC | CAGAGGAGAC | CCGCGCCGCC | 780 |
| CTGGAGGAGT | GGCTGCCTAG | GGAGCTGTGG | CACGAGATCA | ATGGACTCTT | GGTGGGCTTC | 840 |
| GGCCAGCAGA | CCTGTCTGCC | TGTGCACCCT | CGCTGCCACG | CCTGCCTCAA | CCAAGCCCTC | 900 |
| TGCCCGGCCG | CCCAGGGTCT | CTGATGGCCG | CATGGCTCTG | GCCGAGGTGC | CGCTGTGGCC | 960 |
| ACCGTCTGTG | AAGTGGCTTT | ACGCTTCAGG | AAGCCACGCC | TGTTGAATAA | AGCTTTGGTG | 1020 |
| TGTTTGCAAA | AAAAAAAAAA | AAAAAA | | | | 1046 |

(2) INFORMATION FOR SEQ ID NO:41:

(i) SEQUENCE CHARACTERISTICS:
    (A) LENGTH: 894 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:41:

| | | | | | | |
|---|---|---|---|---|---|---|
| ATGCTGACCC | GGAGCCGGAG | CCTGGGACCC | GGGGCTGGGC | CGCGGGGGTG | TAGGGAGGAG | 60 |
| CCCGGGCCTC | TCCGGAGAAG | AGAGGCTGCA | GCAGAAGCGA | GGAAAAGCCA | CAGCCCCGTG | 120 |
| AAGCGTCCGC | GGAAAGCACA | GAGACTGCGT | GTGGCCTATG | AGGGCTCGGA | CAGTGAGAAA | 180 |
| GGTGAGGGGG | CTGAGCCCCT | CAAGGTGCCA | GTCTGGGAGC | CCCAGGACTG | GCAGCAACAG | 240 |
| CTGGTCAACA | TCCGTGCCAT | GAGGAACAAA | AAGGATGCAC | CTGTGGACCA | TCTGGGGACT | 300 |

```
GAGCACTGCT  ATGACTCCAG  TGCCCCCCCA  AAGGTACGCA  GGTACCAGGT  GCTGCTGTCA    360

CTGATGCTCT  CCAGCCAAAC  CAAAGACCAG  GTGACGGCGG  GCGCCATGCA  GCGACTGCGG    420

GCGCGGGGCC  TGACGGTGGA  CAGCATCCTG  CAGACAGATG  ATGCCACGCT  GGGCAAGCTC    480

ATCTACCCCG  TCGGTTTCTG  GAGGAGCAAG  GTGAAATACA  TCAAGCAGAC  CAGCGCCATC    540

CTGCAGCAGC  ACTACGGTGG  GGACATCCCA  GCCTCTGTGG  CCGAGCTGGT  GGCGCTGCCG    600

GGTGTTGGGC  CCAAGATGGC  ACACCTGGCT  ATGGCTGTGG  CCTGGGGCAC  TGTGTCAGGC    660

ATTGCAGTGG  ACACGCATGT  GCACAGAATC  GCCAACAGGC  TGAGGTGGAC  CAAGAAGGCA    720

ACCAAGTCCC  CAGAGGAGAC  CCGCGCCGCC  CTGGAGGAGT  GGCTGCCTAG  GGAGCTGTGG    780

CACGAGATCA  ATGGACTCTT  GGTGGGCTTC  GGCCAGCAGA  CCTGTCTGCC  TGTGCACCCT    840

CGCTGCCACG  CCTGCCTCAA  CCAAGCCCTC  TGCCCGGCCG  CCCAGGGTCT  CTGA          894
```

( 2 ) INFORMATION FOR SEQ ID NO:42:

( i ) SEQUENCE CHARACTERISTICS:
        ( A ) LENGTH: 297 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Homo sapiens ( x i ) SEQUENCE DESCRIPTION: SEQ ID NO:42:

```
Met Leu Thr Arg Ser Arg Ser Leu Gly Pro Gly Ala Gly Pro Arg Gly
 1               5                  10                  15

Cys Arg Glu Glu Pro Gly Pro Leu Arg Arg Glu Ala Ala Ala Glu
             20                  25                  30

Ala Arg Lys Ser His Ser Pro Val Lys Arg Pro Arg Lys Ala Gln Arg
         35                  40                  45

Leu Arg Val Ala Tyr Glu Gly Ser Asp Ser Glu Lys Gly Glu Gly Ala
     50                  55                  60

Glu Pro Leu Lys Val Pro Val Trp Glu Pro Gln Asp Trp Gln Gln Gln
 65                  70                  75                  80

Leu Val Asn Ile Arg Ala Met Arg Asn Lys Lys Asp Ala Pro Val Asp
                 85                  90                  95

His Leu Gly Thr Glu His Cys Tyr Asp Ser Ala Pro Pro Lys Val
                100                 105                 110

Arg Arg Tyr Gln Val Leu Leu Ser Leu Met Leu Ser Ser Gln Thr Lys
             115                 120                 125

Asp Gln Val Thr Ala Gly Ala Met Gln Arg Leu Arg Ala Arg Gly Leu
         130                 135                 140

Thr Val Asp Ser Ile Leu Gln Thr Asp Asp Ala Thr Leu Gly Lys Leu
145                 150                 155                 160

Ile Tyr Pro Val Gly Phe Trp Arg Ser Lys Val Lys Tyr Ile Lys Gln
                 165                 170                 175

Thr Ser Ala Ile Leu Gln Gln His Tyr Gly Gly Asp Ile Pro Ala Ser
             180                 185                 190

Val Ala Glu Leu Val Ala Leu Pro Gly Val Gly Pro Lys Met Ala His
             195                 200                 205
```

| | | | | | | | | | | | | | | |
|---|---|---|---|---|---|---|---|---|---|---|---|---|---|---|
| Leu | Ala 210 | Met | Ala | Val | Ala | Trp 215 | Gly | Thr | Val | Ser | Gly 220 | Ile | Ala | Val | Asp |
| Thr 225 | His | Val | His | Arg | Ile 230 | Ala | Asn | Arg | Leu | Arg 235 | Trp | Thr | Lys | Lys | Ala 240 |
| Thr | Lys | Ser | Pro | Glu 245 | Glu | Thr | Arg | Ala | Ala 250 | Leu | Glu | Glu | Trp | Leu 255 | Pro |
| Arg | Glu | Leu | Trp 260 | His | Glu | Ile | Asn | Gly 265 | Leu | Leu | Val | Gly | Phe 270 | Gly | Gln |
| Gln | Thr | Cys 275 | Leu | Pro | Val | His | Pro 280 | Arg | Cys | His | Ala | Cys 285 | Leu | Asn | Gln |
| Ala | Leu 290 | Cys | Pro | Ala | Ala | Gln 295 | Gly | Leu | | | | | | | |